United States Patent
Dunne et al.

(10) Patent No.: US 11,478,428 B2
(45) Date of Patent: Oct. 25, 2022

(54) COMBINATIONS OF BETA-LACTAM COMPOUNDS AND PROBENECID AND USES THEREOF

(71) Applicant: Iterum Therapeutics International Limited, Dublin (IE)

(72) Inventors: Michael Dunne, Old Saybrook, CT (US); Tom Loughman, Dublin (IE); Aaron Cameron, Dublin (IE)

(73) Assignee: Iterum Therapeutics International Limited, Dublin (IE)

( * ) Notice: Subject to any disclaimer, the term of this patent is extended or adjusted under 35 U.S.C. 154(b) by 0 days.

(21) Appl. No.: 16/972,300

(22) PCT Filed: Dec. 23, 2019

(86) PCT No.: PCT/EP2019/086975
§ 371 (c)(1),
(2) Date: Dec. 4, 2020

(87) PCT Pub. No.: WO2020/164788
PCT Pub. Date: Aug. 20, 2020

(65) Prior Publication Data
US 2021/0154176 A1 May 27, 2021

Related U.S. Application Data

(60) Provisional application No. 62/804,973, filed on Feb. 13, 2019.

(51) Int. Cl.
*A61K 9/24* (2006.01)
*A61K 9/28* (2006.01)
*A61K 31/195* (2006.01)
*A61K 31/397* (2006.01)
*A61K 9/20* (2006.01)
*A61K 31/431* (2006.01)

(52) U.S. Cl.
CPC .......... *A61K 9/209* (2013.01); *A61K 9/2013* (2013.01); *A61K 9/2018* (2013.01); *A61K 9/2054* (2013.01); *A61K 9/2095* (2013.01); *A61K 9/282* (2013.01); *A61K 9/2866* (2013.01); *A61K 31/195* (2013.01); *A61K 31/397* (2013.01); *A61K 31/431* (2013.01)

(58) Field of Classification Search
CPC ........ A61K 9/209; A61K 9/09; A61K 9/2013; A61K 9/2018; A61K 9/2054; A61K 9/2095; A61K 9/282; A61K 9/2866; A61K 31/195; A61K 31/997; A61K 31/431

See application file for complete search history.

(56) References Cited

U.S. PATENT DOCUMENTS

| | | | |
|---|---|---|---|
| 4,522,811 | A | 6/1985 | Eppstein et al. |
| 2002/0119195 | A1 | 8/2002 | Sen et al. |
| 2005/0031685 | A1 | 2/2005 | Sen et al. |
| 2008/0009474 | A1 | 1/2008 | Brighty et al. |
| 2008/0125408 | A1 | 5/2008 | Brighty et al. |
| 2012/0282336 | A1* | 11/2012 | Abebe .............. A61K 31/70 424/465 |
| 2016/0022632 | A1 | 1/2016 | Rothenberg et al. |
| 2019/0374516 | A1 | 12/2019 | Dunne |
| 2020/0253878 | A1 | 8/2020 | Dunne et al. |

FOREIGN PATENT DOCUMENTS

| | | |
|---|---|---|
| CN | 1813700 A | 8/2006 |
| CN | 1853724 A | 11/2006 |
| EP | 3 238 713 A1 | 11/2017 |
| WO | WO 99/49875 A1 | 10/1999 |
| WO | WO 02/36126 A1 | 5/2002 |
| WO | WO 02/41876 A1 | 5/2002 |
| WO | WO 03/043607 A1 | 5/2003 |
| WO | WO 2008/001212 A2 | 1/2008 |

OTHER PUBLICATIONS

Ambrose, P. G. et al., "Pharmacokinetics-Pharmacodynamics of Antimicrobial Therapy: It's Not Just for Mice Anymore," Clinical Infectious Diseases, 44:79-86 (2007).
Chandra, R. et al., "Pharmacokinetics (PK), Safety and Tolerability of Single Oral Doses of PF-03709270, with and without Co-Administration of Probenecid," Jan. 1, 2008, Abstract, Interscience Conference on Antimicrobial Agents & Chemotherapy (ICAAC), vol. 48, 1 page.
Chandra, R. et al., "Pharmacokinetics (PK), Safety and Tolerability of Single Oral Doses of PF-03709270, with and without Co-Administration of Probenecid- Introduction," Oct. 25, 2008, retrieved from the Internet: https://dli03yog0oux5.cloudfront.net/_bb13d2baffc18226dOc894be0676522b/iterumtx/db/395/2620/pdf, 1 page.
Cox, V. C. & Zed, P. J., "Once-Daily Cefazolin and Probenecid for Skin and Soft Tissue Infections," Ann Pharmacother, 38:458-463 (2004).
Cunningham, R. F. et al., "Clinical Pharmacokinetics of Probenecid," Clinical Pharmacokinetics, 6:135-151 (1981).
Dacey, R. G. & Sande, M. A., "Effect of Probenecid on Cerebrospinal Fluid Concentrations of Penicillin and Cephalosporin Derivatives," Antimicrobial Agents and Chemotherapy, 6(4):437-441 (1974).
Dalen, D. et al., "Intravenous cefazolin plus oral probenecid versus oral cephalexin for the treatment of skin and soft tissue infections: a double-blind, non-inferiority, randomised controlled trial," Emergency Medicine Journal, 35(8):492-498 (2018).

(Continued)

*Primary Examiner* — Adam C Milligan
(74) *Attorney, Agent, or Firm* — Cooley LLP; William T. Christiansen, II; Heng Zhang

(57) ABSTRACT

The present disclosure relates to bilayer tablets comprising a second layer comprising a β-lactam compound or a pharmaceutically acceptable salt thereof; and a first layer comprising probenecid or a pharmaceutically acceptable salt thereof. The present disclosure also relates to methods of treating or preventing a disease using the bilayer tablets.

10 Claims, 15 Drawing Sheets

(56) References Cited

OTHER PUBLICATIONS

Dominy, S. S. et al., "*Porphyromonas gingivalis* in Alzheimer's disease brains: Evidence for disease causation and treatment with small-molecule inhibitors," Sci. Adv. 5:eaau333 (2019), 21 pages.

Dörwald, F. Z., "Side Reactions in Organic Synthesis: a Guide of Successful Synthesis Design," Preface, 2005 Wiley-VCH Verlag GmbH & Co. KGaA, 4 pages.

Dunne, M. et al., "A Phase 1 Study to Assess the Pharmacokinetics of Sulopenem Etzadroxil (PF-03709270)," Poster Abstracts, OFID 2017:4 (Suppl 1):S525-S526, 2 pages.

Dunne, M. et al., "A Phase 1, Randomized, Open-Label, Crossover Study in Healthy Subjects Under Fasting Conditions of Orally Administered Sulopenem Etzadroxil Alone or with Probenecid to Determine the Pharmacokinetics of Sulopenem," Poster Abstracts, OFID 2018:5 (Suppl 1):S428-S429, 2 pages.

Ednie, L. M. & Applebaum, P. C., "Antianaerobic Activity of Sulopenem Compared to Six Other Agents," Antimicrobial Agents and Chemotherapy, 53(5):2163-2170 (2009).

Forrest, A. et al., "PK/PD Analysis to Select PF-03709270 (PF) Doses, With & Without Probenecid (P), for Phase 2b Trials," Abstract, Interscience Conference on Antimicrobial Agents & Chemotherapy (ICAAC), vol. 48, Oct. 25, 2008, 1 page.

Gootz, T. et al., "Pharmacokinetic studies in animals of a new parenteral penem CP-65,207 and its oral prodrug ester," The Journal of Antibiotics, 43(4):422-432 (1990).

Karlowsky, J. A. et al., "In Vitro Activity of Sulopenem, an Oral Penem, against Urinary Isolates of *Escherichia coli*," Antimicrob Agents Chemother 63(1):e01832-18 (2019), 7 pages; https://doi.org/10.1128/AAC.01832-18.

Stamm, W. E., "An Epidemic of Urinary Tract Infections?" Editorials—N Engl J Med, 345(14):1055-1057 (2001).

Soma, K. et al., "Pharmacokinetics (PK), Safety and Tolerability of Multiple Doses (MD) of Intravenous (IV) and Oral (PO) Sulopenem (S) and Sulopenem Etzadroxil (SE)," 2009, Abstract, Interscience Conference on Antimicrobial Agents & Chemotherapy (ICAAC), vol. 49, 2 pages.

Le, J. et al., "Drug Bioavailability," Oct. 2020, 2 pages; https://www.merckmanuals.com/professional/clinical-pharmacology/pharmacokinetics/drug-bioavalability#.

Probenicid, Tulane University, Medical Pharmacology, 2016; http://tmedweb.tulane.edu/pharmawiki/doku.php/probenecid, 3 pages.

Stocker, S. L. et al., Pharmacokinetic and Pharmacodynamic Interaction Between Allopurinol and Probenecid in Patients with Gout, J. Rheumatol, 38:904-910 (2011).

Urination Problems, Military Obstetrics & Gynecology, 2009, 2014, 8 pages.

Van Der Merwe, J. et al., "The Role of Functional Excipients in Solid Oral Dosage Forms to Overcome Poor Drug Dissolution and Bioavailability," Pharmaceutics, 12:393 (2020), 17 pages.

* cited by examiner

COMBINATIONS OF BETA-LACTAM COMPOUNDS AND PROBENECID AND USES THEREOF

RELATED APPLICATIONS

This application is a U.S. National Stage Application under 35 U. S. C. § 371 of International Application No. PCT/EP2019/086975, filed on Dec. 23, 2019, which claims priority to, and the benefit of, U.S. Provisional Application No. 62/804,973, filed Feb. 13, 2019, the entire contents of each of which are incorporated herein by reference.

BACKGROUND

β-lactam compounds are a class of antibiotics having a beta-lactam ring in their molecular structures. β-lactam compounds have been used in the treatment of diseases associated with Gram-positive and Gram-negative bacteria. The mechanism of action of these β-lactam compounds requires, optimally, that concentrations of the antibiotic remain at or above a certain inhibitory threshold, known as the 'minimum inhibitory concentration (MIC)' in order to be effective. Keeping these antibiotic concentrations elevated also helps avoid the potential for antibacterial resistance due to the selection of bacteria with higher MIC's. There is, therefore, a need for compositions and methods related to β-lactam antibiotics that optimize their tissue concentrations in order to improve their ability to control an infection as well as alleviate or eliminate the potential for antibiotic resistance.

SUMMARY

The present disclosure provides, inter alia, a bilayer tablet comprising:
a first layer comprising probenecid or the pharmaceutically acceptable salt thereof and
a second layer comprising the β-lactam compound or the pharmaceutically acceptable salt thereof.

In some aspects, the present disclosure provides a method of preparing a bilayer tablet, comprising:
i) compressing a first granular material comprising probenecid or a pharmaceutically acceptable salt thereof with a first force, thereby forming a pre-compressed first layer;
ii) adding a second granular material comprising a β-lactam compound or a pharmaceutically acceptable salt thereof to the pre-compressed first layer;
iii) compressing the pre-compressed first layer and the second granular material with a second force, thereby forming a pre-coated bilayer tablet.

In some aspects, the present disclosure provides a bilayer tablet being prepared by a method of disclosed herein.

In some aspects, the present disclosure provides a method of treating or preventing a disease, comprising administering to a subject in need thereof a bilayer tablet described herein.

In some aspects, the present disclosure provides a bilayer tablet described herein for use in treating or preventing a disease in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF DRAWINGS

FIG. 4A is a diagram comparing the in vitro release of probenecid for Batch Nos. 1-3 of the bilayer tablet and a comparable commercial tablet of probenecid. FIG. 4B is a diagram showing the in vitro release of the β-lactam compound (Compound III-2b) and probenecid for Batch No. 4 of the bilayer tablet. FIG. 4C is a diagram showing the in vitro release of the β-lactam compound (Compound III-2b) and probenecid for Batch No. 5 of the bilayer tablet. FIG. 4D is a diagram showing the in vitro release of the β-lactam compound (Compound III-2b) and probenecid for Batch No. 6 of the bilayer tablet.

FIG. 5A is a diagram comparing the total volume of the bilayer tablets. FIG. 5B is a diagram comparing the porosity of the bilayer tablets. FIG. 5C is a diagram comparing the total pore surface area of the bilayer tablets. FIG. 5D is a diagram comparing the total pore count of the bilayer tablets. FIG. 5E is a diagram comparing the volume of the largest pore of the bilayer tablets. FIG. 5F is a diagram comparing the volume ratio between the largest pore and the total pore of the bilayer tablets. FIG. 5G is a diagram showing the in vitro release characteristics of an exemplary batch of bilayer tablets prepared by high compression force.

DETAILED DESCRIPTION

Figure 1:
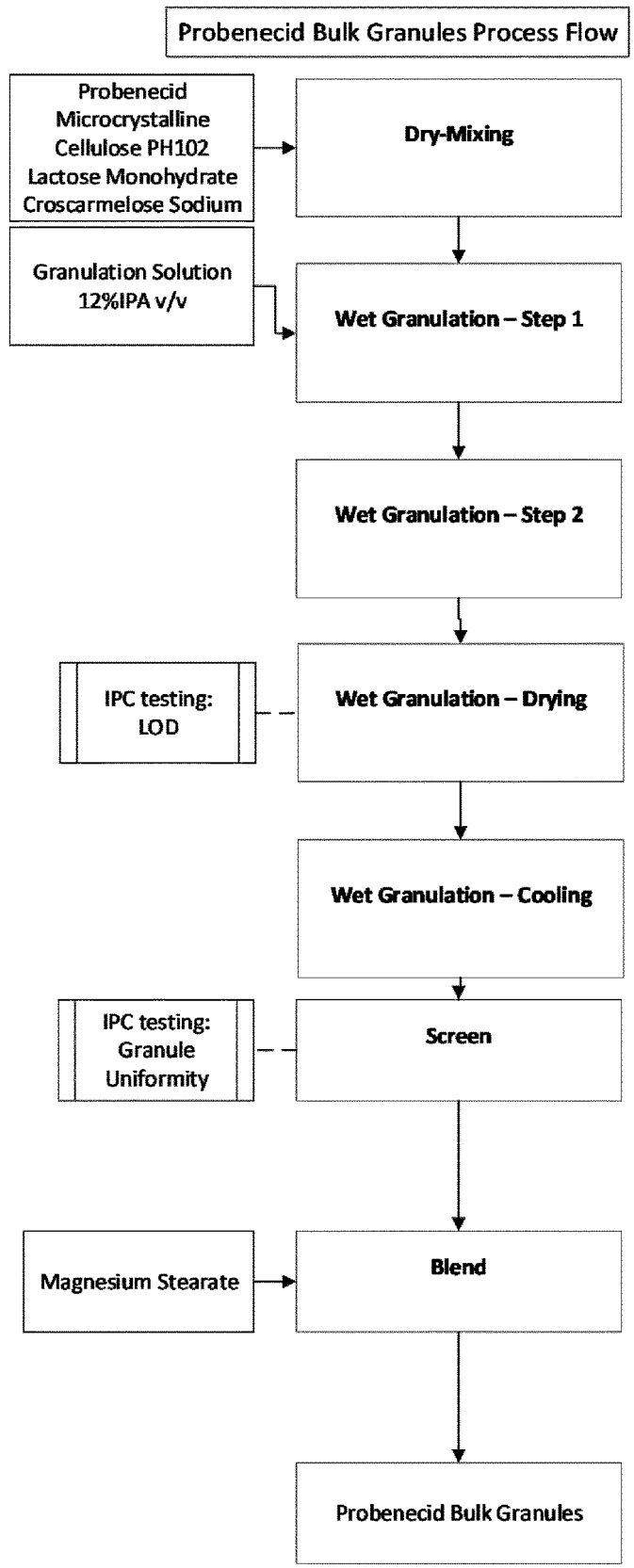
FIG. 1 is a diagram describing an exemplary process of preparing the granular material of probenecid.

The present disclosure provides, inter alia, a bilayer tablet, comprising:

a second layer comprising the β-lactam compound or the pharmaceutically acceptable salt thereof; and a first layer comprising probenecid or the pharmaceutically acceptable salt thereof.

In some embodiments, the first layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof.

In some embodiments, the second layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound (e.g., Compound III-2, Compound III-2a, or Compound III-2b) or the pharmaceutically acceptable salt thereof.

In some embodiments, the first layer comprises about 500±1000 mg, about 500±900 mg, about 500±800 mg, about 500±700 mg, about 500±600 mg, about 500±500 mg, about 500±450 mg, about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of probenecid or the pharmaceutically acceptable salt thereof.

In some embodiments, the second layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of the β-lactam compound (e.g., Compound III-2, Compound III-2a, or Compound III-2b) or the pharmaceutically acceptable salt thereof and the first layer comprises from 20 mg to about 5 g, from about 50 mg to about 2 g, from about 80 mg to about 1 g, from about 100 mg to about 900 mg, from about 200 mg to about 800 mg, from about 300 mg to about 700 mg, from about 400 mg to about 600 mg, from about 450 mg to about 550 mg, or from about 480 mg to about 520 mg of probenecid or the pharmaceutically acceptable salt thereof.

In some embodiments, the second layer comprises about 500±1000 mg, about 500±900 mg, about 500±800 mg, about 500±700 mg, about 500±600 mg, about 500±500 mg, about 500±450 mg, about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of the β-lactam compound (e.g., Compound III-2, Compound III-2a, or Compound III-2b) or the pharmaceutically acceptable salt thereof.

In some embodiments, the first layer comprises about 500±1000 mg, about 500±900 mg, about 500±800 mg, about 500±700 mg, about 500±600 mg, about 500±500 mg, about 500±450 mg, about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of probenecid or the pharmaceutically acceptable salt thereof and the second layer comprises about 500±1000 mg, about 500±900 mg, about 500±800 mg, about 500±700 mg, about 500±600 mg, about 500±500 mg, about 500±450 mg, about 500±400 mg, about 500±350 mg, about 500±300 mg, about 500±250 mg, about 500±200 mg, about 500±150 mg, about 500±100 mg, about 500±90 mg, about 500±80 mg, about 500±70 mg, about 500±60 mg, about 500±50 mg, about 500±45 mg, about 500±40 mg, about 500±35 mg, about 500±30 mg, about 500±25 mg, about 500±20 mg, about 500±15 mg, about 500±10 mg, or about 500±5 mg of the β-lactam compound (e.g., Compound III-2, Compound III-2a, or Compound III-2b) or the pharmaceutically acceptable salt thereof.

In some embodiments, the first layer comprises about 500 mg of probenecid or the pharmaceutically acceptable salt thereof.

In some embodiments, the second layer comprises about 500 mg of the β-lactam compound (e.g., Compound III-2, Compound III-2a, or Compound III-2b) or the pharmaceutically acceptable salt thereof.

In some embodiments, the first layer of the bilayer tablet comprises about 50 mg, about 100 mg, about 200 mg, about 300 mg, about 400 mg, about 500 mg, about 600 mg, about 700 mg, about 800 mg, about 900 mg, or about 1 g of probenecid.

In some embodiments, the first layer of the bilayer tablet comprises about 500 mg of probenecid.

In some embodiments, the second layer comprises about 500 mg of the β-lactam compound (e.g., Compound III-2, Compound III-2a, or Compound III-2b) or the pharmaceutically acceptable salt thereof and the first layer comprises about 500 mg of probenecid or the pharmaceutically acceptable salt thereof.

In some embodiments, the second layer comprises:

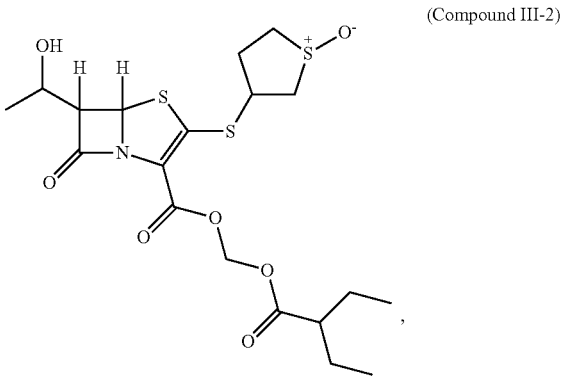

(Compound III-2)

-continued (Compound III-2a)

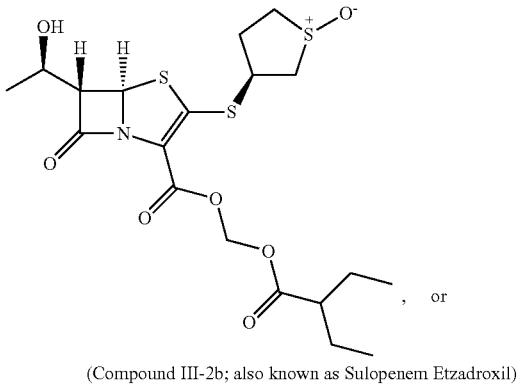

(Compound III-2b; also known as Sulopenem Etzadroxil)

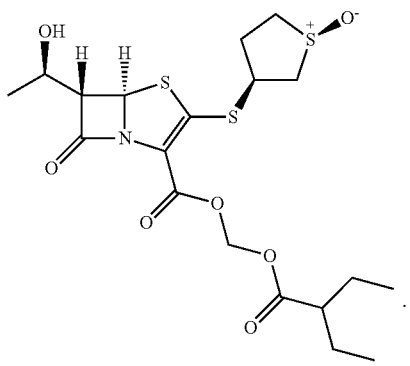

In some embodiments, the second layer comprises Compound III-2.

In some embodiments, the second layer comprises Compound III-2a.

In some embodiments, the second layer comprises Compound III-2b.

In some embodiments, the second layer of the bilayer tablet comprises about 50 mg, about 100 mg, about 200 mg, about 300 mg, about 400 mg, about 500 mg, about 600 mg, about 700 mg, about 800 mg, about 900 mg, or about 1 g of Compound III-2, Compound III-2a, or Compound III-2b.

In some embodiments, the second layer of the bilayer tablet comprises about 50 mg, about 100 mg, about 200 mg, about 300 mg, about 400 mg, about 500 mg, about 600 mg, about 700 mg, about 800 mg, about 900 mg, or about 1 g of Compound III-2.

In some embodiments, the second layer of the bilayer tablet comprises about 50 mg, about 100 mg, about 200 mg, about 300 mg, about 400 mg, about 500 mg, about 600 mg, about 700 mg, about 800 mg, about 900 mg, or about 1 g of Compound III-2a.

In some embodiments, the second layer of the bilayer tablet comprises about 50 mg, about 100 mg, about 200 mg, about 300 mg, about 400 mg, about 500 mg, about 600 mg, about 700 mg, about 800 mg, about 900 mg, or about 1 g of Compound III-2b.

In some embodiments, the second layer of the bilayer tablet comprises about 500 mg of Compound III-2, Compound III-2a, or Compound III-2b.

In some embodiments, the second layer of the bilayer tablet comprises about 500 mg of Compound III-2.

In some embodiments, the second layer of the bilayer tablet comprises about 500 mg of Compound III-2a.

In some embodiments, the second layer of the bilayer tablet comprises about 500 mg of Compound III-2b.

In some embodiments, bilayer tablet further comprises one or more of pharmaceutical excipients.

In some embodiments, the one or more of pharmaceutical excipients are selected from cellulose, sodium croscamellose, magnesium stearate, lactose monohydrate, and hydroxypropylcellulose.

In some embodiments, the bilayer tablet further comprises about 227±200 mg, about 227±150 mg, about 227±100 mg, about 227±90 mg, about 227±80 mg, about 227±70 mg, about 227±60 mg, about 227±50 mg, about 227±40 mg, about 227±30 mg, about 227±20 mg, about 227±15 mg, about 227±10 mg, or about 227±5 mg of microcrystalline cellulose (e.g., about 227 mg of microcrystalline cellulose).

In some embodiments, the bilayer tablet further comprises about 225±200 mg, about 225±150 mg, about 225±100 mg, about 225±90 mg, about 225±80 mg, about 225±70 mg, about 225±60 mg, about 225±50 mg, about 225±40 mg, about 225±30 mg, about 225±20 mg, about 225±15 mg, about 225±10 mg, or about 225±5 mg of microcrystalline cellulose (e.g., about 225 mg of microcrystalline cellulose).

In some embodiments, the bilayer tablet further comprises about 56±50 mg, about 56±45 mg, about 56±40 mg, about 56±35 mg, about 56±30 mg, about 56±25 mg, about 56±20 mg, about 56±15 mg, about 56±10 mg, about 56±5 mg, about 56±4 mg, about 56±3 mg, or about 56±2 mg of sodium croscamellose (e.g., about 56 mg of sodium croscamellose).

In some embodiments, the bilayer tablet further comprises about 3.3±3 mg, about 3.3±2.5 mg, about 3.3±2 mg, about 3.3±1.8 mg, about 3.3±1.6 mg, about 3.3±1.4 mg, about 3.3±1.2 mg, about 3.3±1 mg, about 3.3±0.9 mg, about 3.3±0.8 mg, about 3.3±0.7 mg, about 3.3±0.6 mg, about 3.3±0.5 mg, about 3.3±0.4 mg, about 3.3±0.3 mg, about 3.3±0.2 mg, or about 3.3±0.1 mg of intragranular magnesium stearate (e.g., about 3.3 mg of intragranular magnesium stearate).

In some embodiments, the bilayer tablet further comprises about 6.9±3 mg, about 6.9±2.5 mg, about 6.9±2 mg, about 6.9±1.8 mg, about 6.9±1.6 mg, about 6.9±1.4 mg, about 6.9±1.2 mg, about 6.9±1 mg, about 6.9±0.9 mg, about 6.9±0.8 mg, about 6.9±0.7 mg, about 6.9±0.6 mg, about 6.9±0.5 mg, about 6.9±0.4 mg, about 6.9±0.3 mg, about 6.9±0.2 mg, or about 6.9±0.1 mg of extragranular magnesium stearate (e.g., about 6.9 mg of extragranular magnesium stearate).

In some embodiments, the bilayer tablet further comprises about 70±50 mg, about 70±45 mg, about 70±40 mg, about 70±35 mg, about 70±30 mg, about 70±25 mg, about 70±20 mg, about 70±15 mg, about 70±10 mg, about 70±5 mg, about 70±4 mg, about 70±3 mg, or about 70±2 mg of lactose monohydrate 316 (e.g., about 70 mg of lactose monohydrate 316).

In some embodiments, the bilayer tablet further comprises about 69±50 mg, about 69±45 mg, about 69±40 mg, about 69±35 mg, about 69±30 mg, about 69±25 mg, about 69±20 mg, about 69±15 mg, about 69±10 mg, about 69±5 mg, about 69±4 mg, about 69±3 mg, or about 69±2 mg of lactose monohydrate 316 (e.g., about 69 mg of lactose monohydrate 316).

In some embodiments, the bilayer tablet further comprises about 21±20 mg, about 21±15 mg, about 21±10 mg, about 21±5 mg, about 21±4 mg, about 21±3 mg, about 21±2 mg, about 21±1.8 mg, about 21±1.6 mg, about 21±1.4 mg, about 21±1.2 mg, about 21±1 mg, about 21±0.9 mg, about 21±0.8 mg, about 21±0.7 mg, about 21±0.6 mg, or about 21±0.5 mg of hydroxypropylcellulose (e.g., about 21.4 mg of hydroxypropylcellulose).

In some aspects, the present disclosure provides a bilayer tablet comprising:
 a first layer comprising about 500 mg of probenecid; and
 a second layer comprising about 500 mg of Compound III-2b.

In some embodiments, the bilayer tablet further comprises:
 about 227±200 mg, about 227±150 mg, about 227±100 mg, about 227±90 mg, about 227±80 mg, about 227±70 mg, about 227±60 mg, about 227±50 mg, about 227±40 mg, about 227±30 mg, about 227±20 mg, about 227±15 mg, about 227±10 mg, or about 227±5 mg of microcrystalline cellulose;
 about 56±50 mg, about 56±45 mg, about 56±40 mg, about 56±35 mg, about 56±30 mg, about 56±25 mg, about 56±20 mg, about 56±15 mg, about 56±10 mg, about 56±5 mg, about 56±4 mg, about 56±3 mg, or about 56±2 mg of sodium croscamellose;
 about 3.3±3 mg, about 3.3±2.5 mg, about 3.3±2 mg, about 3.3±1.8 mg, about 3.3±1.6 mg, about 3.3±1.4 mg, about 3.3±1.2 mg, about 3.3±1 mg, about 3.3±0.9 mg, about 3.3±0.8 mg, about 3.3±0.7 mg, about 3.3±0.6 mg, about 3.3±0.5 mg, about 3.3±0.4 mg, about 3.3±0.3 mg, about 3.3±0.2 mg, or about 3.3±0.1 mg of intragranular magnesium stearate;
 about 6.9±3 mg, about 6.9±2.5 mg, about 6.9±2 mg, about 6.9±1.8 mg, about 6.9±1.6 mg, about 6.9±1.4 mg, about 6.9±1.2 mg, about 6.9±1 mg, about 6.9±0.9 mg, about 6.9±0.8 mg, about 6.9±0.7 mg, about 6.9±0.6 mg, about 6.9±0.5 mg, about 6.9±0.4 mg, about 6.9±0.3 mg, about 6.9±0.2 mg, or about 6.9±0.1 mg of extragranular magnesium stearate;
 about 70±50 mg, about 70±45 mg, about 70±40 mg, about 70±35 mg, about 70±30 mg, about 70±25 mg, about 70±20 mg, about 70±15 mg, about 70±10 mg, about 70±5 mg, about 70±4 mg, about 70±3 mg, or about 70±2 mg of lactose monohydrate 316; and about 21±20 mg, about 21±15 mg, about 21±10 mg, about 21±5 mg, about 21±4 mg, about 21±3 mg, about 21±2 mg, about 21±1.8 mg, about 21±1.6 mg, about 21±1.4 mg, about 21±1.2 mg, about 21±1 mg, about 21±0.9 mg, about 21±0.8 mg, about 21±0.7 mg, about 21±0.6 mg, or about 21±0.5 mg of hydroxypropylcellulose.

In some embodiments, the bilayer tablet further comprises:
 about 225±200 mg, about 225±150 mg, about 225±100 mg, about 225±90 mg, about 225±80 mg, about 225±70 mg, about 225±60 mg, about 225±50 mg, about 225±40 mg, about 225±30 mg, about 225±20 mg, about 225±15 mg, about 225±10 mg, or about 225±5 mg of microcrystalline cellulose;
 about 56±50 mg, about 56±45 mg, about 56±40 mg, about 56±35 mg, about 56±30 mg, about 56±25 mg, about 56±20 mg, about 56±15 mg, about 56±10 mg, about 56±5 mg, about 56±4 mg, about 56±3 mg, or about 56±2 mg of sodium croscamellose;
 about 3.3±3 mg, about 3.3±2.5 mg, about 3.3±2 mg, about 3.3±1.8 mg, about 3.3±1.6 mg, about 3.3±1.4 mg, about 3.3±1.2 mg, about 3.3±1 mg, about 3.3±0.9 mg, about 3.3±0.8 mg, about 3.3±0.7 mg, about 3.3±0.6 mg, about 3.3±0.5 mg, about 3.3±0.4 mg, about 3.3±0.3 mg, about 3.3±0.2 mg, or about 3.3±0.1 mg of intragranular magnesium stearate;
 about 6.9±3 mg, about 6.9±2.5 mg, about 6.9±2 mg, about 6.9±1.8 mg, about 6.9±1.6 mg, about 6.9±1.4 mg, about 6.9±1.2 mg, about 6.9±1 mg, about 6.9±0.9 mg, about 6.9±0.8 mg, about 6.9±0.7 mg, about 6.9±0.6 mg, about 6.9±0.5 mg, about 6.9±0.4 mg, about 6.9±0.3 mg, about 6.9±0.2 mg, or about 6.9±0.1 mg of extragranular magnesium stearate;
 about 69±50 mg, about 69±45 mg, about 69±40 mg, about 69±35 mg, about 69±30 mg, about 69±25 mg, about 69±20 mg, about 69±15 mg, about 69±10 mg, about 69±5 mg, about 69±4 mg, about 69±3 mg, or about 69±2 mg of lactose monohydrate 316; and about 21±20 mg, about 21±15 mg, about 21±10 mg, about 21±5 mg, about 21±4 mg, about 21±3 mg, about 21±2 mg, about 21±1.8 mg, about 21±1.6 mg, about 21±1.4 mg, about 21±1.2 mg, about 21±1 mg, about 21±0.9 mg, about 21±0.8 mg, about 21±0.7 mg, about 21±0.6 mg, or about 21±0.5 mg of hydroxypropylcellulose.

In some embodiments, the bilayer tablet further comprises:
 from about 220 mg to about 230 mg of microcrystalline cellulose;
 from about 50 mg to about 60 mg of sodium croscamellose;
 from about 3 mg to about 4 mg of intragranular magnesium stearate;
 from about 6 mg to about 8 mg of extragranular magnesium stearate;
 from about 65 mg to about 75 mg of lactose monohydrate 316; and
 from about 20 to about 23 mg of hydroxypropylcellulose.

In some embodiments, the bilayer tablet further comprises:
 about 227 mg of microcrystalline cellulose;
 about 56 mg of sodium croscamellose;
 about 3.3 mg of intragranular magnesium stearate;
 about 6.9 mg of extragranular magnesium stearate;
 about 70 mg of lactose monohydrate 316; and
 about 21.4 mg of hydroxypropylcellulose.

In some embodiments, the bilayer tablet further comprises:
 about 225 mg of microcrystalline cellulose;
 about 56 mg of sodium croscamellose;
 about 3.3 mg of intragranular magnesium stearate;
 about 6.9 mg of extragranular magnesium stearate;
 about 69 mg of lactose monohydrate 316; and
 about 21.4 mg of hydroxypropylcellulose.

In some embodiments, the bilayer tablet is prepared by a method disclosed herein.

In some aspects, the present disclosure provides a bilayer tablet prepared by a method disclosed herein.

Physical Properties of the Bilayer Tablets

In some embodiments, the bilayer tablet is configured to have a white color, a yellow color, a pink color, or any color therebetween.

In some embodiments, the bilayer tablet is configured to have an oval shape.

In some embodiments, the bilayer tablet is configured to have a length of about 19±10 mm, about 19±9 mm, about 19±8 mm, about 19±7 mm, about 19±6 mm, about 19±5 mm, about 19±4 mm, about 19±3 mm, about 19±2 mm, about 19±1 mm, about 19±0.8 mm, about 19±0.6 mm, about 19±0.5 mm, about 19±0.4 mm, about 19±0.3 mm, about 19±0.2 mm, or about 19±0.1 mm (e.g., about 19 mm).

In some embodiments, the bilayer tablet is configured to have a width of about 10.3±20 mm, about 10.3±18 mm, about 10.3±16 mm, about 10.3±14 mm, about 10.3±12 mm, about 10.3±10 mm, about 10.3±9 mm, about 10.3±8 mm, about 10.3±7 mm, about 10.3±6 mm, about 10.3±5 mm, about 10.3±4 mm, about 10.3±3 mm, about 10.3±2 mm, about 10.3±1 mm, about 10.3±0.8 mm, about 10.3±0.6 mm, about 10.3±0.5 mm, about 10.3±0.4 mm, about 10.3±0.3 mm, about 10.3±0.2 mm, or about 10.3±0.1 mm (e.g., about 10.3 mm).

In some embodiments, the bilayer tablet is configured to have a thickness of about 8.2±20 mm, about 8.2±18 mm, about 8.2±16 mm, about 8.2±14 mm, about 8.2±12 mm, about 8.2±10 mm, about 8.2±9 mm, about 8.2±8 mm, about 8.2±7 mm, about 8.2±6 mm, about 8.2±5 mm, about 8.2±4 mm, about 8.2±3 mm, about 8.2±2 mm, about 8.2±1 mm, about 8.2±0.8 mm, about 8.2±0.6 mm, about 8.2±0.5 mm, about 8.2±0.4 mm, about 8.2±0.3 mm, or about 8.2±0.2 mm.

In some embodiments, the bilayer tablet is configured to have a hardness of greater than about 80 N, greater than about 85 N, greater than about 90 N, greater than about 95 N, greater than about 100 N, greater than about 105 N, greater than about 110 N, greater than about 115 N, greater than about 120 N, greater than about 125 N, greater than about 130 N, greater than about 140 N, greater than about 150 N, greater than about 160 N, greater than about 170 N, greater than about 180 N, greater than about 190 N, greater than about 200 N, greater than about 220 N, greater than about 240 N, greater than about 260 N, greater than about 270 N, greater than about 280 N, greater than about 290 N, or greater than about 300 N.

In some embodiments, the bilayer tablet is configured to have a hardness of greater than about 120 N.

In some embodiments, the bilayer tablet is configured to have a hardness of less than 300 N.

In some embodiments, the bilayer tablet is configured to have a hardness of greater than about 120 N and less than 300 N.

In some embodiments, the bilayer tablet is configured to have a friability of less than about 1%, less than about 0.9%, less than about 0.8%, less than about 0.7%, less than about 0.6%, less than about 0.5%, less than about 0.4%, less than about 0.3%, less than about 0.2%, or less than about 0.1%.

In some embodiments, the bilayer tablet is configured to have a friability of less than about 0.1%, less than about 0.09%, less than about 0.08%, less than about 0.07%, less than about 0.06%, less than about 0.05%, less than about 0.04%, less than about 0.03%, less than about 0.02%, or less than about 0.01%.

In some embodiments, the bilayer tablet is configured to have a total volume of less than 2000 mm$^3$, less than about 1900 mm$^3$, less than about 1800 mm$^3$, less than about 1700 mm$^3$, less than about 1600 mm$^3$, less than about 1500 mm$^3$, less than about 1400 mm$^3$, less than about 1300 mm$^3$, less than about 1250 mm$^3$, less than about 1240 mm$^3$, less than about 1230 mm$^3$, less than about 1220 mm$^3$, less than about 1210 mm$^3$, less than about 1200 mm$^3$, less than about 1190 mm$^3$, less than about 1180 mm$^3$, less than about 1170 mm$^3$, less than about 1160 mm$^3$, less than about 1150 mm$^3$, less than about 1140 mm$^3$, less than about 1130 mm$^3$, less than about 1120 mm$^3$, less than about 1110 mm$^3$, less than about 1100 mm$^3$, less than about 1080 mm$^3$, less than about 1060 mm$^3$, less than about 1040 mm$^3$, less than about 1020 mm$^3$, or less than about 1010 mm$^3$.

In some embodiments, the bilayer tablet is configured to have a total volume of about 1150±300 mm$^3$, about 1150±250 mm$^3$, about 1150±200 mm$^3$, about 1150±180 mm$^3$, about 1150±160 mm$^3$, about 1150±150 mm$^3$, about 1150±140 mm$^3$, about 1150±120 mm$^3$, about 1150±100 mm$^3$, about 1150±90 mm$^3$, about 1150±80 mm$^3$, about 1150±70 mm$^3$, about 1150±60 mm$^3$, about 1150±50 mm$^3$, about 1150±45 mm$^3$, about 1150±40 mm$^3$, about 1150±35 mm$^3$, about 1150±30 mm$^3$, about 1150±25 mm$^3$, about 1150±20 mm$^3$, about 1150±15 mm$^3$, about 1150±10 mm$^3$, about 1150±9 mm$^3$, about 1150±8 mm$^3$, about 1150±7 mm$^3$, about 1150±6 mm$^3$, about 1150±5 mm$^3$, about 1150±4 mm$^3$, mm$^3$, or about 1150±3 mm$^3$ (e.g., about 1148 mm$^3$).

In some embodiments, the bilayer tablet is configured to have a total volume of about 1050±300 mm$^3$, about 1050±250 mm$^3$, about 1050±200 mm$^3$, about 1050±180 mm$^3$, about 1050±160 mm$^3$, about 1050±150 mm$^3$, about 1050±140 mm$^3$, about 1050±120 mm$^3$, about 1050±100 mm$^3$, about 1050±90 mm$^3$, about 1050±80 mm$^3$, about 1050±70 mm$^3$, about 1050±60 mm$^3$, about 1050±50 mm$^3$, about 1050±45 mm$^3$, about 1050±40 mm$^3$, about 1050±35 mm$^3$, about 1050±30 mm$^3$, about 1050±25 mm$^3$, about 1050±20 mm$^3$, about 1050±15 mm$^3$, about 1050±10 mm$^3$, about 1050±9 mm$^3$, about 1050±8 mm$^3$, about 1050±7 mm$^3$, about 1050±6 mm$^3$, about 1050±5 mm$^3$, about 1050±4 mm$^3$, about 1050±3 mm$^3$, about 1050±2 mm$^3$, or about 1050±1 mm$^3$ (e.g., about 1050 mm$^3$).

In some embodiments, the bilayer tablet is configured to have a porosity of less than about 20%, less than about 15%, less than about 10%, less than about 9%, less than about 8%, less than about 7%, less than about 6%, less than about 5%, less than about 4%, less than about 3%, less than about 2%, less than about 1.8%, less than about 1.6%, less than about 1.4%, less than about 1.2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1%.

In some embodiments, the bilayer tablet is configured to have a porosity of about 0.73±0.5%, about 0.73±0.45%, about 0.73±0.4%, about 0.73±0.35%, about 0.73±0.3%, about 0.73±0.25%, about 0.73±0.2%, about 0.73±0.15%, about 0.73±0.1%, about 0.73±0.09%, about 0.73±0.08%, about 0.73±0.07%, about 0.73±0.06%, about 0.73±0.05%, about 0.73±0.04%, about 0.73±0.03%, about 0.73±0.02%, or about 0.73±0.01% (e.g., about 0.73%).

In some embodiments, the bilayer tablet is configured to have a total pore surface area of less than about 5,000,000 mm$^2$, less than about 4,000,000 mm$^2$, less than about 3,000,000 mm$^2$, less than about 2,000,000 mm$^2$, less than about 1,000,000 mm$^2$, less than about 900,000 mm$^2$, less than about 800,000 mm$^2$, less than about 700,000 mm$^2$, less than about 600,000 mm$^2$, less than about 500,000 mm$^2$, less than about 400,000 mm$^2$, less than about 300,000 mm$^2$, less than about 200,000 mm$^2$, less than about 100,000 mm$^2$, less than about 90,000 mm$^2$, less than about 80,000 mm$^2$, less than about 70,000 mm$^2$, less than about 60,000 mm$^2$, less than about 50,000 mm$^2$, less than about 40,000 mm$^2$, less than about 30,000 mm$^2$, less than about 20,000 mm$^2$, less than about 10,000 mm$^2$, less than about 9,000 mm$^2$, less than about 8,000 mm$^2$, less than about 7,000 mm$^2$, less than about 6,000 mm$^2$, less than about 5,000 mm$^2$, less than about 4900 mm$^2$, less than about 4800 mm$^2$, less than about 4700 mm$^2$, less than about 4600 mm$^2$, less than about 4500 mm$^2$, less than about 4400 mm$^2$, less than about 4300 mm$^2$, less than about 4200 mm$^2$, less than about 4100 mm$^2$, less than about 4,000 mm$^2$, less than about 3900 mm$^2$, less than about 3800 mm$^2$, less than about 3700 mm$^2$, less than about 3600 mm$^2$, less than about 3500 mm$^2$, less than about 3400 mm$^2$, less than about 3300 mm$^2$, less than about 3200 mm$^2$, less than about 3100 mm$^2$, less than about 3,000 mm$^2$, less than about 2900 mm$^2$, less than about 2800 mm$^2$, less than about 2700 mm$^2$, less than about 2600 mm$^2$, less than about 2500 mm$^2$, less than about 2400 mm$^2$, less than about 2300 mm$^2$, less than about 2200 mm$^2$, less than about 2100 mm$^2$, less than about 2,000 mm$^2$, less than about 1900 mm$^2$, less than about 1800 mm², less than about 1700 mm², less than about 1600 mm², less than about 1500 mm², less than about 1400 mm², less than about 1300 mm², less than about 1200 mm², less than about 1100 mm², or less than about 1,000 mm².

In some embodiments, the bilayer tablet is configured to have a total pore surface area of less than about 3,000 mm².

In some embodiments, the bilayer tablet is configured to have a total pore surface area of about 2050±1000 mm², about 2050±950 mm², about 2050±900 mm², about 2050±850 mm², about 2050±800 mm², about 2050±750 mm², about 2050±700 mm², about 2050±650 mm², about 2050±600 mm², about 2050±550 mm², about 2050±500 mm², about 2050±450 mm², about 2050±400 mm², about 2050±350 mm², about 2050±300 mm², about 2050±250 mm², about 2050±200 mm², about 2050±150 mm², about 2050±100 mm², about 2050±90 mm², about 2050±80 mm², about 2050±70 mm², about 2050±60 mm², about 2050±50 mm², about 2050±40 mm², about 2050±30 mm², about 2050±20 mm², about 2050±10 mm², or about 2050±5 mm² (e.g., about 2045 mm²).

In some embodiments, the bilayer tablet is configured to have a total pore count of about 1,000,000 or less, about 900,000 or less, about 800,000 or less, about 700,000 or less, about 600,000 or less, about 500,000 or less, about 400,000 or less, about 390,000 or less, about 380,000 or less, about 370,000 or less, about 360,000 or less, about 350,000 or less, about 340,000 or less, about 330,000 or less, about 320,000 or less, about 310,000 or less, about 300,000 or less, about 290,000 or less, about 280,000 or less, about 270,000 or less, about 260,000 or less, about 250,000 or less, about 240,000 or less, about 230,000 or less, about 220,000 or less, about 210,000 or less, about 200,000 or less, about 190,000 or less, about 180,000 or less, about 170,000 or less, about 160,000 or less, about 150,000 or less, about 140,000 or less, about 130,000 or less, about 120,000 or less, about 110,000 or less, about 100,000 or less, about 90,000 or less, about 80,000 or less, about 70,000 or less, about 60,000 or less, about 50,000 or less, about 40,000 or less, about 30,000 or less, about 20,000 or less, about 10,000 or less, about 9,000 or less, about 8,000 or less, about 7,000 or less, about 6,000 or less, or about 5,000 or less.

In some embodiments, the bilayer tablet is configured to have a total pore count of about 255,000±200,000, about 255,000±150,000, about 255,000±100,000, about 255,000±90,000, about 255,000±80,000, about 255,000±70,000, about 255,000±60,000, about 255,000±50,000, about 255,000±40,000, about 255,000±30,000, about 255,000±20,000, or about 255,000±10,000.

In some embodiments, the bilayer tablet is configured to have a largest pore volume of about 10 mm³ or less, about 9 mm³ or less, about 8 mm³ or less, about 7 mm³ or less, about 6 mm³ or less, about 5 mm³ or less, about 4 mm³ or less, about 3 mm³ or less, about 2 mm³ or less, about 1.9 mm³ or less, about 1.8 mm³ or less, about 1.7 mm³ or less, about 1.6 mm³ or less, about 1.5 mm³ or less, about 1.4 mm³ or less, about 1.3 mm³ or less, about 1.2 mm³ or less, about 1.1 mm³ or less, about 1.0 mm³ or less, about 0.95 mm³ or less, about 0.90 mm³ or less, about 0.85 mm³ or less, about 0.80 mm³ or less, about 0.75 mm³ or less, about 0.70 mm³ or less, about 0.65 mm³ or less, about 0.60 mm³ or less, about 0.55 mm³ or less, about 0.50 mm³ or less, about 0.45 mm³ or less, about 0.40 mm³ or less, about 0.35 mm³ or less, about 0.30 mm³ or less, about 0.25 mm³ or less, about 0.20 mm³ or less, about 0.15 mm³ or less, about 0.10 mm³ or less, about 0.09 mm³ or less, about 0.08 mm³ or less, about 0.07 mm³ or less, about 0.06 mm³ or less, about 0.05 mm³ or less, about 0.04 mm³ or less, about 0.03 mm³ or less, about 0.02 mm³ or less, or about 0.01 mm³.

In some embodiments, the bilayer tablet is configured to have a largest pore volume of about 0.84±0.5 mm³, about 0.84±0.45 mm³, about 0.84±0.4 mm³, about 0.84±0.35 mm³, about 0.84±0.3 mm³, about 0.84±0.25 mm³, about 0.84±0.2 mm³, about 0.84±0.15 mm³, about 0.84±0.1 mm³, about 0.84±0.09 mm³, about 0.84±0.08 mm³, about 0.84±0.07 mm³, about 0.84±0.06 mm³, about 0.84±0.05 mm³, about 0.84±0.04 mm³, about 0.84±0.03 mm³, about 0.84±0.02 mm³, or about 0.84±0.01 mm³.

In some embodiments, the bilayer tablet is configured to have a ratio between the largest pore volume and total pore volume of about 80% or less, about 70% or less, about 60% or less, about 50% or less, about 40% or less, about 30% or less, about 20% or less, about 19% or less, about 18% or less, about 17% or less, about 16% or less, about 15% or less, about 14% or less, about 13% or less, about 12% or less, about 11% or less, about 10% or less, about 9% or less, about 8% or less, about 7% or less, about 6% or less, about 5% or less, about 4% or less, about 3% or less, about 2% or less, or about 1% or less.

In some embodiments, the bilayer tablet is configured to have a ratio between the largest pore volume and total pore volume of about 10±9%, about 10±8%, about 10±7%, about 10±6%, about 10±5%, about 10±4.5%, about 10±4%, about 10±3.5%, about 10±3%, about 10±2.5%, about 10±2%, about 10±1.9%, about 10±1.8%, about 10±1.7%, about 10±1.6%, about 10±1.5%, about 10±1.4%, about 10±1.3%, about 10±1.2%, about 10±1.1%, about 10±1.0%, about 10±0.9%, about 10±0.8%, about 10±0.7%, about 10±0.6%, about 10±0.5%, about 10±0.4%, about 10±0.3%, about 10±0.2%, or about 10±0.1%.

Physicochemical Properties of the Bilayer Tablets

It is understood that the bilayer tablet of the present disclosure may have one or more of the physicochemical properties disclosed herein.

In Vitro Release of β-Lactam Compound or the Pharmaceutically Acceptable Salt Thereof In some embodiments, the bilayer tablet is configured to release about 40±20%, about 40±18%, about 40±16%, about 40±14%, about 40±12%, about 40±10%, about 40±9%, about 40±8%, about 40±7%, about 40±6%, about 40±5%, about 40±4%, about 40±3%, about 40±2%, or about 40±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 63±20%, about 63±18%, about 63±16%, about 63±14%, about 63±12%, about 63±10%, about 63±9%, about 63±8%, about 63±7%, about 63±6%, about 63±5%, about 63±4%, about 63±3%, about 63±2%, or about 63±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 74±10%, about 74±9%, about 74±8%, about 74±7%, about 74±6%, about 74±5%, about 74±4%, about 74±3%, about 74±2%, or about 74±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <711>-compliant test method).

In some embodiments, the bilayer tablet is configured to release about 80±10%, about 80±9%, about 80±8%, about 80±7%, about 80±6%, about 80±5%, about 80±4%, about 80±3%, about 80±2%, or about 80±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <711>-compliant test method).

In some embodiments, the bilayer tablet is configured to release about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 30 minutes as measured in vitro by a testing method described herein (e.g., the USP <711>-compliant test method).

In some embodiments, the bilayer tablet is configured to release about 91±5%, about 91±4%, about 91±3%, about 91±2%, or about 91±1% of the β-lactam compound (e.g., Compound III-2, Compound III-2a, or Compound III-2b) or the pharmaceutically acceptable salt thereof in the bilayer tablet within about 45 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 40±20%, about 40±18%, about 40±16%, about 40±14%, about 40±12%, about 40±10%, about 40±9%, about 40±8%, about 40±7%, about 40±6%, about 40±5%, about 40±4%, about 40±3%, about 40±2%, or about 40±1% of the β-lactam compound (e.g., Compound III-2, Compound III-2a, or Compound III-2b) or the pharmaceutically acceptable salt thereof in the bilayer tablet within about 5 minutes;

about 63±20%, about 63±18%, about 63±16%, about 63±14%, about 63±12%, about 63±10%, about 63±9%, about 63±8%, about 63±7%, about 63±6%, about 63±5%, about 63±4%, about 63±3%, about 63±2%, or about 63±1% of the β-lactam compound (e.g., Compound III-2, Compound III-2a, or Compound III-2b) or the pharmaceutically acceptable salt thereof in the bilayer tablet within about 10 minutes;

about 74±10%, about 74±9%, about 74±8%, about 74±7%, about 74±6%, about 74±5%, about 74±4%, about 74±3%, about 74±2%, or about 74±1% of the β-lactam compound (e.g., Compound III-2, Compound III-2a, or Compound III-2b) or the pharmaceutically acceptable salt thereof in the bilayer tablet within about 15 minutes;

about 80±10%, about 80±9%, about 80±8%, about 80±7%, about 80±6%, about 80±5%, about 80±4%, about 80±3%, about 80±2%, or about 80±1% of the β-lactam compound (e.g., Compound III-2, Compound III-2a, or Compound III-2b) or the pharmaceutically acceptable salt thereof in the bilayer tablet within about 20 minutes;

about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 30 minutes; and about 91±5%, about 91±4%, about 91±3%, about 91±2%, or about 91±1% of the β-lactam compound (e.g., Compound III-2, Compound III-2a, or Compound III-2b) or the pharmaceutically acceptable salt thereof in the bilayer tablet within about 45 minutes.

In some embodiments, the bilayer tablet is configured to release about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 71±20%, about 71±18%, about 71±16%, about 71±14%, about 71±12%, about 71±10%, about 71±9%, about 71±8%, about 71±7%, about 71±6%, about 71±5%, about 71±4%, about 71±3%, about 71±2%, or about 71±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 82±10%, about 82±9%, about 82±8%, about 82±7%, about 82±6%, about 82±5%, about 82±4%, about 82±3%, about 82±2%, or about 82±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <711>-compliant test method).

In some embodiments, the bilayer tablet is configured to release about 89±10%, about 89±9%, about 89±8%, about 89±7%, about 89±6%, about 89±5%, about 89±4%, about 89±3%, about 89±2%, or about 89±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <711>-compliant test method).

In some embodiments, the bilayer tablet is configured to release about 95±5%, about 95±4%, about 95±3%, about 95±2%, or about 95±1% of the β-lactam compound (e.g., Compound III-2, Compound III-2a, or Compound III-2b) or the pharmaceutically acceptable salt thereof in the bilayer tablet within about 30 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes;

about 71±20%, about 71±18%, about 71±16%, about 71±14%, about 71±12%, about 71±10%, about 71±9%, about 71±8%, about 71±7%, about 71±6%, about 71±5%, about 71±4%, about 71±3%, about 71±2%, or about 71±1% of the β-lactam compound (e.g., Compound III-2, Compound III-2a, or Compound III-2b) or the pharmaceutically acceptable salt thereof in the bilayer tablet within about 10 minutes;

about 82±10%, about 82±9%, about 82±8%, about 82±7%, about 82±6%, about 82±5%, about 82±4%, about 82±3%, about 82±2%, or about 82±1% of the β-lactam compound (e.g., Compound III-2, Compound III-2a, or Compound III-2b) or the pharmaceutically acceptable salt thereof in the bilayer tablet within about 15 minutes;

about 89±10%, about 89±9%, about 89±8%, about 89±7%, about 89±6%, about 89±5%, about 89±4%, about 89±3%, about 89±2%, or about 89±1% of the β-lactam compound (e.g., Compound III-2, Compound III-2a, or Compound III-2b) or the pharmaceutically acceptable salt thereof in the bilayer tablet within about 20 minutes; and about 95±5%, about 95±4%, about 95±3%, about 95±2%, or about 95±1% of the β-lactam compound (e.g., Compound III-2, Compound III-2a, or Compound III-2b) or the pharmaceutically acceptable salt thereof in the bilayer tablet within about 30 minutes.

In some embodiments, the bilayer tablet is configured to release about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <811>-compliant test method).

In some embodiments, the bilayer tablet is configured to release about 70±20%, about 70±18%, about 70±16%, about 70±14%, about 70±12%, about 70±10%, about 70±9%, about 70±8%, about 70±7%, about 70±6%, about 70±5%, about 70±4%, about 70±3%, about 70±2%, or about 70±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <811>-compliant test method).

In some embodiments, the bilayer tablet is configured to release about 81±10%, about 81±9%, about 81±8%, about 81±7%, about 81±6%, about 81±5%, about 81±4%, about 81±3%, about 81±2%, or about 81±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <811>-compliant test method).

In some embodiments, the bilayer tablet is configured to release about 87±10%, about 87±9%, about 87±8%, about 87±7%, about 87±6%, about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <811>-compliant test method).

In some embodiments, the bilayer tablet is configured to release about 93±5%, about 93±4%, about 93±3%, about 93±2%, or about 93±1% of the β-lactam compound (e.g., Compound III-2, Compound III-2a, or Compound III-2b) or the pharmaceutically acceptable salt thereof in the bilayer tablet within about 30 minutes as measured in vitro by a testing method described herein (e.g., the USP <811>-compliant test method).

In some embodiments, the bilayer tablet is configured to release, as measured in vitro by a testing method described herein (e.g., the USP <811>-compliant test method):

about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes;

about 70±20%, about 70±18%, about 70±16%, about 70±14%, about 70±12%, about 70±10%, about 70±9%, about 70±8%, about 70±7%, about 70±6%, about 70±5%, about 70±4%, about 70±3%, about 70±2%, or about 70±1% of the β-lactam compound (e.g., Compound III-2, Compound III-2a, or Compound III-2b) or the pharmaceutically acceptable salt thereof in the bilayer tablet within about 10 minutes;

about 81±10%, about 81±9%, about 81±8%, about 81±7%, about 81±6%, about 81±5%, about 81±4%, about 81±3%, about 81±2%, or about 81±1% of the β-lactam compound (e.g., Compound III-2, Compound III-2a, or Compound III-2b) or the pharmaceutically acceptable salt thereof in the bilayer tablet within about 15 minutes;

about 87±10%, about 87±9%, about 87±8%, about 87±7%, about 87±6%, about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 20 minutes; and about 93±5%, about 93±4%, about 93±3%, about 93±2%, or about 93±1% of the β-lactam compound (e.g., Compound III-2, Compound III-2a, or Compound III-2b) or the pharmaceutically acceptable salt thereof in the bilayer tablet within about 30 minutes.

In some embodiments, the bilayer tablet is configured to release about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 71±20%, about 71±18%, about 71±16%, about 71±14%, about 71±12%, about 71±10%, about 71±9%, about 71±8%, about 71±7%, about 71±6%, about 71±5%, about 71±4%, about 71±3%, about 71±2%, or about 71±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 84±10%, about 84±9%, about 84±8%, about 84±7%, about 84±6%, about 84±5%, about 84±4%, about 84±3%, about 84±2%, or about 84±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <711>-compliant test method).

In some embodiments, the bilayer tablet is configured to release about 92±10%, about 92±9%, about 92±8%, about 92±7%, about 92±6%, about 92±5%, about 92±4%, about 92±3%, about 92±2%, or about 92±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 47±20%, about 47±18%, about 47±16%, about 47±14%, about 47±12%, about 47±10%, about 47±9%, about 47±8%, about 47±7%, about 47±6%, about 47±5%, about 47±4%, about 47±3%, about 47±2%, or about 47±1% of the β-lactam compound (e.g., Compound III-2, Compound III-2a, or Compound III-2b) or the pharmaceutically acceptable salt thereof in the bilayer tablet within about 5 minutes;

about 71±20%, about 71±18%, about 71±16%, about 71±14%, about 71±12%, about 71±10%, about 71±9%, about 71±8%, about 71±7%, about 71±6%, about 71±5%, about 71±4%, about 71±3%, about 71±2%, or about 71±1% of the β-lactam compound (e.g., Compound III-2, Compound III-2a, or Compound III-2b) or the pharmaceutically acceptable salt thereof in the bilayer tablet within about 10 minutes;

about 84±10%, about 84±9%, about 84±8%, about 84±7%, about 84±6%, about 84±5%, about 84±4%, about 84±3%, about 84±2%, or about 84±1% of the β-lactam compound (e.g., Compound III-2, Compound III-2a, or Compound III-2b) or the pharmaceutically acceptable salt thereof in the bilayer tablet within about 15 minutes; and about 92±10%, about 92±9%, about 92±8%, about 92±7%, about 92±6%, about 92±5%, about 92±4%, about 92±3%, about 92±2%, or about 92±1% of the β-lactam compound (e.g., Compound III-2, Compound III-2a, or Compound III-2b) or the pharmaceutically acceptable salt thereof in the bilayer tablet within about 20 minutes.

In some embodiments, the bilayer tablet is configured to release about 52±20%, about 52±18%, about 52±16%, about 52±14%, about 52±12%, about 52±10%, about 52±9%, about 52±8%, about 52±7%, about 52±6%, about 52±5%, about 52±4%, about 52±3%, about 52±2%, or about 52±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 74±20%, about 74±18%, about 74±16%, about 74±14%, about 74±12%, about 74±10%, about 74±9%, about 74±8%, about 74±7%, about 74±6%, about 74±5%, about 74±4%, about 74±3%, about 74±2%, or about 74±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 84±10%, about 84±9%, about 84±8%, about 84±7%, about 84±6%, about 84±5%, about 84±4%, about 84±3%, about 84±2%, or about 84±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <711>-compliant test method).

In some embodiments, the bilayer tablet is configured to release about 89±10%, about 89±9%, about 89±8%, about 89±7%, about 89±6%, about 89±5%, about 89±4%, about 89±3%, about 89±2%, or about 89±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <711>-compliant test method).

In some embodiments, the bilayer tablet is configured to release about 95±5%, about 95±4%, about 95±3%, about 95±2%, or about 95±1% of the β-lactam compound (e.g., Compound III-2, Compound III-2a, or Compound III-2b) or the pharmaceutically acceptable salt thereof in the bilayer tablet within about 30 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 52±20%, about 52±18%, about 52±16%, about 52±14%, about 52±12%, about 52±10%, about 52±9%, about 52±8%, about 52±7%, about 52±6%, about 52±5%, about 52±4%, about 52±3%, about 52±2%, or about 52±1% of the β-lactam compound (e.g., Compound III-2, Compound III-2a, or Compound III-2b) or the pharmaceutically acceptable salt thereof in the bilayer tablet within about 5 minutes;

about 74±20%, about 74±18%, about 74±16%, about 74±14%, about 74±12%, about 74±10%, about 74±9%, about 74±8%, about 74±7%, about 74±6%, about 74±5%, about 74±4%, about 74±3%, about 74±2%, or about 74±1% of the β-lactam compound (e.g., Compound III-2, Compound III-2a, or Compound III-2b) or the pharmaceutically acceptable salt thereof in the bilayer tablet within about 10 minutes;

about 84±10%, about 84±9%, about 84±8%, about 84±7%, about 84±6%, about 84±5%, about 84±4%, about 84±3%, about 84±2%, or about 84±1% of the β-lactam compound (e.g., Compound III-2, Compound III-2a, or Compound III-2b) or the pharmaceutically acceptable salt thereof in the bilayer tablet within about 15 minutes;

about 89±10%, about 89±9%, about 89±8%, about 89±7%, about 89±6%, about 89±5%, about 89±4%, about 89±3%, about 89±2%, or about 89±1% of the β-lactam compound (e.g., Compound III-2, Compound III-2a, or Compound III-2b) or the pharmaceutically acceptable salt thereof in the bilayer tablet within about 20 minutes; and about 95±5%, about 95±4%, about 95±3%, about 95±2%, or about 95±1% of the β-lactam compound (e.g., Compound III-2, Compound III-2a, or Compound III-2b) or the pharmaceutically acceptable salt thereof in the bilayer tablet within about 30 minutes.

In some embodiments, the bilayer tablet is configured to release about 53±20%, about 53±18%, about 53±16%, about 53±14%, about 53±12%, about 53±10%, about 53±9%, about 53±8%, about 53±7%, about 53±6%, about 53±5%, about 53±4%, about 53±3%, about 53±2%, or about 53±1% of the β-lactam compound (e.g., Compound III-2, Compound III-2a, or Compound III-2b) or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 77±20%, about 77±18%, about 77±16%, about 77±14%, about 77±12%, about 77±10%, about 77±9%, about 77±8%, about 77±7%, about 77±6%, about 77±5%, about 77±4%, about 77±3%, about 77±2%, or about 77±1% of the β-lactam compound (e.g., Compound III-2, Compound III-2a, or Compound III-2b) or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 87±10%, about 87±9%, about 87±8%, about 87±7%, about 87±6%, about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 15 minutes as measured in vitro by a testing method described herein (e.g., the USP <711>-compliant test method).

In some embodiments, the bilayer tablet is configured to release about 93±5%, about 93±4%, about 93±3%, about 93±2%, or about 93±1% of the β-lactam compound (e.g., Compound III-2, Compound III-2a, or Compound III-2b) or the pharmaceutically acceptable salt thereof in the bilayer tablet within about 20 minutes as measured in vitro by a testing method described herein (e.g., the USP <711>-compliant test method).

In some embodiments, the bilayer tablet is configured to release about 98±2%, about 98±1.8%, about 98±1.6%, about 98±1.4%, about 98±1.2%, about 98±1%, about 98±0.9%, about 98±0.8%, about 98±0.7%, about 98±0.6%, about 98±0.5%, about 98±0.4%, about 98±0.3%, about 98±0.2%, or about 98±0.1% of the β-lactam compound (e.g., Compound III-2, Compound III-2a, or Compound III-2b) or the pharmaceutically acceptable salt thereof in the bilayer tablet within about 30 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 53±20%, about 53±18%, about 53±16%, about 53±14%, about 53±12%, about 53±10%, about 53±9%, about 53±8%, about 53±7%, about 53±6%, about 53±5%, about 53±4%, about 53±3%, about 53±2%, or about 53±1% of the β-lactam compound (e.g., Compound III-2, Compound III-2a, or Compound III-2b) or the pharmaceutically acceptable salt thereof in the bilayer tablet within about 5 minutes;

about 77±20%, about 77±18%, about 77±16%, about 77±14%, about 77±12%, about 77±10%, about 77±9%, about 77±8%, about 77±7%, about 77±6%, about 77±5%, about 77±4%, about 77±3%, about 77±2%, or about 77±1% of the β-lactam compound (e.g., Compound III-2, Compound III-2a, or Compound III-2b) or the pharmaceutically acceptable salt thereof in the bilayer tablet within about 10 minutes;

about 87±10%, about 87±9%, about 87±8%, about 87±7%, about 87±6%, about 87±5%, about 87±4%, about 87±3%, about 87±2%, or about 87±1% of the β-lactam compound (e.g., Compound III-2, Compound III-2a, or Compound III-2b) or the pharmaceutically acceptable salt thereof in the bilayer tablet within about 15 minutes;

about 93±5%, about 93±4%, about 93±3%, about 93±2%, or about 93±1% of the β-lactam compound (e.g., Compound III-2, Compound III-2a, or Compound III-2b) or the pharmaceutically acceptable salt thereof in the bilayer tablet within about 20 minutes; and about 98±2%, about 98±1.8%, about 98±1.6%, about 98±1.4%, about 98±1.2%, about 98±1%, about 98±0.9%, about 98±0.8%, about 98±0.7%, about 98±0.6%, about 98±0.5%, about 98±0.4%, about 98±0.3%, about 98±0.2%, or about 98±0.1% of the β-lactam compound (e.g., Compound III-2, Compound III-2a, or Compound III-2b) or the pharmaceutically acceptable salt thereof in the bilayer tablet within about 30 minutes.

In Vitro Release of Probenecid or the Pharmaceutically Acceptable Salt Thereof

In some embodiments, the bilayer tablet is configured to release about 25±20%, about 25±18%, about 25±16%, about 25±14%, about 25±12%, about 25±10%, about 25±9%, about 25±8%, about 25±7%, about 25±6%, about 25±5%, about 25±4%, about 25±3%, about 25±2%, or about 25±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 66±20%, about 66±18%, about 66±16%, about 66±14%, about 66±12%, about 66±10%, about 66±9%, about 66±8%, about 66±7%, about 66±6%, about 66±5%, about 66±4%, about 66±3%, about 66±2%, or about 66±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 92±20%, about 92±18%, about 92±16%, about 92±14%, about 92±12%, about 92±10%, about 92±9%, about 92±8%, about 92±7%, about 92±6%, about 92±5%, about 92±4%, about 92±3%, about 92±2%, or about 92±1% of probenecid or the pharmaceutically acceptable salt thereof in the bilayer tablet within about 15 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 25±10%, about 25±9%, about 25±8%, about 25±7%, about 25±6%, about 25±5%, about 25±4%, about 25±3%, about 25±2%, or about 25±1% of probenecid or the pharmaceutically acceptable salt thereof in the bilayer tablet within about 5 minutes;

about 66±10%, about 66±9%, about 66±8%, about 66±7%, about 66±6%, about 66±5%, about 66±4%, about 66±3%, about 66±2%, or about 66±1% of probenecid or the pharmaceutically acceptable salt thereof in the bilayer tablet within about 10 minutes; and about 92±2%, about 92±1.8%, about 92±1.6%, about 92±1.4%, about 92±1.2%, about 92±1%, about 92±0.9%, about 92±0.8%, about 92±0.7%, about 92±0.6%, about 92±0.5%, about 92±0.4%, about 92±0.3%, about 92±0.2%, or about 92±0.1% of probenecid or the pharmaceutically acceptable salt thereof in the bilayer tablet within about 15 minutes.

In some embodiments, the bilayer tablet is configured to release about 28±20%, about 28±18%, about 28±16%, about 28±14%, about 28±12%, about 28±10%, about 28±9%, about 28±8%, about 28±7%, about 28±6%, about 28±5%, about 28±4%, about 28±3%, about 28±2%, or about 28±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 71±20%, about 71±18%, about 71±16%, about 71±14%, about 71±12%, about 71±10%, about 71±9%, about 71±8%, about 71±7%, about 71±6%, about 71±5%, about 71±4%, about 71±3%, about 71±2%, or about 71±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 94±20%, about 94±18%, about 94±16%, about 94±14%, about 94±12%, about 94±10%, about 94±9%, about 94±8%, about 94±7%, about 94±6%, about 94±5%, about 94±4%, about 94±3%, about 94±2%, or about 94±1% of probenecid or the pharmaceutically acceptable salt thereof in the bilayer tablet within about 15 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 28±10%, about 28±9%, about 28±8%, about 28±7%, about 28±6%, about 28±5%, about 28±4%, about 28±3%, about 28±2%, or about 28±1% of probenecid or the pharmaceutically acceptable salt thereof in the bilayer tablet within about 5 minutes;

about 71±10%, about 71±9%, about 71±8%, about 71±7%, about 71±6%, about 71±5%, about 71±4%, about 71±3%, about 71±2%, or about 71±1% of probenecid or the pharmaceutically acceptable salt thereof in the bilayer tablet within about 10 minutes; and about 94±2%, about 94±1.8%, about 94±1.6%, about 94±1.4%, about 94±1.2%, about 94±1%, about 94±0.9%, about 94±0.8%, about 94±0.7%, about 94±0.6%, about 94±0.5%, about 94±0.4%, about 94±0.3%, about 94±0.2%, or about 94±0.1% of probenecid or the pharmaceutically acceptable salt thereof in the bilayer tablet within about 15 minutes.

In some embodiments, the bilayer tablet is configured to release about 30±20%, about 30±18%, about 30±16%, about 30±14%, about 30±12%, about 30±10%, about 30±9%, about 30±8%, about 30±7%, about 30±6%, about 30±5%, about 30±4%, about 30±3%, about 30±2%, or about 30±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 72±20%, about 72±18%, about 72±16%, about 72±14%, about 72±12%, about 72±10%, about 72±9%, about 72±8%, about 72±7%, about 72±6%, about 72±5%, about 72±4%, about 72±3%, about 72±2%, or about 72±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 94±20%, about 94±18%, about 94±16%, about 94±14%, about 94±12%, about 94±10%, about 94±9%, about 94±8%, about 94±7%, about 94±6%, about 94±5%, about 94±4%, about 94±3%, about 94±2%, or about 94±1% of probenecid or the pharmaceutically acceptable salt thereof in the bilayer tablet within about 15 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 30±10%, about 30±9%, about 30±8%, about 30±7%, about 30±6%, about 30±5%, about 30±4%, about 30±3%, about 30±2%, or about 30±1% of probenecid or the pharmaceutically acceptable salt thereof in the bilayer tablet within about 5 minutes;

about 72±10%, about 72±9%, about 72±8%, about 72±7%, about 72±6%, about 72±5%, about 72±4%, about 72±3%, about 72±2%, or about 72±1% of probenecid or the pharmaceutically acceptable salt thereof in the bilayer tablet within about 10 minutes; and about 94±2%, about 94±1.8%, about 94±1.6%, about 94±1.4%, about 94±1.2%, about 94±1%, about 94±0.9%, about 94±0.8%, about 94±0.7%, about 94±0.6%, about 94±0.5%, about 94±0.4%, about 94±0.3%, about 94±0.2%, or about 94±0.1% of probenecid or the pharmaceutically acceptable salt thereof in the bilayer tablet within about 15 minutes.

In some embodiments, the bilayer tablet is configured to release about 41±20%, about 41±18%, about 41±16%, about 41±14%, about 41±12%, about 41±10%, about 41±9%, about 41±8%, about 41±7%, about 41±6%, about 41±5%, about 41±4%, about 41±3%, about 41±2%, or about 41±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 87±20%, about 87±18%, about 87±16%, about 87±14%, about 87±12%, about 87±10%, about 87±9%, about 87±8%, about 87±7%, about 87±6%, about 87±5%, about 87±4%, about 87±3%, about 87±2%, or about 87±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 96±20%, about 96±18%, about 96±16%, about 96±14%, about 96±12%, about 96±10%, about 96±9%, about 96±8%, about 96±7%, about 96±6%, about 96±5%, about 96±4%, about 96±3%, about 96±2%, or about 96±1% of probenecid or the pharmaceutically acceptable salt thereof in the bilayer tablet within about 15 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 41±10%, about 41±9%, about 41±8%, about 41±7%, about 41±6%, about 41±5%, about 41±4%, about 41±3%, about 41±2%, or about 41±1% of probenecid or the pharmaceutically acceptable salt thereof in the bilayer tablet within about 5 minutes;

about 87±10%, about 87±9%, about 87±8%, about 87±7%, about 87±6%, about 87±5%, about 87±4%, about 87±3%, about 87±2%, or about 87±1% of probenecid or the pharmaceutically acceptable salt thereof in the bilayer tablet within about 10 minutes; and about 96±2%, about 96±1.8%, about 96±1.6%, about 96±1.4%, about 96±1.2%, about 96±1%, about 96±0.9%, about 96±0.8%, about 96±0.7%, about 96±0.6%, about 96±0.5%, about 96±0.4%, about 96±0.3%, about 96±0.2%, or about 96±0.1% of probenecid or the pharmaceutically acceptable salt thereof in the bilayer tablet within about 15 minutes.

In some embodiments, the bilayer tablet is configured to release about 43±20%, about 43±18%, about 43±16%, about 43±14%, about 43±12%, about 43±10%, about 43±9%, about 43±8%, about 43±7%, about 43±6%, about 43±5%, about 43±4%, about 43±3%, about 43±2%, or about 43±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release about 86±20%, about 86±18%, about 86±16%, about 86±14%, about 86±12%, about 86±10%, about 86±9%, about 86±8%, about 86±7%, about 86±6%, about 86±5%, about 86±4%, about 86±3%, about 86±2%, or about 86±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 98±20%, about 98±18%, about 98±16%, about 98±14%, about 98±12%, about 98±10%, about 98±9%, about 98±8%, about 98±7%, about 98±6%, about 98±5%, about 98±4%, about 98±3%, about 98±2%, or about 98±1% of probenecid or the pharmaceutically acceptable salt thereof in the bilayer tablet within about 15 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 43±10%, about 43±9%, about 43±8%, about 43±7%, about 43±6%, about 43±5%, about 43±4%, about 43±3%, about 43±2%, or about 43±1% of probenecid or the pharmaceutically acceptable salt thereof in the bilayer tablet within about 5 minutes;

about 86±10%, about 86±9%, about 86±8%, about 86±7%, about 86±6%, about 86±5%, about 86±4%, about 86±3%, about 86±2%, or about 86±1% of probenecid or the pharmaceutically acceptable salt thereof in the bilayer tablet within about 10 minutes; and about 98±2%, about 98±1.8%, about 98±1.6%, about 98±1.4%, about 98±1.2%, about 98±1%, about 98±0.9%, about 98±0.8%, about 98±0.7%, about 98±0.6%, about 98±0.5%, about 98±0.4%, about 98±0.3%, about 98±0.2%, or about 98±0.1% of probenecid or the pharmaceutically acceptable salt thereof in the bilayer tablet within about 15 minutes.

In some embodiments, the bilayer tablet is configured to release about 75±20%, about 75±18%, about 75±16%, about 75±14%, about 75±12%, about 75±10%, about 75±9%, about 75±8%, about 75±7%, about 75±6%, about 75±5%, about 75±4%, about 75±3%, about 75±2%, or about 75±1% of probenecid or the pharmaceutically acceptable salt thereof in the bilayer tablet within about 10 minutes as measured in vitro by a testing method described herein (e.g., the USP <711>-compliant test method).

In some embodiments, the bilayer tablet is configured to release about 37±20%, about 37±18%, about 37±16%, about 37±14%, about 37±12%, about 37±10%, about 37±9%, about 37±8%, about 37±7%, about 37±6%, about 37±5%, about 37±4%, about 37±3%, about 37±2%, or about 37±1% of probenecid or the pharmaceutically acceptable salt thereof in the bilayer tablet within about 5 minutes as measured in vitro by a testing method described herein (e.g., the USP <711>-compliant test method).

In some embodiments, the bilayer tablet is configured to release, as measured in vitro by a testing method described herein (e.g., the USP <711>-compliant test method):

about 37±10%, about 37±9%, about 37±8%, about 37±7%, about 37±6%, about 37±5%, about 37±4%, about 37±3%, about 37±2%, or about 37±1% of probenecid or the pharmaceutically acceptable salt thereof in the bilayer tablet within about 5 minutes;

about 75±10%, about 75±9%, about 75±8%, about 75±7%, about 75±6%, about 75±5%, about 75±4%, about 75±3%, about 75±2%, or about 75±1% of probenecid or the pharmaceutically acceptable salt thereof in the bilayer tablet within about 10 minutes; and about 96±2%, about 96±1.8%, about 96±1.6%, about 96±1.4%, about 96±1.2%, about 96±1%, about 96±0.9%, about 96±0.8%, about 96±0.7%, about 96±0.6%, about 96±0.5%, about 96±0.4%, about 96±0.3%, about 96±0.2%, or about 96±0.1% of probenecid or the pharmaceutically acceptable salt thereof in the bilayer tablet within about 15 minutes.

Testing Methods for Physicochemical Properties of Bilayer Tablets

It is understood that the physicochemical properties (e.g., in vitro release characteristics of the bilayer tablet may be measured in vitro by using methods common in the art, e.g., the USP<711>-compliant testing method.

In some embodiments, the USP <711>-compliant method is carried out with a paddle apparatus, a basket apparatus, a reciprocating cylinder, or a flow-through cell as described in the method.

In some embodiments, the USP <711>-compliant method is carried out with a paddle apparatus as described in the method.

In some embodiments, the USP <711>-compliant method is carried out with a temperature of about 37±10° C., about 37±8° C., about 37±6° C., about 37±5° C., about 37±4° C., about 37±3° C., about 37±2° C., about 37±1° C., or about 37±0.5° C. In some embodiments, the method is the USP <711>-compliant method is carried out with a temperature at about 37° C.

In some embodiments, the USP <711>-compliant method is carried out with a sampling volume of about 2.5±2 mL, about 2.5±1.8 mL, about 2.5±1.6 mL, about 2.5±1.4 mL, about 2.5±1.2 mL, about 2.5±1 mL, about 2.5±0.9 mL, about 2.5±0.8 mL, about 2.5±0.7 mL, about 2.5±0.6 mL, about 2.5±0.5 mL, about 2.5±0.4 mL, about 2.5±0.3 mL, about 2.5±0.2 mL, or about 2.5±0.1 mL. In some embodiments, the USP <711>-compliant method is carried out with a sampling volume of about 2.5 mL.

In some embodiments, the USP <711>-compliant method is carried out with a rotation speed of about 75±50 rpm, about 75±40 rpm, about 75±30 rpm, about 75±20 rpm, about 75±15 rpm, about 75±10 rpm, or about 75±5 rpm. In some embodiments, the USP <711>-compliant method is carried out with a rotation speed of about 75 rpm.

In some embodiments, the USP <711>-compliant method is carried out with a media volume of about 900±500 mL, about 900±450 mL, about 900±400 mL, about 900±350 mL, about 900±300 mL, about 900±250 mL, about 900±200 mL, about 900±150 mL, about 900±100 mL, about 900±90 mL, about 900±80 mL, about 900±70 mL, about 900±60 mL, about 900±50 mL, about 900±40 mL, about 900±30 mL, about 900±20 mL, or about 900±10 mL. In some embodiments, the USP <711>-compliant method is carried out with a media volume of about 900 mL.

In some embodiments, the USP <711>-compliant method is carried out with a pH value of about 6.8±3, about 6.8±2.8, about 6.8±2.6, about 6.8±2.4, about 6.8±2.2, about 6.8±2, about 6.8±1.8, about 6.8±1.6, about 6.8±1.4, about 6.8±1.2, about 6.8±1, about 6.8±0.9, about 6.8±0.8, about 6.8±0.7, about 6.8±0.6, about 6.8±0.5, about 6.8±0.4, about 6.8±0.3, about 6.8±0.2, or about 6.8±0.1. In some embodiments, the USP <711>-compliant method is carried out with a pH value of about 6.8.

In some embodiments, the USP <711>-compliant method is carried out with analysis by HPLC (e.g., HPLC-UV).

β-Lactam Compounds

In some embodiments, the β-lactam compound is a monobactam or a prodrug thereof.

In some embodiments, the β-lactam compound is aztreonam, tigemonam, carumonam, nocardicin A, a prodrug thereof, an analog thereof, or a derivative thereof.

In some embodiments, the β-lactam compound is a penem, a carbapenem, a clavam, or a prodrug thereof.

In some embodiments, the β-lactam compound is benzylpenicillin, benzathine benzylpenicillin, procaine benzylpenicillin, phenoxymethylpenicillin, propicillin, pheneticillin, azidocillin, clometocillin, penamecillin, cloxacillin (e.g., dicloxacillin or flucloxacillin), oxacillin, nafcillin, methicillin, amoxicillin, ampicillin (e.g., pivampicillin, hetacillin, bacampicillin, metampicillin, talampicillin), epicillin, ticarcillin, carbenicillin, carindacillin, temocillin, piperacillin, azlocillin, mezlocillin, mecillinam (e.g., pivmecillinam), sulbenicillin, a pharmaceutically acceptable salt thereof, a prodrug thereof, an analog thereof, or a derivative thereof.

In some embodiments, the β-lactam compound is a penem, a carbapenem, or a prodrug thereof.

In some embodiments, the β-lactam compound is a thiopenem, an oxypenem, an aminopenem, an alkylpenems, an arylpenem, or a prodrug thereof.

In some embodiments, the β-lactam compound is ertapenem, an antipseudomonal carbapenem (e.g., doripenem, imipenem, meropenem), biapenem, panipenem, sulopenem, tebipenem, faropenem, a pharmaceutically acceptable salt thereof, a prodrug thereof, an analog thereof, or a derivative thereof.

In some embodiments, the β-lactam compound is a cephem, a carbacephem, an oxacephem, or a prodrug thereof.

In some embodiments, the β-lactam compound is cefazolin, cefalexin, cefadroxil, cefapirin, cefazedone, cefazaflur, cefradine, cefroxadine, ceftezole, cefaloglycin, cefacetrile, cefalonium, cefaloridine, cefalotin, cefatrizine, cefaclor, cefotetan, cephamycin (e.g., cefoxitin, cefprozil, cefuroxime, cefuroxime axetil, cefamandole, cefminox, cefonicid, ceforanide, cefotiam, cefbuperazone, cefuzonam, cefmetazole), carbacephem (e.g., loracarbef), cefixime, ceftriaxone, antipseudomonal (e.g, ceftazidime, cefoperazone), cefdinir, cefcapene, cefdaloxime, ceftizoxime, cefmenoxime, cefotaxime, cefpiramide, cefpodoxime, ceftibuten, cefditoren, cefetamet, cefodizime, cefpimizole, cefsulodin, cefteram, ceftiolene, oxacephem (e.g., flomoxef, latamoxef), cefepime, cefozopran, cefpirome, cefquinome, ceftaroline fosamil, ceftolozane, ceftobiprole, ceftiofur, cefquinome, cefovecin, a pharmaceutically acceptable salt thereof, a prodrug thereof, an analog thereof, or a derivative thereof.

In some embodiments, the β-lactam compound is a thiopenem or a prodrug thereof.

In some embodiments, the β-lactam compound is of Formula (I):

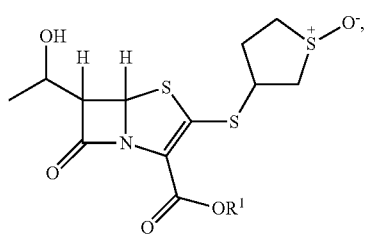

(I)

a pharmaceutically acceptable salt thereof, a prodrug thereof, an analog thereof, or a derivative thereof, wherein R¹ is H or optionally substituted alkyl.

In some embodiments, the β-lactam compound is of Formula (Ia):

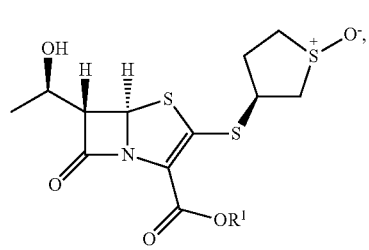

(Ia)

a pharmaceutically acceptable salt thereof, a prodrug thereof, an analog thereof, or a derivative thereof.

In some embodiments, the β-lactam compound is of Formula (Ib):

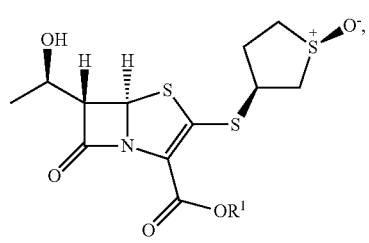

(Ib)

a pharmaceutically acceptable salt thereof, a prodrug thereof, an analog thereof, or a derivative thereof.

In some embodiments, R¹ is H.

In some embodiments, the β-lactam compound is of Formula (II):

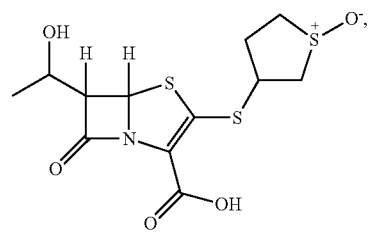

(II)

a pharmaceutically acceptable salt thereof, a prodrug thereof, an analog thereof, or a derivative thereof.

In some embodiments, the β-lactam compound is of Formula (IIa):

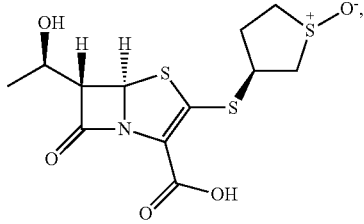
(IIa)

a pharmaceutically acceptable salt thereof, a prodrug thereof, an analog thereof, or a derivative thereof.

In some embodiments, the β-lactam compound is of Formula (IIb):

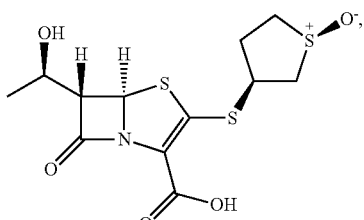
(IIb)

a pharmaceutically acceptable salt thereof, a prodrug thereof, an analog thereof, or a derivative thereof.

In some embodiments, $R^1$ is optionally substituted alkyl.

In some embodiments, the β-lactam compound is of any one of Formulae (III), (IIIa), and (IIIb):

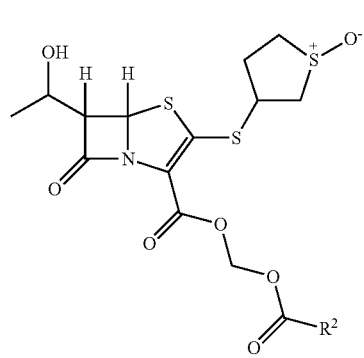
(III)

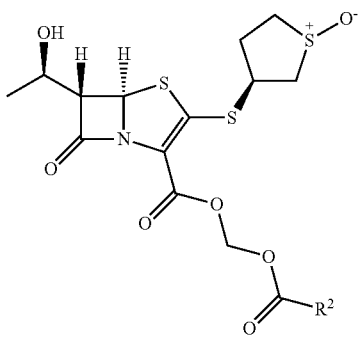
(IIIa)

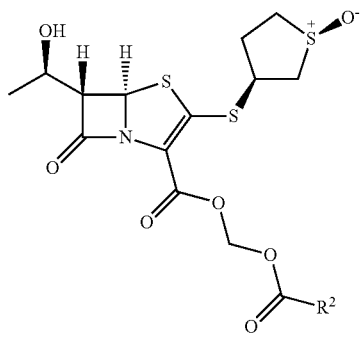
(IIIb)

a pharmaceutically acceptable salt thereof, a prodrug thereof, an analog thereof, or a derivative thereof, wherein $R^2$ is H or optionally substituted alkyl.

In some embodiments, the β-lactam compound is selected from the group consisting of:

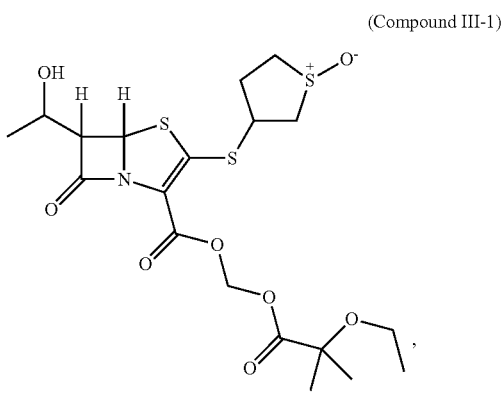
(Compound III-1)

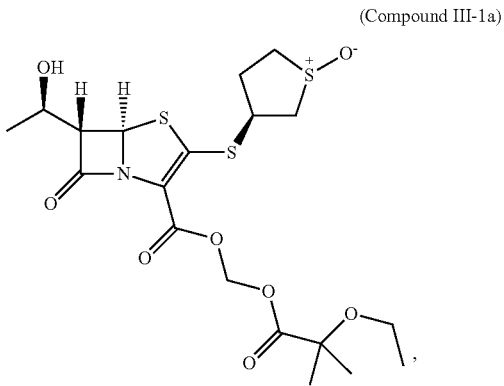
(Compound III-1a)

(Compound III-1b)

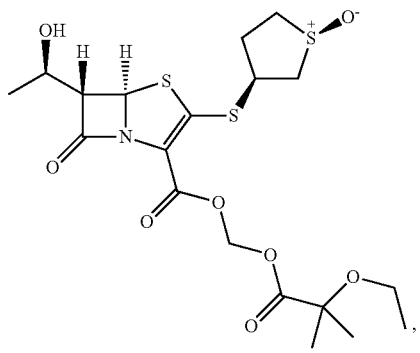

(Compound III-2b)

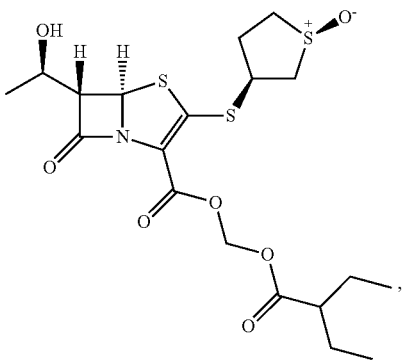

pharmaceutically acceptable salts thereof, prodrugs thereof, analogs thereof, and derivatives thereof.

In some embodiments, the β-lactam compound is selected from the group consisting of:

(Compound III-2)

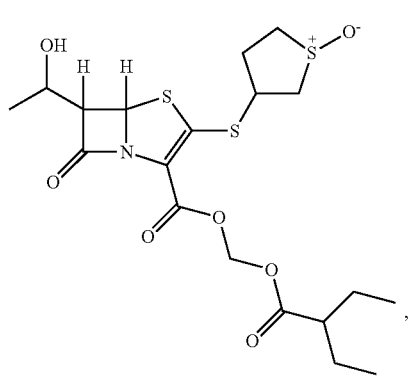

pharmaceutically acceptable salts thereof, prodrugs thereof, analogs thereof, and derivatives thereof.

In some embodiments, the β-lactam compound is selected from (Compound III-2b; also known as Sulopenem Etzadroxil)

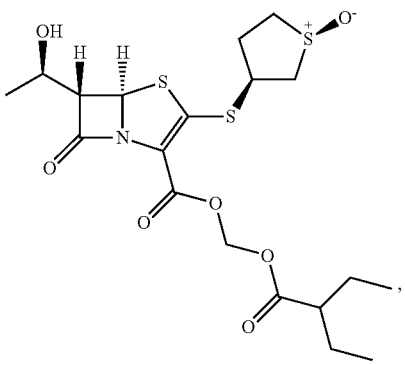

pharmaceutically acceptable salts thereof, prodrugs thereof, analogs thereof, and derivatives thereof.

Compounds of the present disclosure that contain nitrogens In some embodiments, the β-lactam compound is of any one of Formulae (IV), (IVa), and (IVb):

(Compound III-2a)

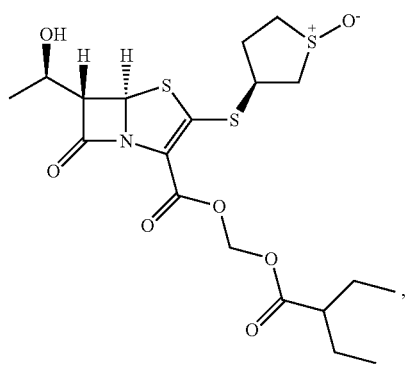

(IV)

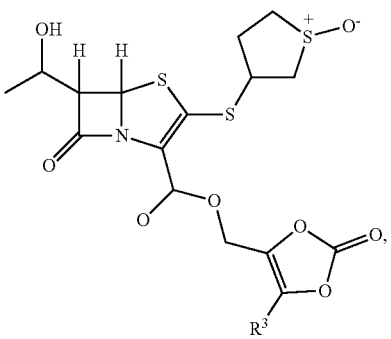

-continued

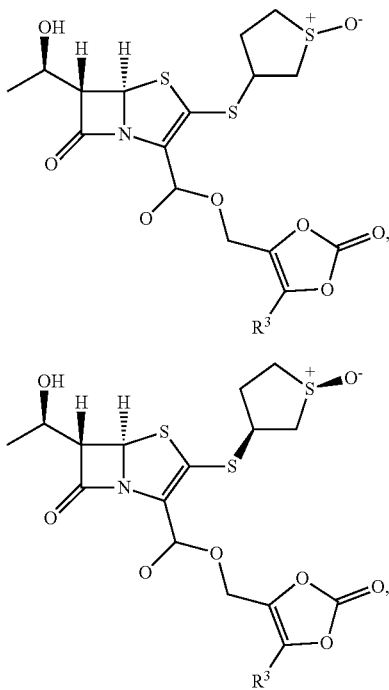

a pharmaceutically acceptable salt thereof, a prodrug thereof, an analog thereof, or a derivative thereof, wherein $R^3$ is H or optionally substituted alkyl.

In some embodiments, $R^3$ is $C_2$-$C_8$ alkyl.

In some embodiments, $R^3$ is $CH_2CH_3$, $CH_2CH_2CH_3$, or $CH_2CH(CH_3)_2$.

Methods of Preparation

In some aspects, the present disclosure provides a method of preparing a bilayer tablet.

In some embodiments, the bilayer tablet of the present disclosure is prepared by a method disclosed herein.

In some embodiments, the method comprises:

i) compressing a first granular material comprising probenecid or a pharmaceutically acceptable salt thereof with a first force, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force, thereby forming a pre-coated bilayer tablet.

In some embodiments, the first granular material is prepared by a process disclosed herein (e.g., the process as described in FIG. 1). In some embodiments, the first granular material is prepared by granulating a mixture of powdery or solid probenecid or the pharmaceutically acceptable salt thereof and one or more excipients.

Figure 2:
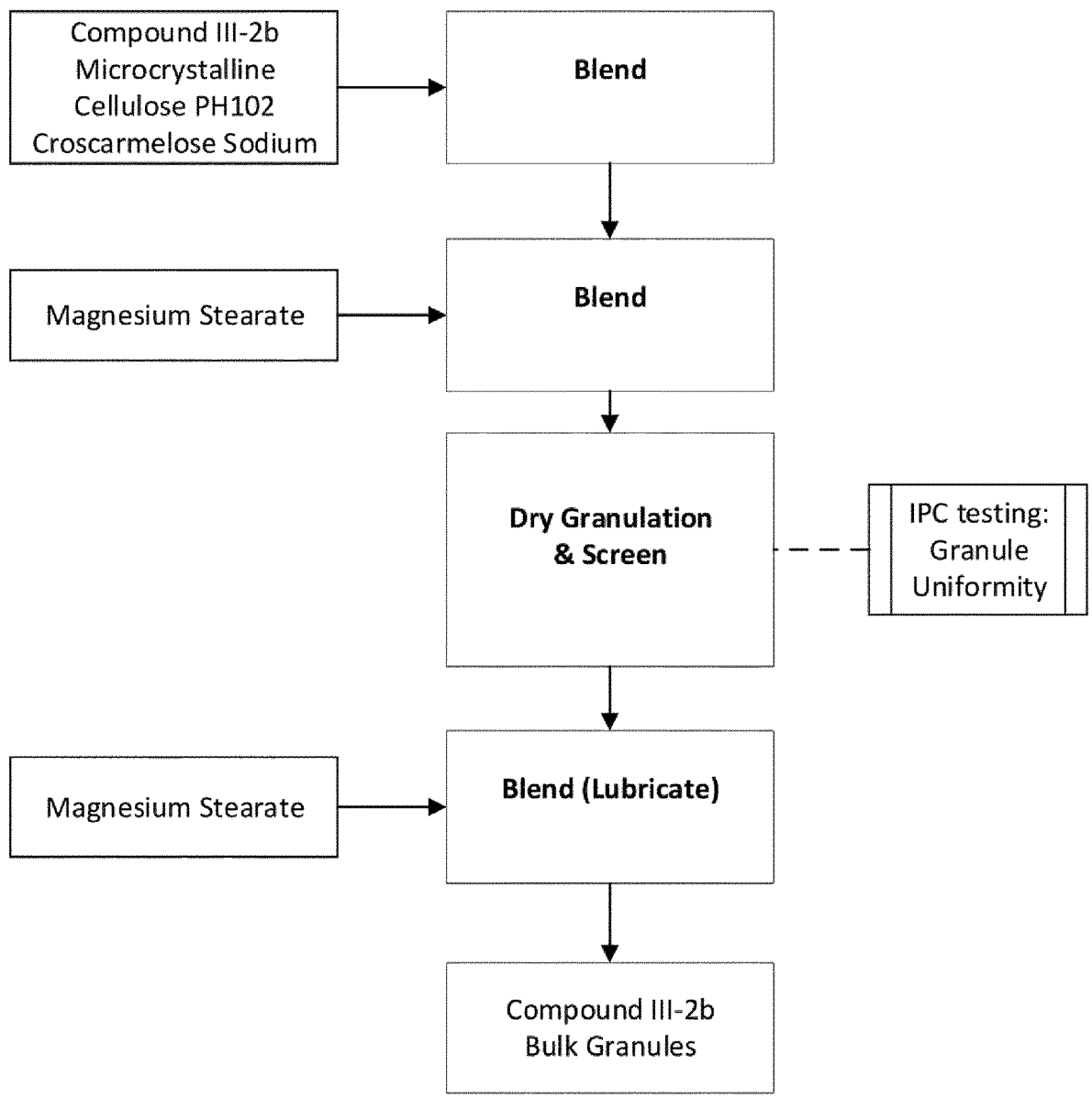
FIG. 2 is a diagram describing an exemplary process of preparing the granular material of Compound III-2b.

In some embodiments, the second granular material is prepared by a process disclosed herein (e.g., the process as described in FIG. 2).

In some embodiments, the second granular material is prepared by granulating a mixture of powdery or solid β-lactam compound or the pharmaceutically acceptable salt thereof (e.g., Compound III-2b) and one or more excipients.

In some embodiments, the granulated mixture is further compacted (e.g., by one or more roller compactions), thereby forming a compacted ribbon section.

In some embodiments, the compacted ribbon section is further granulated, crushed, and/or screened through one or more suitable size screens.

In some embodiments, the compaction step and the granulation, crushing, and/or screening step are repeated for one or more times.

In some embodiments, the first force is about 20 kN or less, about 19 kN or less, about 18 kN or less, about 17 kN or less, about 16 kN or less, about 15 kN or less, about 14.5 kN or less, about 14 kN or less, about 13.5 kN or less, about 13 kN or less, about 12.5 kN or less, about 12 kN or less, about 11.5 kN or less, about 11 kN or less, about 10.5 kN or less, about 10 kN or less, about 9.5 kN or less, about 9 kN or less, about 8.5 kN or less, about 8 kN or less, about 7.5 kN or less, about 7 kN or less, about 6.5 kN or less, about 6 kN or less, about 5.5 kN or less, about 5 kN or less, about 4.5 kN or less, about 4 kN or less, about 3.5 kN or less, about 3 kN or less, about 2.5 kN or less, about 2 kN or less, about 1.5 kN or less, about 1 kN or less, or about 0.5 kN or less.

In some embodiments, the first force is about 11.5 kN or less.

In some embodiments, the second force is about 50 kN or less, about 45 kN or less, about 40 kN or less, about 39 kN or less, about 38 kN or less, about 37 kN or less, about 36 kN or less, about 35 kN or less, about 34 kN or less, about 33 kN or less, about 32 kN or less, about 31 kN or less, about 30 kN or less, about 29 kN or less, about 28 kN or less, about 27 kN or less, about 26 kN or less, about 25 kN or less, about 20 kN or less, about 15 kN or less, about 10 kN or less, about 9 kN or less, about 8 kN or less, about 7 kN or less, about 6 kN or less, about 5 kN or less, about 4 kN or less, about 3 kN or less, about 2 kN or less, about 1 kN or less.

In some embodiments, the second force is about 30 kN or less.

In some embodiments, the first force is about 11.5 kN or less, and the second force is about 30 kN or less.

In some embodiments, the method comprises:

i) compressing a first granular material comprising probenecid or a pharmaceutically acceptable salt thereof with a first force being about 20 kN or less, about 19 kN or less, about 18 kN or less, about 17 kN or less, about 16 kN or less, about 15 kN or less, about 14.5 kN or less, about 14 kN or less, about 13.5 kN or less, about 13 kN or less, about 12.5 kN or less, about 12 kN or less, about 11.5 kN or less, about 11 kN or less, about 10.5 kN or less, about 10 kN or less, about 9.5 kN or less, about 9 kN or less, about 8.5 kN or less, about 8 kN or less, about 7.5 kN or less, about 7 kN or less, about 6.5 kN or less, about 6 kN or less, about 5.5 kN or less, about 5 kN or less, about 4.5 kN or less, about 4 kN or less, about 3.5 kN or less, about 3 kN or less, about 2.5 kN or less, about 2 kN or less, about 1.5 kN or less, or about 1 kN or less, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 50 kN or less, about 45 kN or less, about 40 kN or less, about 39 kN or less, about 38 kN or less, about 37 kN or less, about 36 kN or less, about 35 kN or less, about 34 kN or less, about 33 kN or less, about 32 kN or less, about 31 kN or less, about 30 kN or less, about 29 kN or less, about 28 kN or less, about 27 kN or less, about 26 kN or less, about 25 kN or less, about 20 kN or less, about 15 kN or less, about 10 kN or less, about 9 kN or less, about 8 kN or less, about 7 kN or less, about 6 kN or less, about 5 kN or less, about 4 kN or less, about 3 kN or less, about 2 kN or less, about 1 kN or less, thereby forming a pre-coated bilayer tablet.

In some embodiments, the method comprises:

i) compressing a first granular material comprising probenecid or a pharmaceutically acceptable salt thereof with a first force being about 11.5 kN or less, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 30 kN or less, thereby forming a pre-coated bilayer tablet.

In some embodiments, the first force is about 1.5±1.2 kN, about 1.5±1.1 kN, about 1.5±1.0 kN, about 1.5±0.9 kN, about 1.5±0.8 kN, about 1.5±0.75 kN, about 1.5±0.7 kN, about 1.5±0.65 kN, about 1.5±0.6 kN, about 1.5±0.55 kN, about 1.5±0.5 kN, about 1.5±0.45 kN, about 1.5±0.4 kN, about 1.5±0.35 kN, about 1.5±0.3 kN, about 1.5±0.25 kN, about 1.5±0.2 kN, about 1.5±0.15 kN, about 1.5±0.1 kN, or about 1.5±0.05 kN.

In some embodiments, the first force is about 1.5 kN.

In some embodiments, the first force is about 0.5±0.45 kN, about 0.5±0.4 kN, about 0.5±0.35 kN, about 0.5±0.3 kN, about 0.5±0.25 kN, about 0.5±0.2 kN, about 0.5±0.15 kN, about 0.5±0.1 kN, or about 0.5±0.05 kN.

In some embodiments, the first force is about 0.5 kN.

In some embodiments, the second force is about 11.5±10 kN, about 11.5±9 kN, about 11.5±8 kN, about 11.5±7 kN, about 11.5±6 kN, about 11.5±5 kN, about 11.5±4 kN, about 11.5±3 kN, about 11.5±2 kN, about 11.5±1 kN, about 11.5±0.9 kN, about 11.5±0.8 kN, about 11.5±0.7 kN, about 11.5±0.6 kN, about 11.5±0.5 kN, about 11.5±0.4 kN, about 11.5±0.3 kN, about 11.5±0.2 kN, or about 11.5±0.1 kN.

In some embodiments, the second force is about 11.5 kN.

In some embodiments, the first force is about 1.5 kN, and the second force is about 30 kN.

In some embodiments, the method comprises:

i) compressing a first granular material comprising probenecid or a pharmaceutically acceptable salt thereof with a first force being about 1.5±1.2 kN, about 1.5±1.1 kN, about 1.5±1.0 kN, about 1.5±0.9 kN, about 1.5±0.8 kN, about 1.5±0.75 kN, about 1.5±0.7 kN, about 1.5±0.65 kN, about 1.5±0.6 kN, about 1.5±0.55 kN, about 1.5±0.5 kN, about 1.5±0.45 kN, about 1.5±0.4 kN, about 1.5±0.35 kN, about 1.5±0.3 kN, about 1.5±0.25 kN, about 1.5±0.2 kN, about 1.5±0.15 kN, about 1.5±0.1 kN, or about 1.5±0.05 kN, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 11.5±10 kN, about 11.5±9 kN, about 11.5±8 kN, about 11.5±7 kN, about 11.5±6 kN, about 11.5±5 kN, about 11.5±4 kN, about 11.5±3 kN, about 11.5±2 kN, about 11.5±1 kN, about 11.5±0.9 kN, about 11.5±0.8 kN, about 11.5±0.7 kN, about 11.5±0.6 kN, about 11.5±0.5 kN, about 11.5±0.4 kN, about 11.5±0.3 kN, about 11.5±0.2 kN, or about 11.5±0.1 kN, thereby forming a pre-coated bilayer tablet.

In some embodiments, the method comprises:

i) compressing a first granular material comprising probenecid or a pharmaceutically acceptable salt thereof with a first force being about 1.5 kN, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 11.5 kN, thereby forming a pre-coated bilayer tablet.

In some embodiments, the first force is about 1.25±1.2 kN, about 1.25±1.1 kN, about 1.25±1.0 kN, about 1.25±0.9 kN, about 1.25±0.8 kN, about 1.25±0.75 kN, about 1.25±0.7 kN, about 1.25±0.65 kN, about 1.25±0.6 kN, about 1.25±0.55 kN, about 1.25±0.5 kN, about 1.25±0.45 kN, about 1.25±0.4 kN, about 1.25±0.35 kN, about 1.25±0.3 kN, about 1.25±0.25 kN, about 1.25±0.2 kN, about 1.25±0.15 kN, about 1.25±0.1 kN, or about 1.25±0.05 kN.

In some embodiments, the first force is about 1.25 kN.

In some embodiments, the second force is about 30±20 kN, about 30±15 kN, about 30±10 kN, about 30±9 kN, about 30±8 kN, about 30±7 kN, about 30±6 kN, about 30±5 kN, about 30±4 kN, about 30±3 kN, about 30±2 kN, about 30±1 kN, about 30±0.9 kN, about 30±0.8 kN, about 30±0.7 kN, about 30±0.6 kN, about 30±0.5 kN, about 30±0.4 kN, about 30±0.3 kN, about 30±0.2 kN, or about 30±0.1 kN.

In some embodiments, the second force is about 30 kN.

In some embodiments, the first force is about 1.25 kN, and the second force is about 30 kN.

In some embodiments, the method comprises:

i) compressing a first granular material comprising probenecid or a pharmaceutically acceptable salt thereof with a first force being about 1.25±1.2 kN, about 1.25±1.1 kN, about 1.25±1.0 kN, about 1.25±0.9 kN, about 1.25±0.8 kN, about 1.25±0.75 kN, about 1.25±0.7 kN, about 1.25±0.65 kN, about 1.25±0.6 kN, about 1.25±0.55 kN, about 1.25±0.5 kN, about 1.25±0.45 kN, about 1.25±0.4 kN, about 1.25±0.35 kN, about 1.25±0.3 kN, about 1.25±0.25 kN, about 1.25±0.2 kN, about 1.25±0.15 kN, about 1.25±0.1 kN, or about 1.25±0.05 kN, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 30±20 kN, about 30±15 kN, about 30±10 kN, about 30±9 kN, about 30±8 kN, about 30±7 kN, about 30±6 kN, about 30±5 kN, about 30±4 kN, about 30±3 kN, about 30±2 kN, about 30±1 kN, about 30±0.9 kN, about 30±0.8 kN, about 30±0.7 kN, about 30±0.6 kN, about 30±0.5 kN, about 30±0.4 kN, about 30±0.3 kN, about 30±0.2 kN, or about 30±0.1 kN, thereby forming a pre-coated bilayer tablet.

In some embodiments, the method comprises:

i) compressing a first granular material comprising probenecid or a pharmaceutically acceptable salt thereof with a first force being about 1.25 kN, thereby forming a pre-compressed first layer;

ii) adding a second granular material comprising a β-lactam compound or a pharmaceutically acceptable salt thereof to the pre-compressed first layer;

iii) compressing the pre-compressed first layer and the second granular material with a second force being about 30 kN, thereby forming a pre-coated bilayer tablet.

In some embodiments, the method further comprises:

iv) coating the pre-coated bilayer tablet with a coating agent, thereby forming the bilayer tablet.

In some embodiments, the coating agent comprises polyvinyl alcohol (PVA).

In some embodiments, the coating agent is free of polyethelyne glycol (PEG) or soy lecithin.

In some embodiments, the coating agent is Opadry® AMB White 80W68912.

In some embodiments, the coating agent is Opadry AMB Pink 80W240026

Methods of Use

In some aspects, the present disclosure provides a method of treating or preventing a disease, comprising administering to a subject in need thereof a pharmaceutically effective amount of a bilayer tablet disclosed herein.

In some aspects, the present disclosure provides a bilayer tablet disclosed herein for use in treating or preventing a disease in a subject in need thereof.

Treated Subjects and Diseases

In some embodiments, the subject in need thereof is an animal. In some embodiments, the subject in need thereof is a human.

In some embodiments, the subject in need thereof is a human of 18 years or older.

In some embodiments, the subject in need thereof is a human younger than 18 years.

In some embodiments, the disease is associated with an increased or decreased population of one or more microorganisms (e.g., bacteria) in the subject.

In some embodiments, the disease is associated with an increased population of one or more microorganisms (e.g., bacteria) in the subject. In some embodiments, the method of the present disclosure results in a decrease population of the one or more microorganisms (e.g., bacteria) in the subject.

In some embodiments, the disease is associated with a decreased population of one or more microorganisms (e.g., bacteria) in the subject. In some embodiments, the method of the present disclosure results in an increased population of the one or more microorganisms (e.g., bacteria) in the subject.

In some embodiments, the disease is associated with an increased or decreased population of one or more bacteria selected from *Escherichia coli, Klebsiella pneumoniae, Proteus mirabilis, Enterobacter cloacae, Klebsiella oxytoca, Citrobacter freundii* complex, *Clostridium clostridioforme, Eubacterium lentum, Peptostreptococcus* species, *Bacteroides fragilis, Bacteroides distasonis, Bacteroides ovatus, Bacteroides thetaiotaomicron, Bacteroides uniformis, Bacteroides coprocola, Prevotella copri, Porphyromonas asaccharolytica,* and *Prevotella bivia* or any organisms in the following genera: *Succinivibrio, Alistipes, Prevotella, Paraprevotella, Parabacteroides,* and *Odoribacter.*

In some embodiments, the disease is associated with an increased or decreased population of one or more bacteria selected from *Staphylococcus epidermidis, Streptococcus pneumonia, Staphylococcus aureus, Streptococcus agalactiae,* and *Streptococcus pyogenes.*

In some embodiments, the disease is associated with an increased or decreased population of one or more bacteria selected from *Citrobacter freundii, Citrobacter koseri, Enterobacter aerogenes, Enterobacter cloacae, Haemophilus influenza, Haemophilus parainfluenzae, Klebsiella oxytoca, Moraxella catarrhalis, Morganella morganii, Proteus vulgaris, Providencia rettgeri, Providencia stuartii,* and *Serratia marcescens.*

In some embodiments, the disease is associated with an increased or decreased population of one or more bacteria selected from *Bacteroides vulgatus, Clostridium perfringens,* and *Fusobacterium* spp.

In some embodiments, the disease is associated with an infection. In some embodiments, the infection is a gram-negative infection. In some embodiments, the infection is a gram-positive infection.

In some embodiments, the infection is resistant to one or more antibiotics when being administered without probenecid or the pharmaceutically acceptable salt thereof.

In some embodiments, the infection is resistant to one or more β-lactam compounds when being administered without probenecid or the pharmaceutically acceptable salt thereof.

In some embodiments, the disease is an uncomplicated urinary tract infection, a complicated urinary tract infection, a complicated intra-abdominal infection, an uncomplicated intra-abdominal infection, pneumonia, otitis media, sinusitis, gonococcal urethritis, pelvic inflammatory disease, prostatitis, bone infection, joint infection, diabetic foot infection and infectious diarrhea.

In some embodiments, the disease is associated with (e.g., resulted from) the alteration of the microbiome in the subject.

In some embodiments, the disease is associated with (e.g., resulted from) the alteration of the microbiome in the human subject.

In some embodiments, the disease is a neurodegenerative disease.

In some embodiments, the disease is amyotrophic lateral sclerosis, Parkinson's disease, Alzheimer's disease, schizophrenia or Huntington's disease.

In some embodiments, the disease is Alzheimer's disease. It is noted that probenecid has been found to increase the concentrations of β-lactam compounds in the cerebrospinal fluid (Ralph G. Dacey and Merle A. Sande, *Antimicrobial Agents and Chemotherapy* 6:437-441 (1974)). More recently, a bacterial pathogen, *Porphyromonas gingivalis*, has been found in brain in association with pathologic lesions, which are associated with Alzheimer's disease (Dominy et al., *Sci. Adv.* 5:eaau3333 (2019), and sulopenem is active against this bacterium (Lois M. Ednie and Peter C. Appelbaum, *Antimicrobial Agents and Chemotherapy* 53: 2163-2170 (2009)). Without wishing to be bound by theory, it is understood that the beta-lactam compounds (e.g., Compound III-2b), when being dosed with probenecid, may lead to more effective treatment of a brain infection with this organism relative to treatment with sulopenem alone.

In some embodiments, the disease is cancer.

In some embodiments, the cancer is a solid cancer, e.g., ovarian cancer, breast cancer, head and neck cancer, renal cancer, bladder cancer, hepatocellular cancer, colorectal cancer, or lymphoma, or any combination thereof.

In some embodiments, the cancer is sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilms' tumor, cervical cancer, testicular tumor, lung carcinoma, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma.

In some embodiments, the cancer is leukemia, e.g., acute lymphocytic leukemia and acute myelocytic leukemia (myeloblastic, promyelocytic, myelomonocytic, monocytic and erythroleukemia); or chronic leukemia (chronic myelocytic (granulocytic) leukemia and chronic lymphocytic leukemia).

In some embodiments, the cancer is polycythemia vera, lymphoma (Hodgkin's disease and non-Hodgkin's disease), multiple myeloma, Waldenstrom's macroglobulinemia, or heavy chain disease.

In some embodiments, the disease is an inflammatory bowel disease.

In some embodiments, the inflammatory bowel disease is Crohn's disease, ulcerative colitis, indeterminate colitis, irritable bowel syndrome, microscopic colitis, diversion colitis, or Behcet's disease.

Administrations

In some embodiments, the bilayer tablet is administered once daily.

In some embodiments, the bilayer tablet is administered twice daily.

In some embodiments, the bilayer tablet is administered three or more times daily.

In some embodiments, the bilayer tablet is administered for about 1 day.

In some embodiments, the bilayer tablet is administered for more than about 1 day.

In some embodiments, the bilayer tablet for about 2 days, about 3 days, about 4 days, about 5 days, about 6 days, about 7 days, about 14 days, or about 30 days.

In some embodiments, the bilayer tablet is administered with one or more drug holidays.

In some embodiments, the bilayer tablet is administered without any drug holiday.

In some embodiments, the bilayer tablet is administered to the subject with food (e.g., the subject is fed).

In some embodiments, the subject is fed within about 1 hour, about 2 hours, about 3 hours, about 6 hours, about 12 hours, about 24 hours, about 2 days, about 5 days, or about 10 days prior to administration of the bilayer tablet.

In some embodiments, the subject in need thereof is fasted for about 1 hour, about 2 hours, ab out 3 hours, about 6 hours, about 12 hours, about 24 hours, about 2 days, about 5 days, or about 10 days prior to administration of the bilayer tablet.

In some embodiments, the subject in need thereof is fed within about 1 hour, about 2 hours, ab out 3 hours, about 6 hours, about 12 hours, about 24 hours, about 2 days, about 5 days, or about 10 days after administration of the bilayer tablet.

In some embodiments, the subject in need thereof is fasted for about 1 hour, about 2 hours, about 3 hours, about 6 hours, about 12 hours, about 24 hours, about 2 days, about 5 days, or about 10 days after administration of the bilayer tablet.

Effects on the AUC and/or $C_{max}$

In some embodiments, the administration results in a plasma concentration for the β-lactam compound having an area under the curve (AUC) that is higher in the subject in need thereof as compared to a comparable subject being administered with a comparable composition.

In some embodiments, the administration results in a maximum plasma concentration ($C_{max}$) in the subject in need thereof that substantially the same as compared to a comparable subject being administered with a comparable composition.

In some embodiments, the administration results in a plasma concentration for the β-lactam compound having:

an area under the curve (AUC) that is higher in the subject in need thereof as compared to a comparable subject being administered with a comparable composition by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having:

an area under the curve (AUC) that is higher in the subject in need thereof as compared to a comparable subject being administered with a comparable composition by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with a comparable composition.

In some embodiments, the administration results in a plasma concentration for the β-lactam compound having:

an area under the curve (AUC) that is higher in the subject in need thereof as compared to a comparable subject being administered with a comparable composition by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is substantially the same as compared to a comparable subject being administered with a comparable composition.

In some embodiments, the administration results in a plasma concentration for the β-lactam compound having:

an area under the curve (AUC) that is higher in the subject in need thereof as compared to a comparable subject being administered with the bilayer tablet without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration.

In some embodiments, the administration results in a plasma concentration for the β-lactam compound having:

an area under the curve (AUC) that is higher in the subject in need thereof as compared to a comparable subject being administered with the bilayer tablet without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is from about 50% to about 150%, from about 60% to about 140%, from about 70% to about 130%, from about 80% to about 120%, from about 90% to about 110%, from about 95% to about 105%, or from 98% to about 102% as compared to a comparable subject being administered with the bilayer tablet without food (e.g., the comparable subject is fasted).

In some embodiments, the administration results in a plasma concentration for the β-lactam compound having:

an area under the curve (AUC) that is higher in the subject in need thereof as compared to a comparable subject being administered with the bilayer tablet without food (e.g., the comparable subject is fasted) by about 5% or greater, about 10% or greater, about 15% or greater, about 20% or greater, about 25% or greater, about 30% or greater, about 40% or greater, about 50% or greater, about 60% or greater, about 80% or greater, about 100% or greater, about 150% or greater, about 200% or greater, about 300% or greater, about 400% or greater, or about 500% or greater within about 30 minutes, about 1 hour, about 2 hours, about 3 hours, about 6 hours, about 12 hours, about 18 hours, about 1 day, about 2 days, about 3 days, about 4 days, about 5 days, about 6 days, or about 7 days from the administration; and a maximum plasma concentration ($C_{max}$) in the subject in need thereof that is substantially the same as compared to a comparable subject being administered with the bilayer tablet without food (e.g., the comparable subject is fasted).

In some embodiments, the administration results in a plasma concentration for the β-lactam compound having:

an area under the curve (AUC) being from about 4325±3000 ng·h/mL, about 4325±2500 ng·h/mL, about 4325±2000 ng·h/mL, about 4325±1500 ng·h/mL, about 4325±1000 ng·h/mL, about 4325±900 ng·h/mL, about 4325±800 ng·h/mL, about 4325±700 ng·h/mL, about 4325±600 ng·h/mL, about 4325±500 ng·h/mL, about 4325±400 ng·h/mL, about 4325±300 ng·h/mL, about 4325±200 ng·h/mL, about 4325±100 ng·h/mL, about 4325±90 ng·h/mL, about 4325±80 ng·h/mL, about 4325±70 ng·h/mL, about 4325±60 ng·h/mL, about 4325±50 ng·h/mL, about 4325±40 ng·h/mL, about 4325±30 ng·h/mL, about 4325±20 ng·h/mL, or about 4325±10 ng·h/mL (e.g., about 4325 ng·h/mL) within about 1 day from the administration.

In some embodiments, the bilayer tablet is administered to the subject in need thereof with food (e.g., the subject is fed), and the administration results in a plasma concentration for the β-lactam compound having:

an area under the curve (AUC) being from about 6600±3000 ng·h/mL, about 6600±2500 ng·h/mL, about 6600±2000 ng·h/mL, about 6600±1500 ng·h/mL, about 6600±1000 ng·h/mL, about 6600±900 ng·h/mL, about 6600±800 ng·h/mL, about 6600±700 ng·h/mL, about 6600±600 ng·h/mL, about 6600±500 ng·h/mL, about 6600±400 ng·h/mL, about 6600±300 ng·h/mL, about 6600±200 ng·h/mL, about 6600±100 ng·h/mL, about 6600±90 ng·h/mL, about 6600±80 ng·h/mL, about 6600±70 ng·h/mL, about 6600±60 ng·h/mL, about 6600±50 ng·h/mL, about 6600±40 ng·h/mL, about 6600±30 ng·h/mL, about 6600±20 ng·h/mL, or about 6600±10 ng·h/mL (e.g., about 6600 ng·h/mL) within about 1 day from the administration.

In some embodiments, the administration results in a plasma concentration for the β-lactam compound having:

an area under the curve (AUC) being from about 5100±3000 ng·h/mL, about 5100±2500 ng·h/mL, about 5100±2000 ng·h/mL, about 5100±1500 ng·h/mL, about 5100±1000 ng·h/mL, about 5100±900 ng·h/mL, about 5100±800 ng·h/mL, about 5100±700 ng·h/mL, about 5100±600 ng·h/mL, about 5100±500 ng·h/mL, about 5100±400 ng·h/mL, about 5100±300 ng·h/mL, about 5100±200 ng·h/mL, about 5100±100 ng·h/mL, about 5100±90 ng·h/mL, about 5100±80 ng·h/mL, about 5100±70 ng·h/mL, about 5100±60 ng·h/mL, about 5100±50 ng·h/mL, about 5100±40 ng·h/mL, about 5100±30 ng·h/mL, about 5100±20 ng·h/mL, or about 5100±10 ng·h/mL (e.g., about 5100 ng·h/mL) within about 1 day from the administration.

In some embodiments, the bilayer tablet is administered to the subject in need thereof with food (e.g., the subject is fed), and the administration results in a plasma concentration for the β-lactam compound having:

an area under the curve (AUC) being from about 7340±3000 ng·h/mL, about 7340±2500 ng·h/mL, about 7340±2000 ng·h/mL, about 7340±1500 ng·h/mL, about 7340±1000 ng·h/mL, about 7340±900 ng·h/mL, about 7340±800 ng·h/mL, about 7340±700 ng·h/mL, about 7340±600 ng·h/mL, about 7340±500 ng·h/mL, about 7340±400 ng·h/mL, about 7340±300 ng·h/mL, about 7340±200 ng·h/mL, about 7340±100 ng·h/mL, about 7340±90 ng·h/mL, about 7340±80 ng·h/mL, about 7340±70 ng·h/mL, about 7340±60 ng·h/mL, about 7340±50 ng·h/mL, about 7340±40 ng·h/mL, about 7340±30 ng·h/mL, about 7340±20 ng·h/mL, or about 7340±10 ng·h/mL (e.g., about 7340 ng·h/mL) within about 1 day from the administration.

Definitions

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl. In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, acylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkyl linker" or "alkylene linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkylene linker is intended to include $C_1$, $C_2$, $C_3$, $C_4$, $C_5$ and $C_6$ alkylene linker groups. Examples of alkylene linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "aryl" includes groups with aromaticity, including "conjugated," or multicyclic systems with one or more aromatic rings and do not contain any heteroatom in the ring structure. Examples include phenyl, naphthalenyl, etc.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, the term "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or

As used herein, the term "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

As used herein, the term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

As used herein, the term "carboxyl" refers to —COOH or its $C_1$-$C_6$ alkyl ester.

As used herein, the term "acyl" includes moieties that contain the acyl radical (R—C(O)—) or a carbonyl group. As used herein, the term "substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, acylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "aroyl" includes moieties with an aryl or heteroaromatic moiety bound to a carbonyl group. Examples of aroyl groups include phenylcarboxy, naphthyl carboxy, etc.

As used herein, the term "alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

As used herein, the term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As used herein, the term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

As used herein, the term "thiocarbonyl" or "thiocarboxy" includes compounds and moieties which contain a carbon connected with a double bond to a sulfur atom.

As used herein, the term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, the term "amine" or "amino" refers to —$NH_2$. "Alkylamino" includes groups of compounds wherein the nitrogen of —$NH_2$ is bound to at least one alkyl group. Examples of alkylamino groups include benzylamino, methylamino, ethylamino, phenethylamino, etc.

As used herein, the term "dialkylamino" includes groups wherein the nitrogen of —NH$_2$ is bound to two alkyl groups. Examples of dialkylamino groups include, but are not limited to, dimethylamino and diethylamino.

As used herein, the terms "arylamino" and "diarylamino" include groups wherein the nitrogen is bound to at least one or two aryl groups, respectively.

As used herein, the terms "aminoaryl" and "aminoaryloxy" refer to aryl and aryloxy substituted with amino.

As used herein, the terms "alkylarylamino," "alkylaminoaryl" or "arylaminoalkyl" refers to an amino group which is bound to at least one alkyl group and at least one aryl group.

As used herein, the terms "alkaminoalkyl" refers to an alkyl, alkenyl, or alkynyl group bound to a nitrogen atom which is also bound to an alkyl group.

As used herein, the terms "acylamino" includes groups wherein nitrogen is bound to an acyl group. Examples of acylamino include, but are not limited to, alkylcarbonylamino, arylcarbonylamino, carbamoyl and ureido groups.

As used herein, the term "amide" or "aminocarboxy" includes compounds or moieties that contain a nitrogen atom that is bound to the carbon of a carbonyl or a thiocarbonyl group.

As used herein, the term "alkaminocarboxy" includes alkyl, alkenyl or alkynyl groups bound to an amino group which is bound to the carbon of a carbonyl or thiocarbonyl group.

As used herein, the term "arylaminocarboxy" includes aryl or heteroaryl moieties bound to an amino group that is bound to the carbon of a carbonyl or thiocarbonyl group.

As used herein, the terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group.

Amides can be substituted with substituents such as straight chain alkyl, branched alkyl, cycloalkyl, aryl, heteroaryl or heterocycle. Substituents on amide groups may be further substituted.

It is understood that probenecid (e.g., sold under the brandname Probalan) is of the following structure:

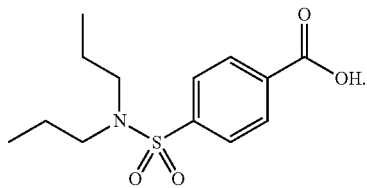 [SMILES: CCCN(CCC)S(=O)(=O)c1ccc(C(=O)O)cc1]

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C$_1$-C$_6$ alkyl, C$_1$-C$_6$ alkenyl, C$_1$-C$_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

As used herein, the term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

It is to be understood that the compounds of any Formula described herein include the compounds themselves, as well as their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure, and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

It is to be understood that the present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999.

It is to be understood that, unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "candidate compound" refers to a compound of the present disclosure, or a pharmaceutically acceptable salt, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present disclosure, or a pharmaceutically acceptable salt, polymorph or solvate thereof. The biological response or effect can occur in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "temporal proximity" refers to that administration of one therapeutic agent (e.g., a β-lactam compound disclosed herein) occurs within a time period before or after the administration of another therapeutic agent (e.g., probenecid), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990), Mandell, et al., *Principles and Practice of Infectious Diseases*, Saunders Publishing (8th edition, 2014). These texts can, of course, also be referred to in making or using an aspect of the disclosure.

As used herein, the term "combination therapy" or "co-therapy" includes the administration of a compound of the present disclosure, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound (e.g., a β-lactam compound or probenecid described herein) is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

As used herein, the term "prodrug" refers to any agent which, when administered to a mammal, is converted in whole or in part to a targeted compound (e.g., a β-lactam compound or probenecid described herein). In some embodiments, the prodrug of a compound (e.g., a β-lactam compound or probenecid described herein) is also a pharmaceutically acceptable salt of the compound.

It is to be understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy,* 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

As used herein, the term "granular material" refers to a conglomeration of discrete solid, macroscopic particles. In some embodiments, the granular material is prepared by granulating a powdery or solid substance (e.g., a common granulation process in the art of chemical and pharmaceutical industry). In some embodiments, the granulation involves agglomeration of fine particles into larger granules (e.g., granules with a size range between 0.2 mm and 4.0 mm). In some embodiments, the granulation involves shredding or grinding solid material into finer granules or pellets.

As used herein, the term "friability" refers to the tendency of a solid substance to break into smaller pieces under duress or contact. In some embodiments, the friability is measured and quantified by common techniques in the art. (e.g., by a method described in USP <1216>). In some embodiments, the friability is measured by a method in which a transparent rotating drum is used and tablet weights taken before and after tumbling.

As used herein, the term "total pore surface area" refers to the total area of the surface of the pores in an object (e.g., a bilayer tablet of the present disclosure). In some embodiments, the total pore surface area is measured by a common technique in the art (e.g., an X-ray Computed Tomography (X-ray CT)).

As used herein, the term "total pore count" refers to the total amount of the pores in an object (e.g., a bilayer tablet of the present disclosure). In some embodiments, the total pore count is measured by a common technique in the art (e.g., an X-ray Computed Tomography (X-ray CT)).

As used herein, the term "largest pore volume" refers to the volume of the largest pore in an object (e.g., a bilayer tablet of the present disclosure). In some embodiments, the largest pore volume is measured by a common technique in the art (e.g., an X-ray Computed Tomography (X-ray CT)).

As used herein, the term "total pore volume" refers to the total volume of all pores in an object (e.g., a bilayer tablet of the present disclosure). In some embodiments, the total pore volume is measured by a common technique in the art (e.g., an X-ray Computed Tomography (X-ray CT)).

As used herein, the term "porosity" refers to a fraction of the volume of void spaces in a material over the total volume of the material. In some embodiments, the porosity is measured by a common technique in the art, e.g., an industrial CT scanning.

In some embodiments, the porosity is measured by X-ray Computed Tomography (X-ray CT). X-ray CT is a non-destructive analysis technique used to visualise and quantify the interior of a material in 3D. In an exemplary procedure, tablets were securely held in an X-ray transparent polystyrene block during scanning. Tablets were scanned individually using a GE V|TOME|X M 240 kV (GE Sensing and Inspection Technologies, Wunstorf, Germany) X-ray CT system. X-ray tube energy and current was 80 kv and 160 µA, respectively. The scan consisted of 2400 radiograph images (each an integration of 8 images to reduce image noise) at a resolution of 14 microns. On data reconstruction a digital magnification factor was used to achieve a final resolution of 7.5 microns. Low attenuating materials such as air (voids) appear as dark regions. Higher attenuating materials or denser regions in the sample appear brighter. Images, animations and microstructural quantification was performed using Volume Graphics VGStudioMAX (v2.2) Software (Volume Graphics, GmbH, Germany).

As used herein, the term "comparable composition" refers to a composition with comparable parameters, or in comparable conditions, as of the bilayer tablet of the present disclosure. In some embodiments, the comparable composition comprises the same amount of probenecid, or the pharmaceutically acceptable salt thereof, and/or the β-lactam compound, or the pharmaceutically acceptable salt thereof, as of the bilayer composition of the present disclosure. In some embodiments, the comparable composition comprises probenecid, or the pharmaceutically acceptable salt thereof (e.g., a commercial composition of probenecid). In some embodiments, the comparable composition comprises the β-lactam compound, or the pharmaceutically acceptable salt thereof (e.g., a commercial composition of Compound III-2b). In some embodiments, the comparable composition comprises probenecid, or the pharmaceutically acceptable salt thereof, and the β-lactam compound, or the pharmaceutically acceptable salt thereof. In some embodiments, the comparable composition is a comparable tablet, i.e., a tablet with comparable parameters, or in comparable conditions, as of the bilayer tablet of the present disclosure. In some embodiments, the comparable tablet comprises the same amount of probenecid, or the pharmaceutically acceptable salt thereof, and/or the β-lactam compound, or the pharmaceutically acceptable salt thereof, as of the bilayer tablet of the present disclosure. In some embodiments, the comparable tablet is a single layer tablet comprising probenecid, or the pharmaceutically acceptable salt thereof (e.g., a commercial tablet of probenecid). In some embodiments, the comparable tablet is a single layer tablet comprising the β-lactam compound, or the pharmaceutically acceptable salt thereof (e.g., a commercial tablet of Compound III-2b). In some embodiments, the comparable tablet is a single layer tablet comprising probenecid, or the pharmaceutically acceptable salt thereof, and the β-lactam compound, or the pharmaceutically acceptable salt thereof. In some embodiments, the comparable tablet is a bilayer tablet prepared by a different process as compared to the bilayer tablet of the present disclosure. In some embodiments, the comparable tablet is a bilayer tablet prepared by a process with one or more different conditions (e.g., pressing sequence, the first force, and/or the second force) as compared to the bilayer tablet of the present disclosure.

In some embodiments, the comparable composition is a suspension or solution with comparable parameters, or in comparable conditions, as of the bilayer tablet of the present disclosure. In some embodiments, the comparable suspension or solution comprises the same amount of probenecid, or the pharmaceutically acceptable salt thereof, and/or the β-lactam compound, or the pharmaceutically acceptable salt thereof, as of the bilayer suspension or solution of the present disclosure. In some embodiments, the comparable suspension or solution comprises probenecid, or the pharmaceutically acceptable salt thereof (e.g., a commercial suspension or solution of probenecid). In some embodiments, the comparable suspension or solution comprises the β-lactam compound, or the pharmaceutically acceptable salt thereof (e.g., a commercial suspension or solution of Compound III-2b). In some embodiments, the comparable suspension or solution comprises probenecid, or the pharmaceutically acceptable salt thereof, and the β-lactam compound, or the pharmaceutically acceptable salt thereof.

In some embodiments, the comparable composition is a combination of the β-lactam compound, or the pharmaceutically acceptable salt thereof, and probenecid, or the pharmaceutically acceptable salt thereof, being formulated in separate formulations that have comparable parameters, or are in comparable conditions, as of the bilayer tablet of the present disclosure. In some embodiments, the comparable composition is a combination of the β-lactam compound, or the pharmaceutically acceptable salt thereof (e.g., Compound III-2b) formulated in a first comparable tablet, suspension, or solution, and probenecid, or the pharmaceutically acceptable salt thereof formulated in a second comparable tablet, suspension, or solution.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Preparation of the Bilayer Tablets

Figure 3:
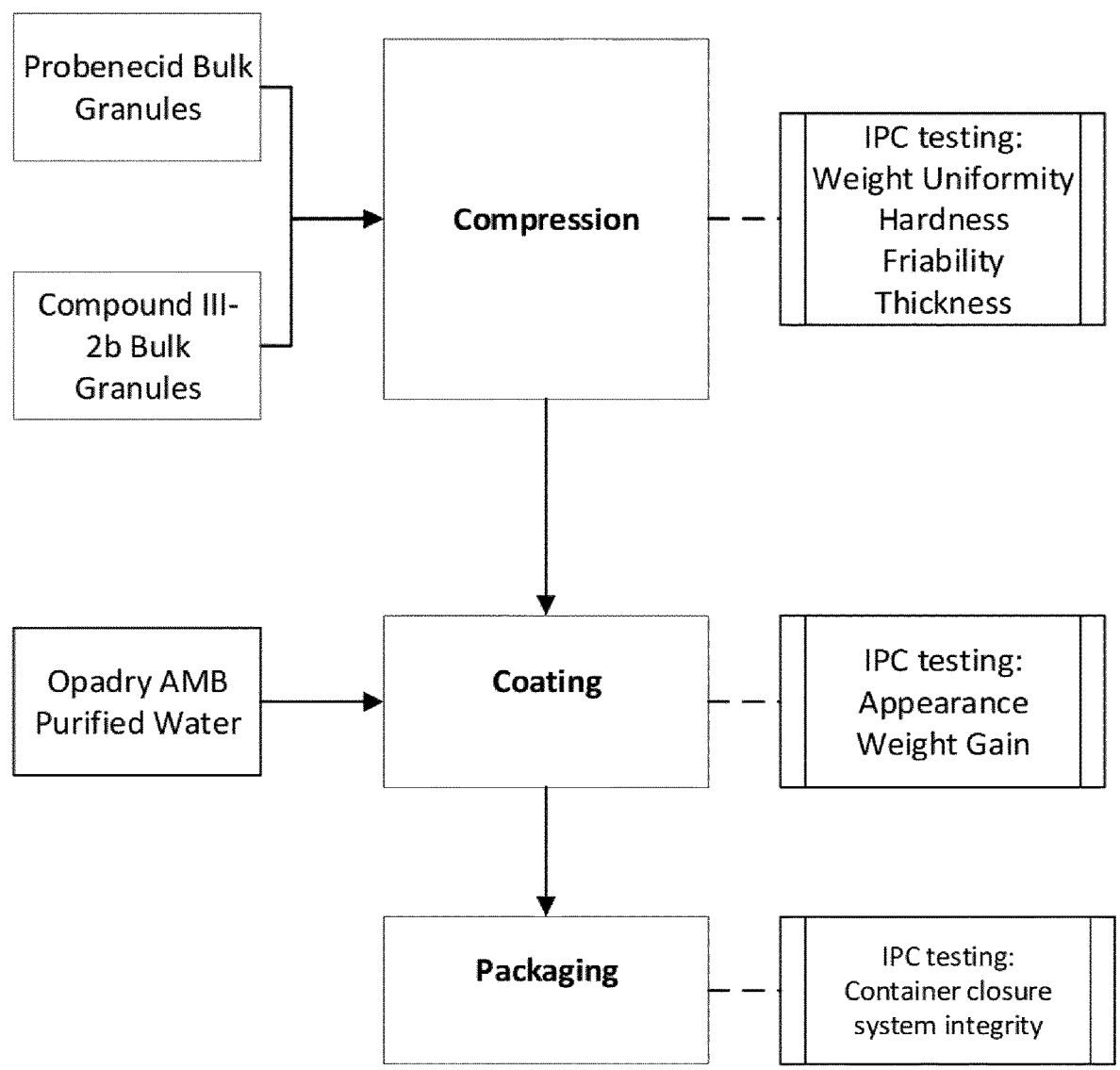
FIG. 3 is a diagram describing an exemplary process of preparing the bilayer tablet of the present disclosure.
Figure 4A:
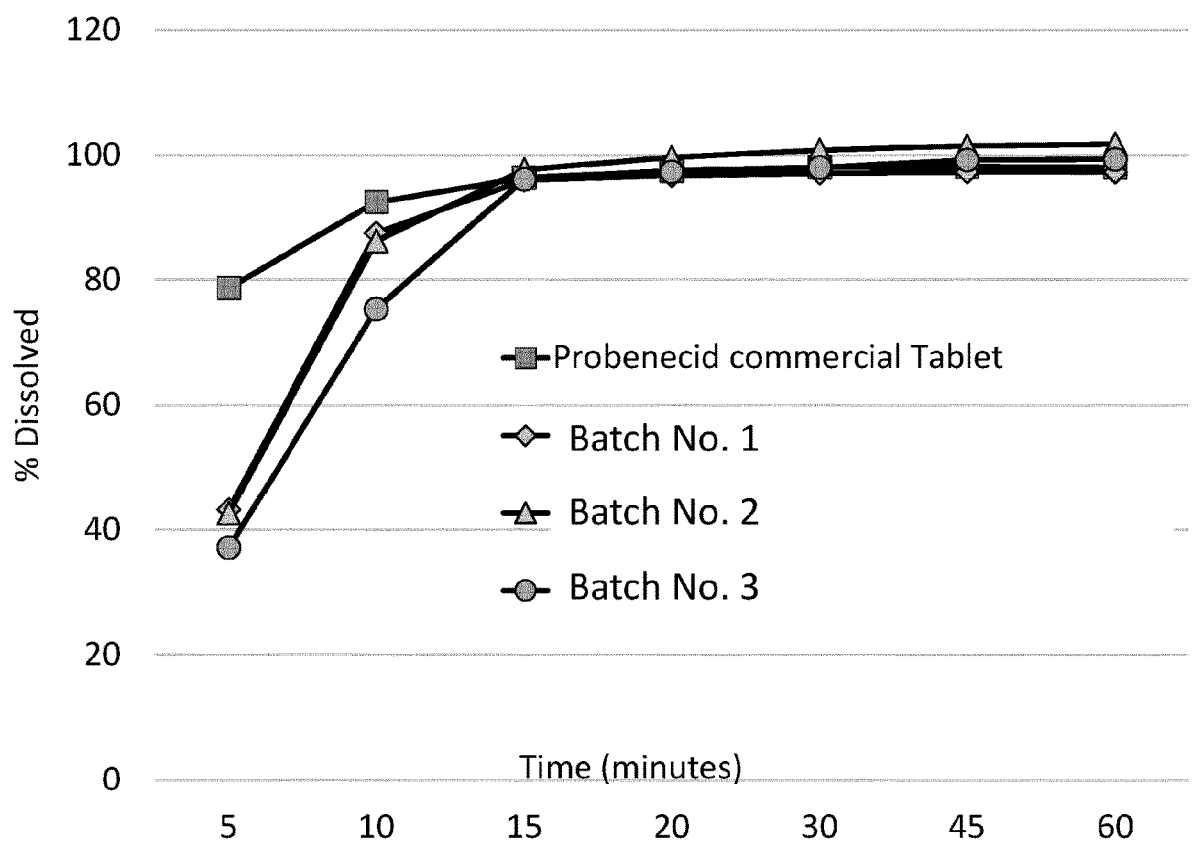
FIGS. 4A-4D are a set of diagrams comparing the in vitro release characteristics of exemplary batches of the bilayer tablet of the present disclosure and a comparable composition.
Figure 4B:
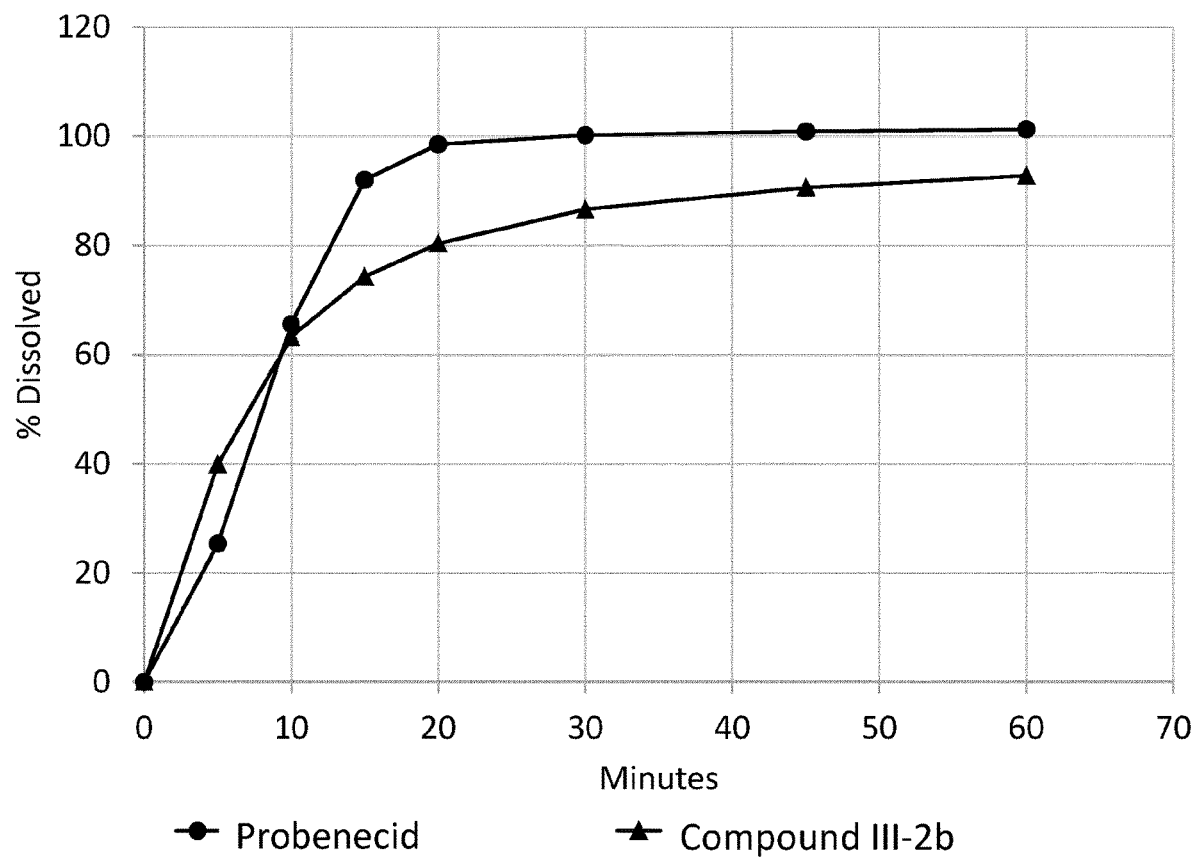
Figure 4C:
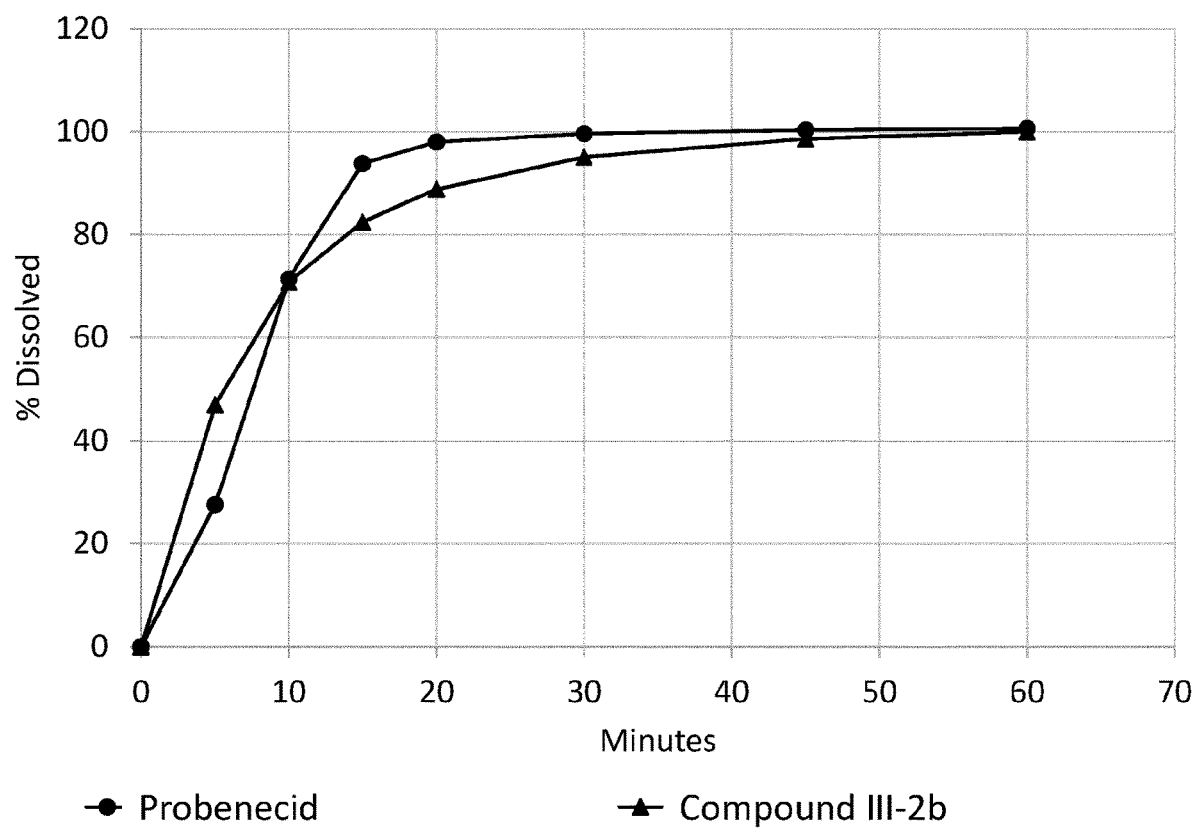
Figure 4D:
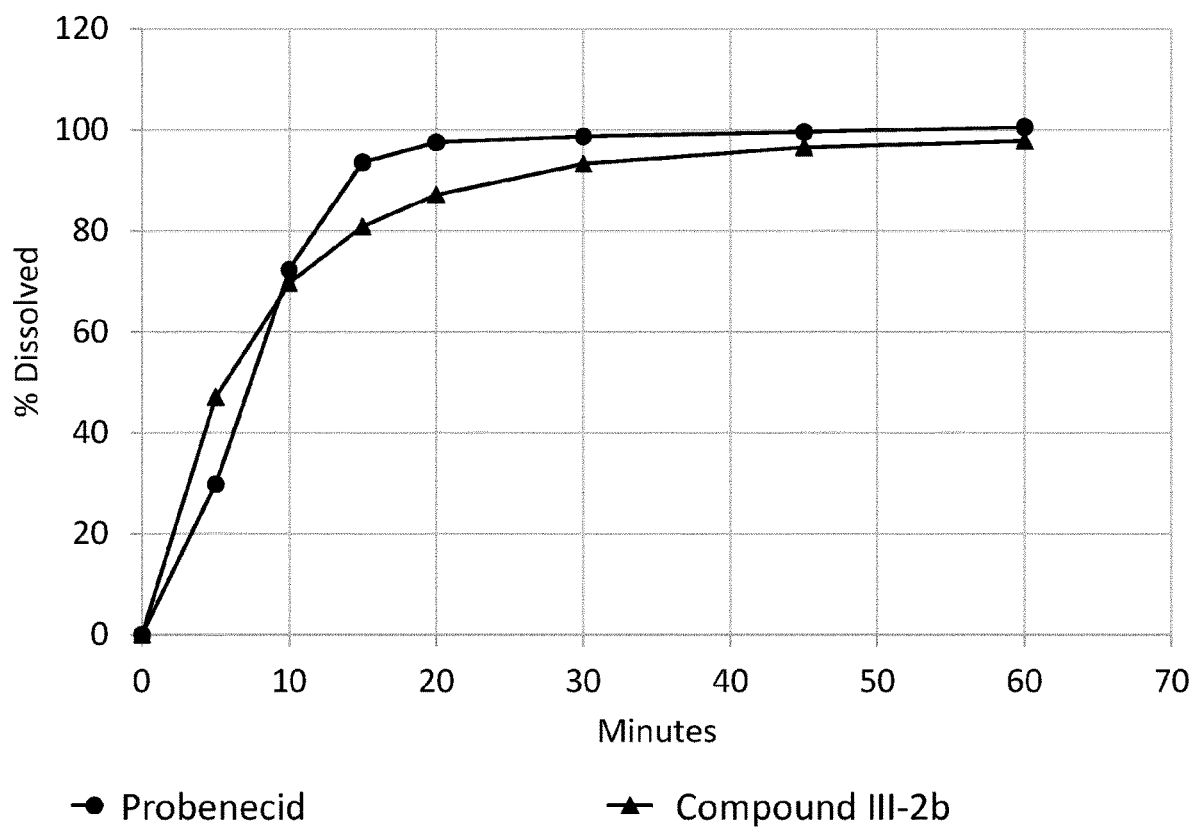

Various batches of bilayer tablets of the present disclosure comprising 500 mg of probenecid and 500 mg of Compound III-2b are prepared according to the processes described in FIGS. 1-3 and to the processes described herein.

Preparing Probenecid Bulk Granular material. The probenecid API and excipients (except magnesium stearate) are loaded into a single pot wet granulator bowl and mixed. The granulation solution (IPA:Water) is then added, with consistent impeller rotation and the chopper rotation. For wet massing the impeller is run until end point achieved (currently defined by time of run). The granule mass is submitted to drying by vacuum and heat prior to granule screening in a cone mill fitted with a suitable opening size rasping screen. Magnesium stearate is added and lubrication takes place.

Preparing Compound III-2b Bulk Granular material. The Compound III-2b API is mixed with the excipients (except magnesium stearate) in an IBC blender and is blended. Magnesium stearate is added to the blend and intragranular lubrication performed. The lubricated blend is dry granulated via one or more roller compactions to obtain compacted ribbon sections. Within the same equipment, ribbons are pre-crushed and screened through suitable size screens. Magnesium stearate is added and lubrication via blending takes place.

Preparing Bilayer Tablets. A rotary tablet press fitted with D type oval die and punch sets is used for tablet compression of the Probenecid and Compound III-2b bulk granules. The first bulk granular material is added and pre-compressed prior to addition of the second bulk granular material and final compression. Exemplary tablets are produced at the target weight of 1381 mg and a target thickness 8.2 mm. Tablets are coated with Opadry® AMB White 80W68912 coating in a coating pan. The target coating weight gain is 4% w/w per tablet.

Composition and physical properties of the prepared tablets are shown in Tables 1A and 1B below.

TABLE 1A

| Component | Grade | Function | % w/w | mg/tablet |
| --- | --- | --- | --- | --- |
| Compound III-2b granular material | | | | |
| Compound III-2b[a] | Pharm | API | 75.0 | 500.0 |
| Microcrystalline cellulose[b] | USP/NF/Ph. Eur. | Filler | 21.0 | 140.0 |
| Croscarmellose sodium | USP/NF/Ph. Eur. | Disintegrant | 3.0 | 20.0 |
| Intragranular Magnesium Stearate | NF/Ph. Eur. | Lubricant | 0.5 | 3.3 |
| Extragranular Magnesium Stearate | NF/Ph. Eur. | Lubricant | 0.5 | 3.3 |
| Layer weight | | | 100 | 666.7 |
| Probenecid granular material | | | | |
| Probenecid[a] | Pharm | API | 70 | 500.0 |
| Microcrystalline cellulose[b] | USP/NF/Ph. Eur. | Filler | 11.9 | 85.0 |
| Lactose monohydrate 316 | USP/NF/Ph. Eur. | Filler | 9.6 | 68.6 |
| Hydroxypropylcellulose | USP/NF/Ph. Eur. | Binder | 3 | 21.4 |
| Croscarmellose sodium | NF/Ph. Eur. | Disintegrant | 5 | 35.7 |
| Extragranular Magnesium Stearate | NF/Ph. Eur. | Lubricant | 0.5 | 3.6 |
| Layer weight | | | 100 | 714.3 |

TABLE 1A-continued

| Component | Grade | Function | % w/w | mg/tablet |
|---|---|---|---|---|
| Bilayer tablet | | | | |
| Bilayer tablet core weight | | | | 1.31 g |
| Coating Opadry AMB | Pharm | Film Coat | 4.0 | 0.05 g |
| Bilayer tablet weight | | | | 1.46 g |

[a] Assuming a potency of 100%
[b] Type PH102; the microcrystalline cellulose weight is adjusted according to correct for potency of the active drug substance.

TABLE 1B

| Property | Value/Range/Description |
|---|---|
| Tablet tensile strength/hardness | 1.6-2.18 MPa (influenced by input granule property (TS) and compression pressure) |
| Tablet weight | 1.36-1.40 g |
| Tablet length | 19 mm |
| Tablet width | 10.3 mm |
| Tablet thickness | 8.0-8.4 mm |
| Tablet friability | <1.0% |
| Ejection force | <3 MPa across run |
| Compression force 1st layer | 1.5 kN (0.5-11.5 kN) |
| Compression force 2nd layer | 11.5 kN (1.5-30 kN) |

In-Process Controls. Loss on Drying is performed on probenecid granules to assure complete drying. Granule uniformity is performed on both probenecid and Compound III-2b granular materials. Throughout tablet manufacture, tablet weight uniformity, hardness, thickness, and friability are checked to assure tablets are produced at the target weight (single layer and tablet core), thickness range, and suitable hardness for further processing. In addition, tablet cores for content uniformity are also collected at defined intervals during process run. Coated tablets are inspected for appearance and weight gain, using AQL sampling. The acceptance criteria for the in-process controls are summarized in Table 2 below.

TABLE 2

| In process Control | Acceptance criteria |
|---|---|
| Probenecid Granule Uniformity | Stage 1: RSD ≤3% w/w if stage 1 not met, progress to stage 2 testing Stage 2: RSD ≤5% w/w |
| Probenecid Granule LOD | LOD ≤3% w/w |
| Sulopenem etzadroxil Granule Uniformity | Stage 1: RSD ≤3% w/w if stage 1 not met, progress to stage 2 testing Stage 2: RSD ≤5% w/w |
| 1st layer individual weight (when Probenecid) | Target: 714.3 mg Warning limits (±2.5%): 696.4-732.2 mg Action limits (±5%): 678.6-750.0 mg |
| 1st layer individual weight (when Sulopenem etzadroxil) | Target: 666.7 mg Warning limits (±2.5%): 650.0-683.4 mg Action limits (±5%): 633.4-700.0 mg |
| 1st layer average weight (10 count) (when Probenecid) | Target: 714.3 mg Warning limits (±1.5%): 703.6-725.0 mg Action limits (3%): 692.9-735.7 mg |
| 1st layer average weight (10 count) (when Sulopenem etzadroxil) | Target: 666.7 mg Warning limits (±1.5%): 656.7-676.7 mg Action limits (±3%): 646.7-688.7 mg |
| Individual tablet core weight | Target: 1381 mg Warning limits (±2.5%): 1346.5-1415.5 mg Action limits (±5%): 1312.0-1450.1 mg |
| Mean tablet core weight (10 count) | Target: 1381 mg Warning limits (±1.5%): 1360.3-1401.7 mg Action limits (±3%): 1339.6-1422.4 mg |
| Tablet Thickness | Target: 8.2 mm; Range 8.0 to 8.4 mm |
| Hardness | Target: 150-250 N |
| Friability (USP <1216>) | NMT 1.0% w/w |
| Tablet core content uniformity | Compare all results to ASTM E2709/E2810 tables for 90% confidence/95% probability of passing USP <905> for a sample size of n = 30 |
| Coated tablet Weight gain | Target: 4% w/w |
| Coated tablet Visual Inspection | White to off-white or pink colored oval shape tablet |

Example 2. In Vitro Release Characteristics of the Bilayer Tablets

The in vitro release characteristics of bilayer tablets prepared according to the procedure described in Example 1 are tested using the USP <711>-compliant method (with conditions shown in Table 3 below) and are analyzed by HPLC-UV (with the HPLC operating conditions shown in Table 4 below).

TABLE 3

| Apparatus | USP Apparatus II (Paddles) |
|---|---|
| Media Temperature | 37° C. |
| Sampling Volume | 2.5 mL |
| Rotation Speed | 75 RPM |
| Media Volume | 900 mL |
| Dissolution Media | Phosphate Buffer pH 6.8 |
| Sampling times | 5, 10, 15, 20, 30, 45 and 60 minutes |

TABLE 4

| Column | Waters X-Select HSS C18, 30 mm × 3.0 mm i.d. 3.5 μm or equivalent |
|---|---|
| Flow Rate | 2.0 mL/min |
| Column Temperature | 30° C. |
| Injection Volume | 20 μL |
| Mobile Phase A | 0.1% Formic Acid in Water |
| Mobile Phase B | 0.1% Formic Acid in Acetonitrile |
| Auto Sampler Temperature | 5° C. |
| Detection | UV 288 nm |
| Run Time | 5 minutes |

| Gradient | Time (min) | % A | % B | Gradient Type |
|---|---|---|---|---|
| | 0 | 95 | 5 | Initial |
| | 3.3 | 5 | 95 | Linear |

TABLE 4-continued

| Column | Waters X-Select HSS C18, 30 mm × 3.0 mm i.d. 3.5 μm or equivalent | | | |
|---|---|---|---|---|
| | 3.4 | 95 | 5 | Step |
| | 5.0 | 95 | 5 | Re-equilibration |

The detailed procedure for the test is described below.

Dissolution Media. Accurately weigh 68 g of potassium dihydrogen phosphate into a 10 L flask and dissolve with an appropriate volume of water. Make to 10 liter total volume with water and mix well. Adjust to pH 6.8.

Standard Solution. Accurately weigh 27.5 mg of Compound III-2b and 27.5 mg of probenecid reference standard into an amber 50 mL volumetric flask. Add approximately 30 mL of dissolution media and sonicate the flask until the standards are completely dissolved. Dilute the flask to volume with dissolution media and mix well.

Test Procedures. Set-up the dissolution bath according to Table 3. Transfer 900 mL of dissolution media into each vessel and ensure the dissolution media is equilibrated to 37° C. Transfer a tablet into each vessel (N=6) and start the dissolution. A volume of media (2.5 mL) is removed from the vessel at each specified time-point according to Table 3. The sample solution is filtered and added to a HPLC vial for analysis against a reference standard solution according to Table 4.

Calculations. Calculate the response factor (RF) for Compound III-2b and probenecid in Standard:

$$RF = \frac{AR \times D}{WR \times P}$$

where:

AR=Area of Compound III-2b or probenecid

WR=weight of Compound III-2b or probenecid standard (mg)

P=Purity of reference standard in decimal format (e.g., 100.0%=1.00)

D=Dilution factor of standard

Calculate the content (mg) of Compound III-2b and probenecid dissolved at each timepoint:

$$C1 = \left(\frac{A1 \times V}{RF\ AVG}\right)$$

$$C2 = \left(\frac{A2 \times (V - PV)}{RF\ AVG}\right) + (C1)$$

$$C3 = \left(\frac{A3 \times (V - (2 \times PV))}{RF\ AVG}\right) + (C1 + C2)$$

$$C4 = \left(\frac{A4 \times (V - (3 \times PV))}{RF\ AVG}\right) + (C1 + C2 + C3)$$

$$C5 = \left(\frac{A5 \times (V - (4 \times PV))}{RF\ AVG}\right) + (C1 + C2 + C3 + C4)$$

$$C6 = \left(\frac{A6 \times (V - (5 \times PV))}{RF\ AVG}\right) + (C1 + C2 + C3 + C4 + C5)$$

where:

$A_n$=Peak area response of Compound III-2b or probenecid in the sample at withdrawal point "n"

RF AVG=Average standard response factor for Compound III-2b or probenecid from the bracketing standard of each sample V=Initial volume of medium=900 mL PV=Pull volume (mL)

$C_n$=Content (mg)

Calculate the percent of Compound III-2b and probenecid dissolved at each time-point:

$$\%\ \text{Dissolved at each time point} = \left(\frac{Cn}{LC}\right) \times (100)$$

where:

LC=Label claim 500 mg for Compound III-2b and 500 mg for probenecid

"Cn"=Content of Compound III-2b and probenecid (mg) at each time-point

Method Validation. The analysis by HPLC-UV has been validated. The parameters evaluated, acceptance criteria and results are presented in Table 5 and are in compliance with ICH Q2 requirements. The method is validated for its intended purpose.

TABLE 5

| Parameter | Acceptance Criteria | Result |
|---|---|---|
| Specificity | No interfering peak >1% in the elution zone of Compound III-2b and probenecid | No interfering peak >1% in the elution zone of Compound III-2b and probenecid |
| Accuracy | The recovery at each level should be within 95% to 105% over a range from 50% to 120% of nominal concentration | Compound III-2b 50% = 96.5% 100% = 97.3% 120% = 97.3% Probenecid 50% = 104.4% 100% = 100.2% 120% = 99.0% |

TABLE 5-continued

| Parameter | Acceptance Criteria | Result |
|---|---|---|
| Precision | % RSD ≤2.0% | Compound III-2b % RSD = 0.2% |
|  |  | Probenecid % RSD = 0.3% |
| Filter | The % Recoveries are within | Compound III-2b |
| Suitability | 95%-105% | 99.3%, 99.6% |
|  |  | Probenecid |
|  |  | 99.2%, 99.8% |

Several exemplary batches of bilayer tablet are prepared with first and second compression forces shown in Table 6A. The in vitro release characteristics of the exemplary batches of bilayer tablets are shown in Table 6B below and in FIGS. 4A-4D.

TABLE 6A

| | First Compression Force (kN) | Second Compression Force (kN) |
|---|---|---|
| Batch No 1 | 0.94 | 13.12 |
| Batch No 2 | 0.51 | 8.34 |
| Batch No 3 | 2.12 | 12.65 |
| Batch No 4 | 2.77 | 15.51 |
| Batch No 5 | 2.18 | 14.27 |
| Batch No 6 | 2.56 | 13.22 |

TABLE 6B

| | Batch No. 1 | | Batch No. 2 | | Batch No. 3 | |
|---|---|---|---|---|---|---|
| Sampling Time (min) | Released Compound III-2b (%) | Released Probenecid (%) | Released Compound III-2b (%) | Released Probenecid (%) | Released Compound III-2b (%) | Released Probenecid (%) |
| 5 | 47 | 41 | 52 | 43 | 54 | 37 |
| 10 | 71 | 87 | 74 | 86 | 77 | 75 |
| 15 | 84 | 96 | 84 | 98 | 87 | 96 |
| 20 | 92 | 97 | 89 | 100 | 93 | 97 |
| 30 | 100 | 97 | 95 | 101 | 98 | 98 |
| 45 | 102 | 97 | 96 | 101 | 100 | 99 |
| 60 | 102 | 97 | 97 | 102 | 102 | 99 |

| | Batch No. 4 | | Batch No. 5 | | Batch No. 6 | |
|---|---|---|---|---|---|---|
| Sampling Time (min) | Released Compound III-2b (%) | Released Probenecid (%) | Released Compound III-2b (%) | Released Probenecid (%) | Released Compound III-2b (%) | Released Probenecid (%) |
| 5 | 40 | 25 | 47 | 28 | 47 | 30 |
| 10 | 63 | 66 | 71 | 71 | 70 | 72 |
| 15 | 74 | 92 | 82 | 94 | 81 | 94 |
| 20 | 80 | 99 | 89 | 98 | 87 | 98 |
| 30 | 87 | 100 | 95 | 100 | 93 | 99 |
| 45 | 91 | 101 | 99 | 100 | 97 | 100 |
| 60 | 93 | 101 | 100 | 101 | 98 | 101 |

Example 3. Effects of Pressing Force on the Physical Properties of the Bilayer Tablets Bilayer tablets are prepared according to the procedure described in Example 1 and with various first and second pressing forces (shown in Table 7A below).

TABLE 7A

| Tablet Sample # | First Force (kN) | Second Force (kN) |
|---|---|---|
| 1 | 1.50 | 11.50 |
| 2 | 11.50 | 1.50 |
| 3 | 1.25 | 30.00 |
| 4 | 2.00 | 20.00 |
| 5 | 1.25 | 15.00 |
| 6 | 0.50 | 10.00 |
| 7 | 1.25 | 5.00 |

Figure 5A:
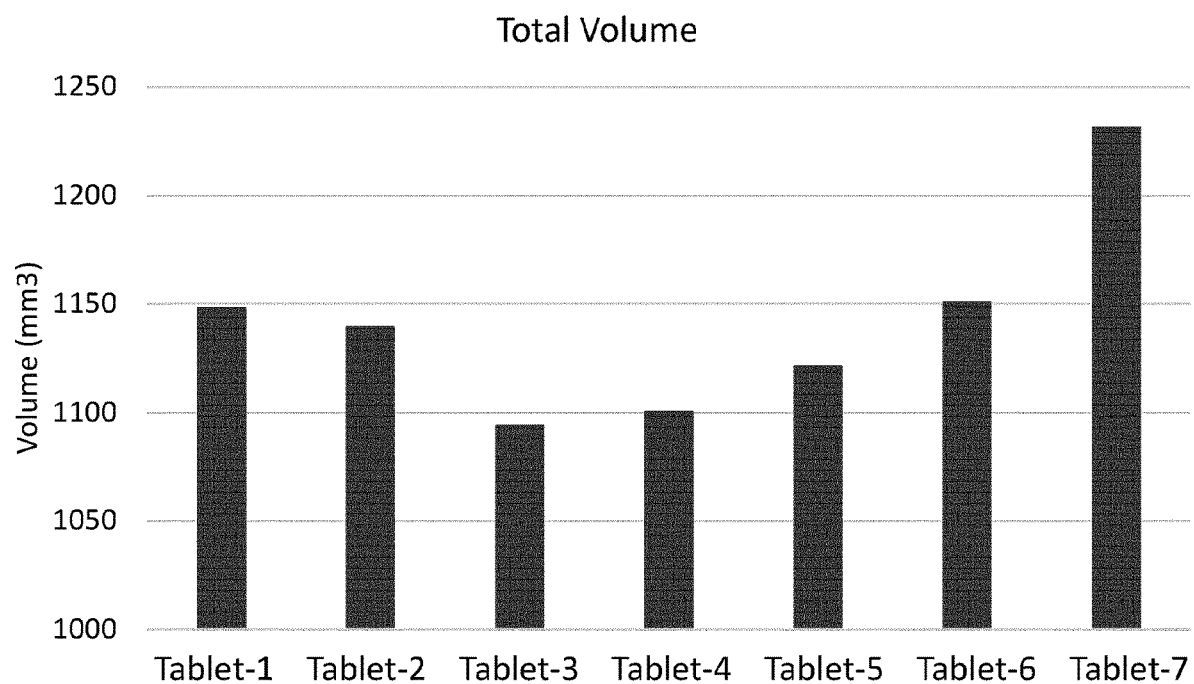
FIGS. 5A-5G are a set of diagrams comparing several physical properties and in vitro release characteristics of the bilayer tablets prepared with various first and second compression forces.
Figure 5B:
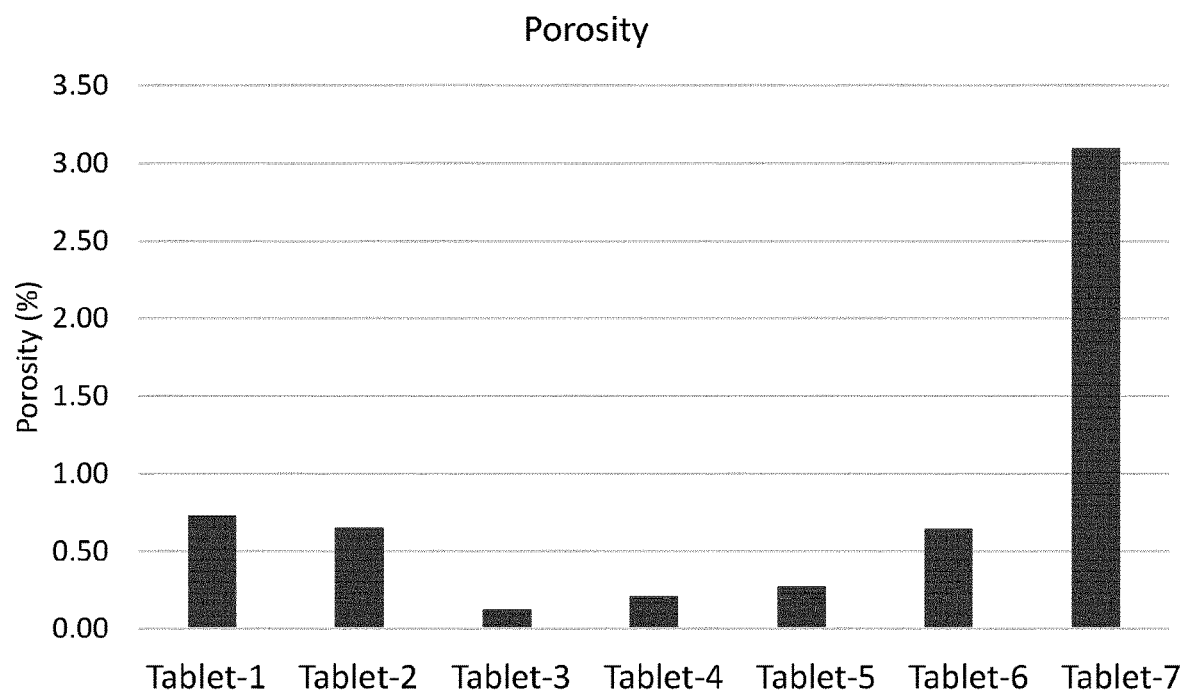
Figure 5C:
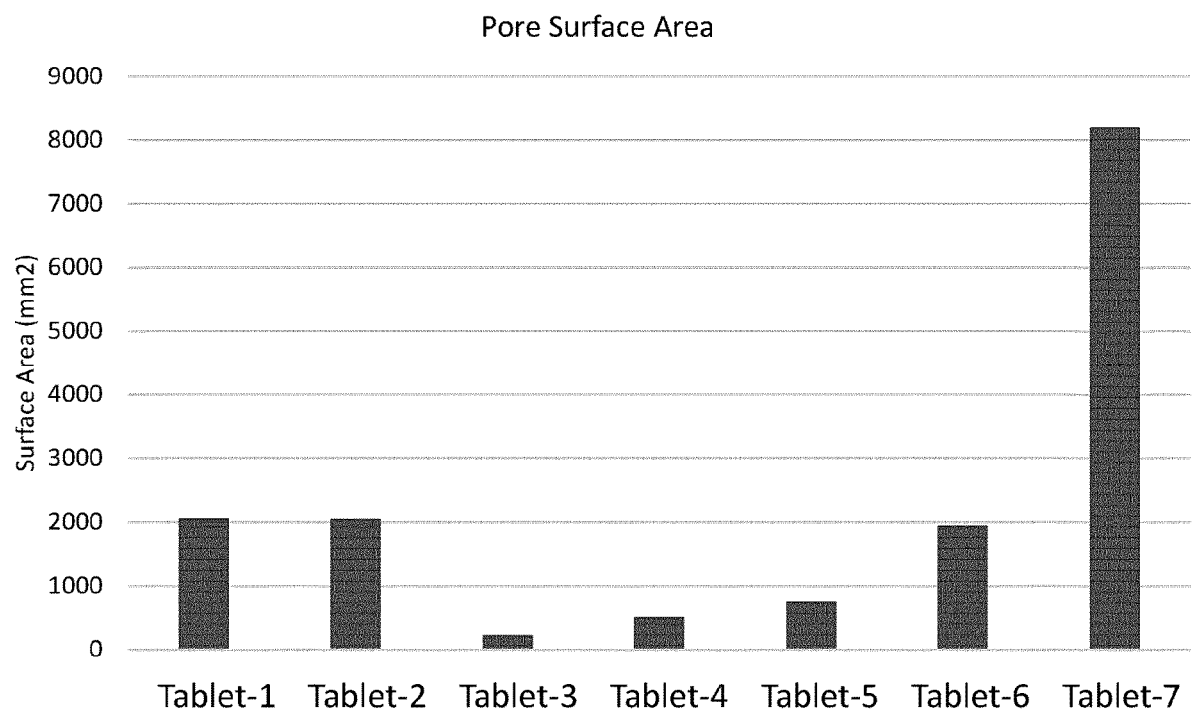
Figure 5D:
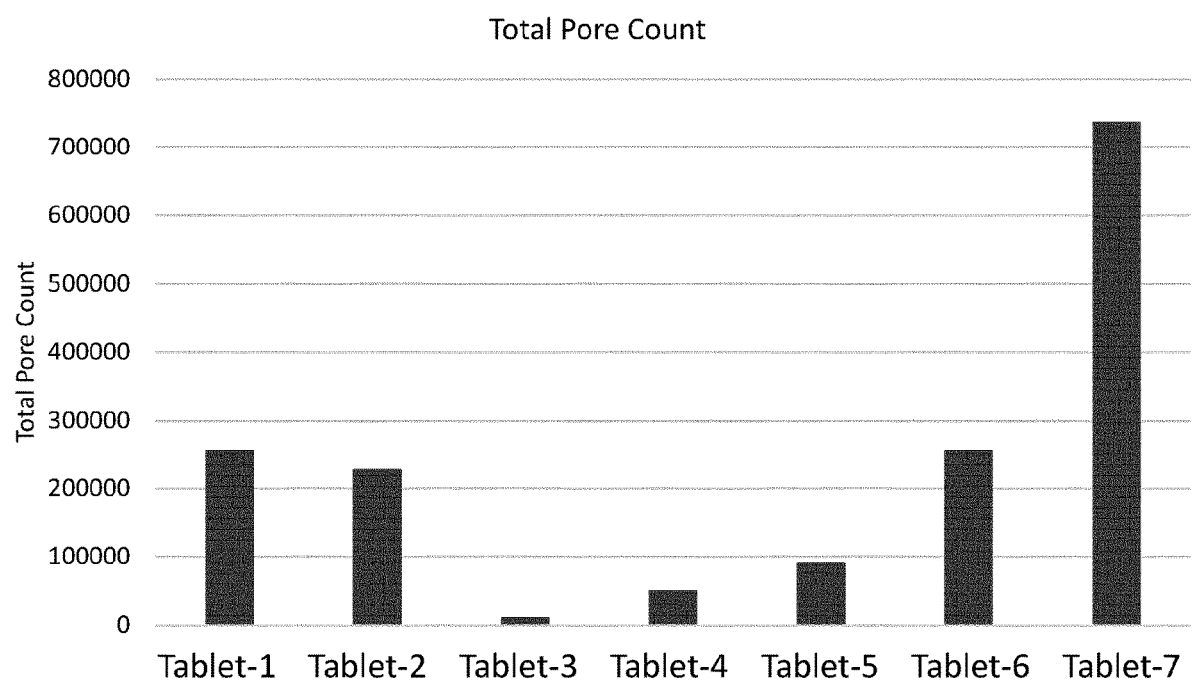
Figure 5E:
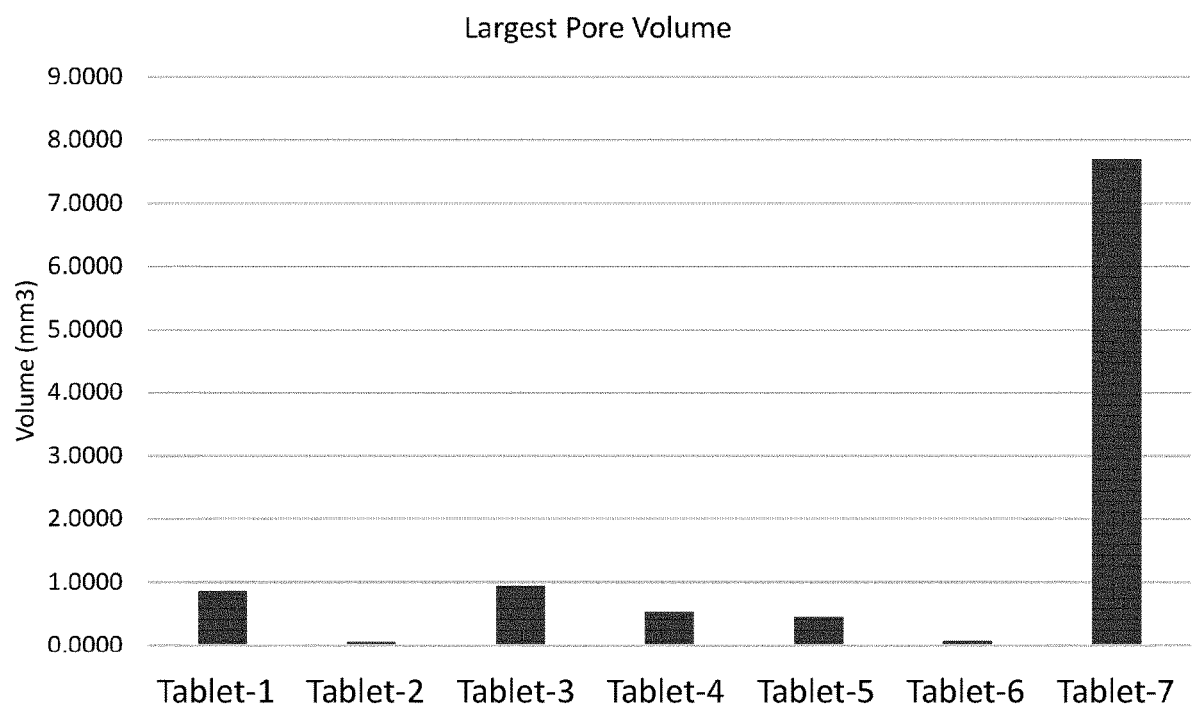
Figure 5F:
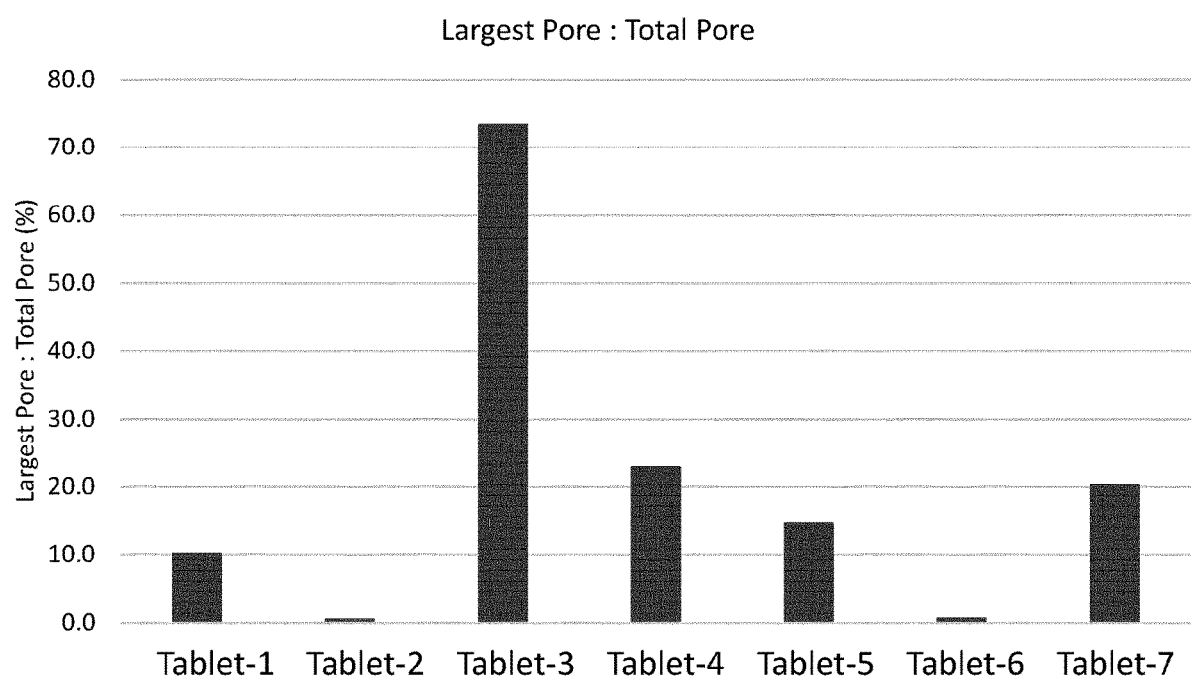
Figure 5G:
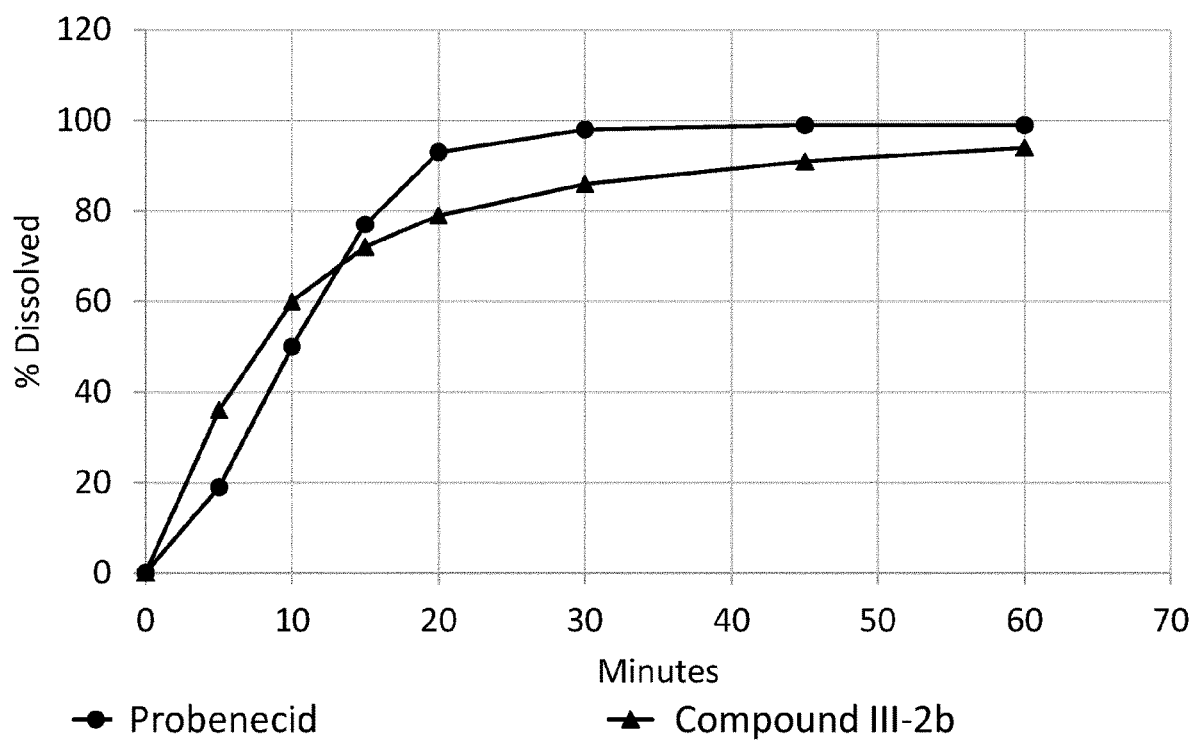
Figure 6:
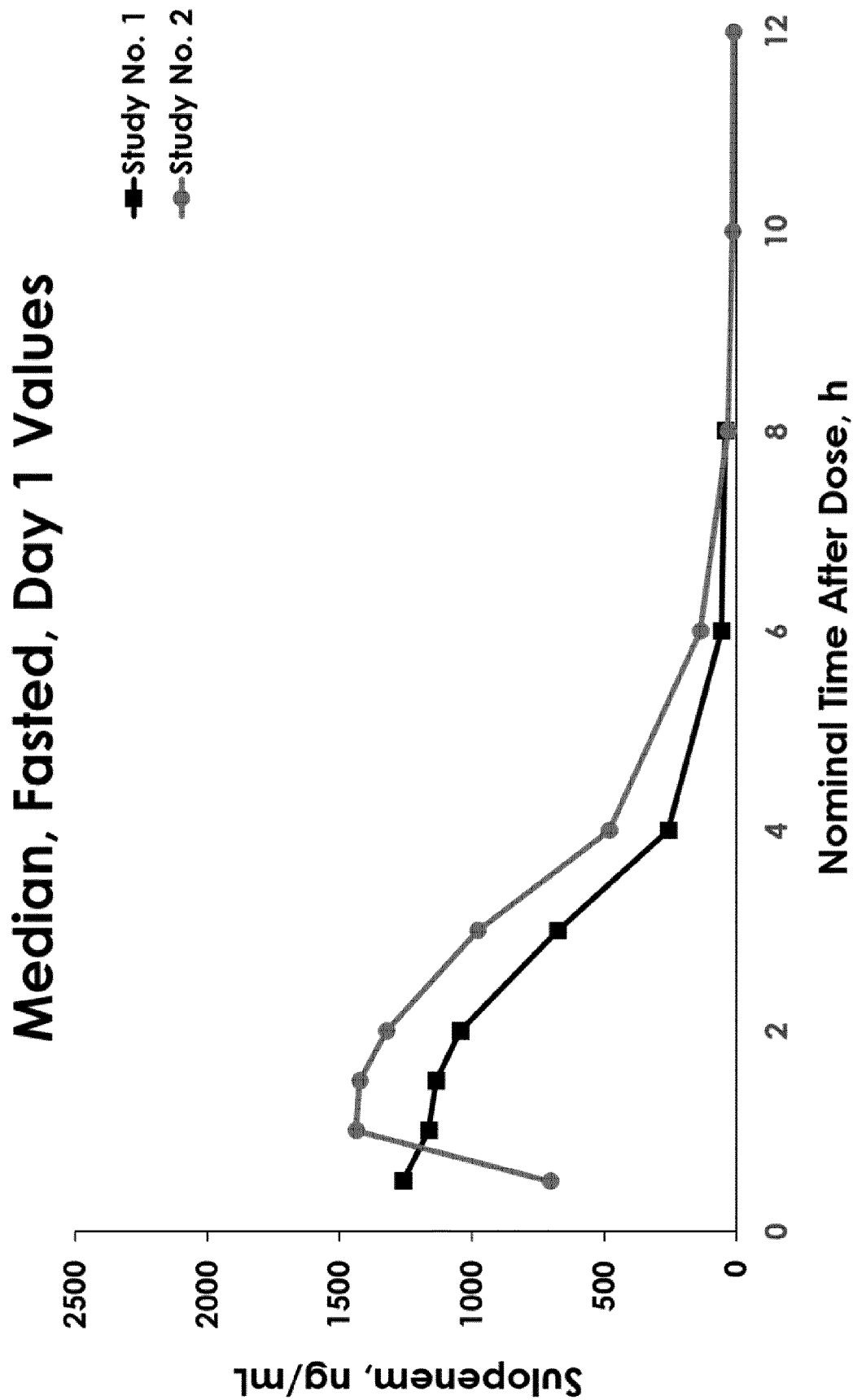
FIG. 6 is a diagram showing the effect of administrating the β-lactam compound (Compound III-2b) and probencid in a bilayer tablet (as compared to in separate formulations) in the fasted state on the plasma level of the β-lactam compound (Compound IIb).
Figure 7:
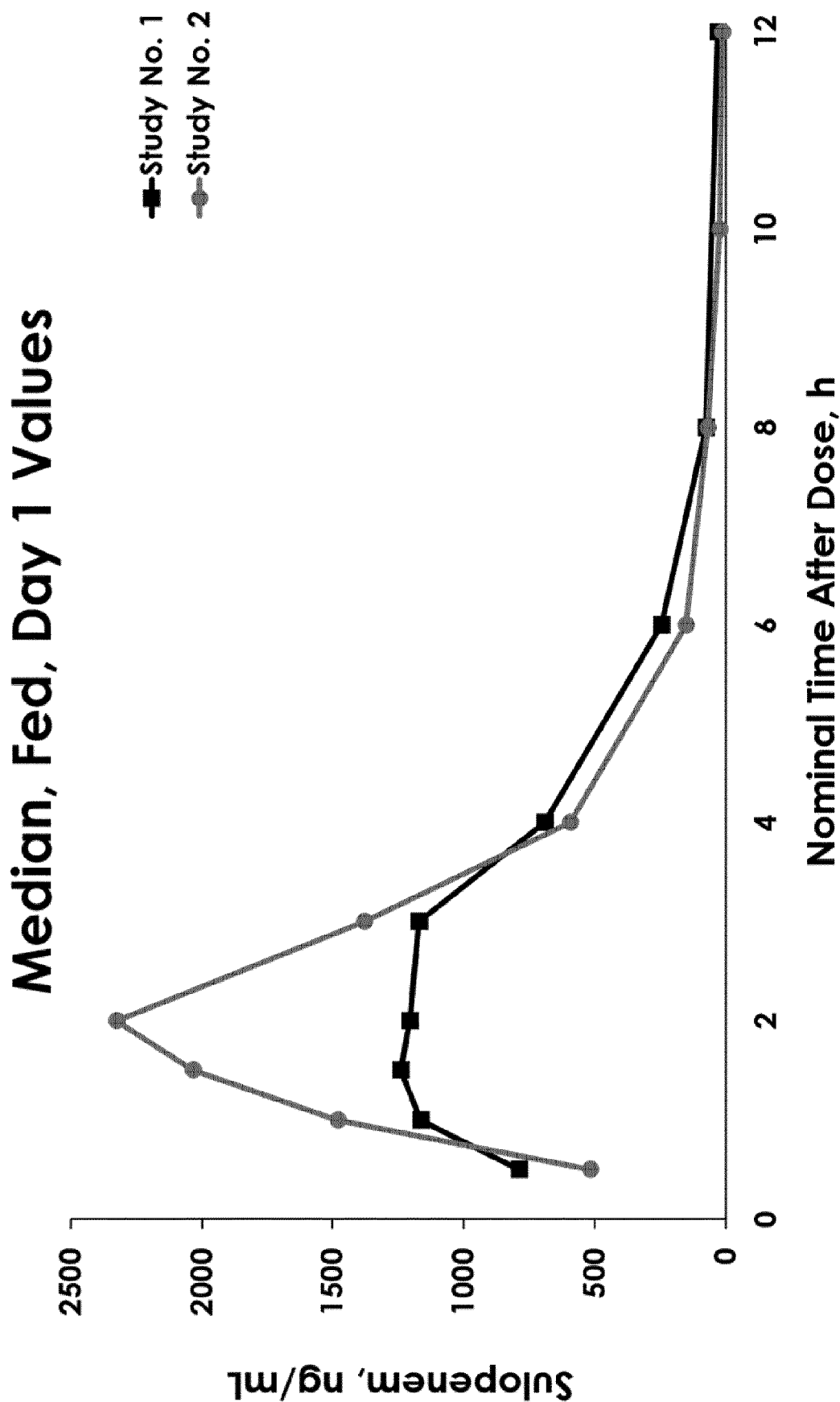
FIG. 7 is a diagram showing the effect of administrating the β-lactam compound (Compound III-2b) and probencid in a bilayer tablet (as compared to in separate formulations) in the fed state on the plasma level of the β-lactam compound (Compound IIb).
Figure 8:
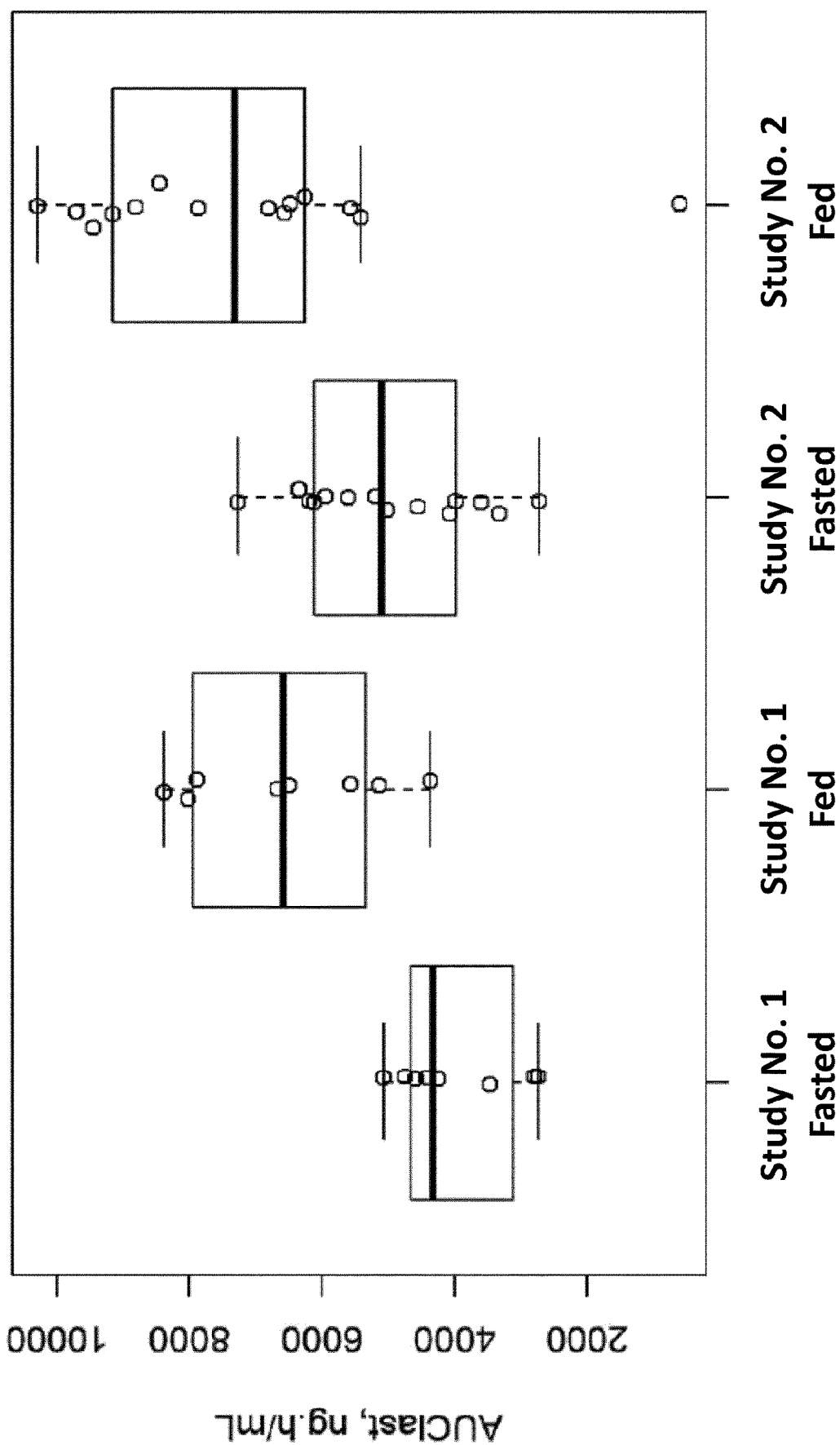
FIG. 8 is a graph showing the effect of administering a β-lactam compound (Compound III-2b) and probenecid in a bilayer tablet (as compared to in separate formulations) on the area under the curve (AUC) for the β-lactam compound (Compound IIb).
Figure 9:
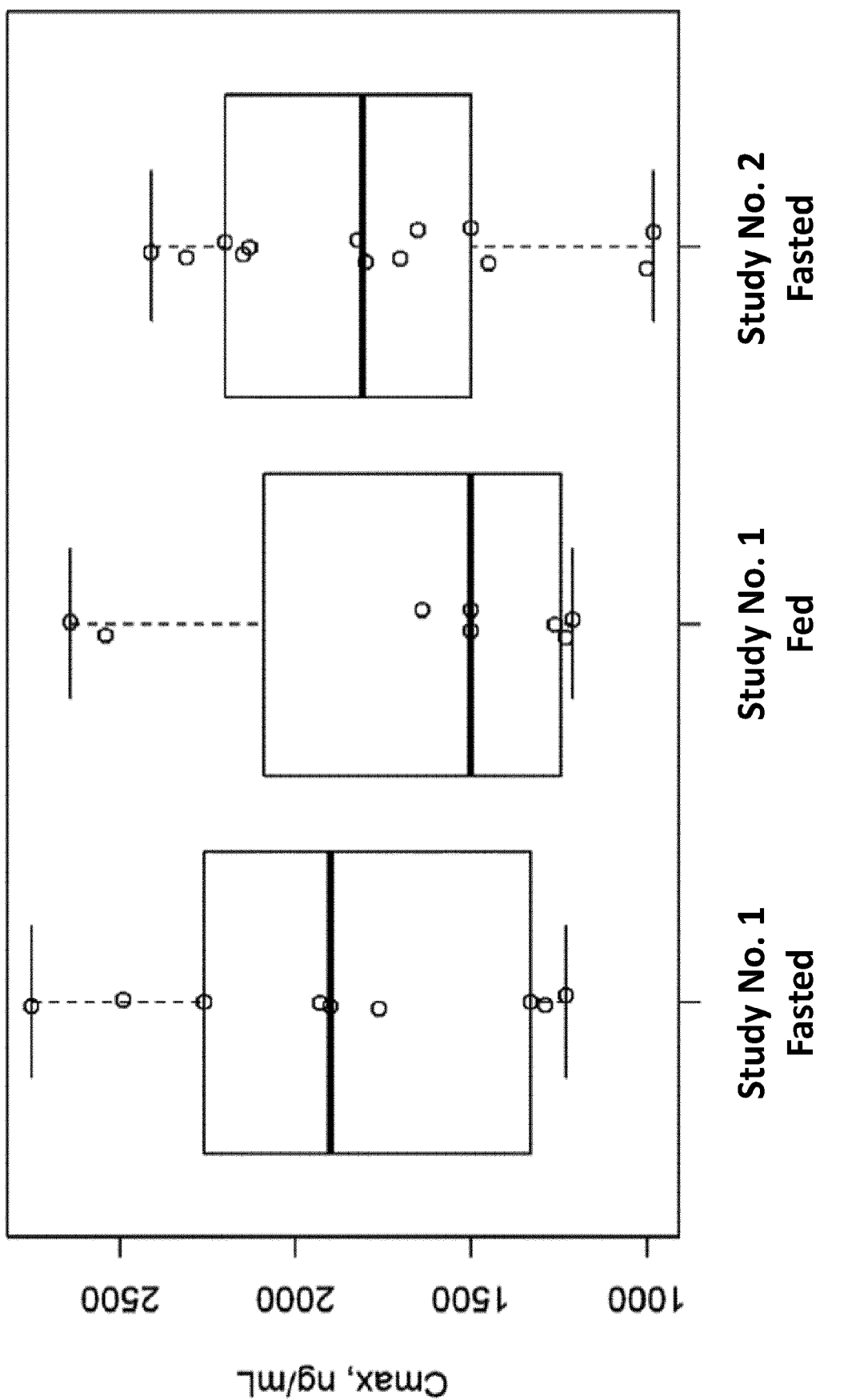
FIG. 9 is a graph showing the effect of administering a β-lactam compound (Compound III-2b) and probenecid in a bilayer tablet (as compared to in separate formulations) on the maximum plasma concentration ($C_{max}$) for the β-lactam compound (Compound III-2b).

The tables are characterized by X-ray Computed Tomography (X-ray CT) and the collected data are subsequently quantified. X-ray Computed Tomography (X-ray CT). X-ray CT is a non-destructive analysis technique used to visualise and quantify the interior of a material in 3D. Tablets were securely held in an X-ray transparent polystyrene block during scanning. Tablets were scanned individually using a GE V|TOME|X M 240 kV (GE Sensing and Inspection Technologies, Wunstorf, Germany) X-ray CT system. X-ray tube energy and current was 80 kv and 160 μA, respectively. The scan consisted of 2400 radiograph images (each an integration of 8 images to reduce image noise) at a resolution of 14 microns. On data reconstruction a digital magnification factor was used to achieve a final resolution of 7.5 microns. Low attenuating materials such as air (voids) appear as dark regions. Higher attenuating materials or denser regions in the sample appear brighter. Images, animations and microstructural quantification was performed using Volume Graphics VGStudioMAX (v2.2) Software (Volume Graphics, GmbH, Germany). Physical characteristics of the tablets a shown in FIGS. 5A-5F. The in vitro release characteristics of an exemplary batch of bilayer tablets (prepared by first compression force at 2.06 kN and second compression force at 25.69 kN) are shown in FIG. 5G and Table 7B.

TABLE 7B

| Sampling Time (min) | Released Compound III-2b (%) | Released Probenecid (%) |
|---|---|---|
| 5 | 36 | 19 |
| 10 | 60 | 50 |
| 15 | 72 | 77 |
| 20 | 79 | 93 |
| 30 | 86 | 98 |
| 45 | 91 | 99 |
| 60 | 94 | 99 |

Example 4: Effects of Administrating β-Lactam Compounds and Probenecid by the Same Administration Route Normal and healthy subjects were given the β-lactam compound (Compound III-2b; sulopenem etzadroxil) and probenecid in two separate studies. In Study No. 1, subjects were administered 500 mg of sulopenem etzadroxil as a powder for oral suspension and simultaneously dosed with 500 mg of probenecid provided as a monolayer tablet. In Study No. 2, subjects were administered 500 mg of sulopenem etzadroxil with 500 mg of probenecid in a bilayer tablet. The results of the two studies are shown in FIGS. 6-9 and Table 8 below.

TABLE 8

| | $AUC_{last}$ ng · hr/ml | |
|---|---|---|
| | Fasted | Fed |
| Study No. 1 | 4325.9 | 6592.8 |
| Study No. 2 | 5099.5 | 7336.4 |
| Difference | 773.6 | 743.6 |
| (% Increase) | (17.9%) | (11.3%) |

It is observed that administration of sulopenem etzadroxil and probenecid in the bilayer tablet results in an increase in the amount of sulopenem in the blood relative to dosing each agent in a separate formulation.

Administration in the fasted state of a combination of sulopenem etzadroxil and probenecid in the bilayer tablet results in a 17.9% increase in the amount of sulopenem in the blood, as measured by the area under the curve, relative to the same amount of sulopenem etzadroxil delivered as powder in a bottle administered with probenecid in a monolayer tablet.

Similarly, the administration in the fed state of a combination of sulopenem etzadroxil and probenecid in the bilayer tablet results in a 11.3% increase in the amount of sulopenem in the blood, as measured by the area under the curve, relative to the same amount of sulopenem etzadroxil delivered as powder in a bottle administered with probenecid in a monolayer tablet.

EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A bilayer tablet, comprising:
a first layer comprising about 500 mg of probenecid or a pharmaceutically acceptable salt thereof;
a second layer comprising about 500 mg of:

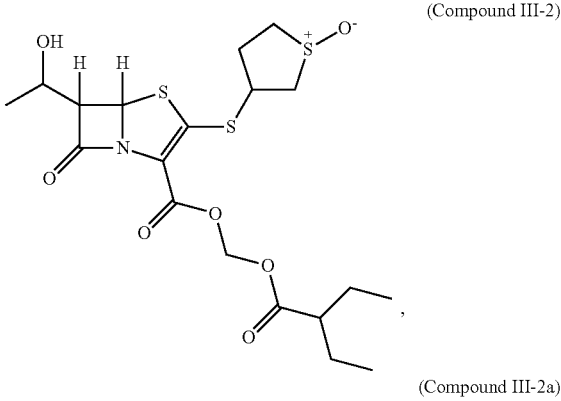

(Compound III-2)

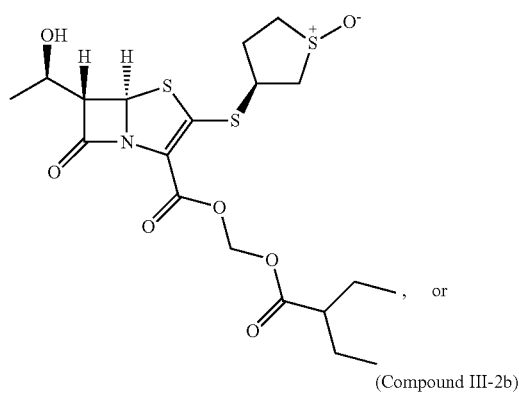

(Compound III-2a)

, or

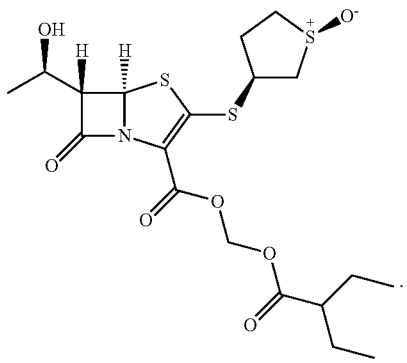

(Compound III-2b)

.

and
   from about 220 mg to about 230 mg of microcrystalline cellulose;
   from about 50 mg to about 60 mg of sodium croscarmellose;
   from about 3 mg to about 4 mg of intragranular magnesium stearate;
   from about 6 mg to about 8 mg of extragranular magnesium stearate;
   from about 65 mg to about 75 mg of lactose monohydrate; and
   from about 20 to about 23 mg of hydroxypropylcellulose.

2. A method of preparing the bilayer tablet of claim 1, comprising:
   i) compressing a first granular material comprising probenecid or a pharmaceutically acceptable salt thereof with a first force, thereby forming a pre-compressed first layer;
   ii) adding a second granular material comprising Compound III-2 to the pre-compressed first layer; and
   iii) compressing the pre-compressed first layer and the second granular material with a second force, thereby forming a pre-coated bilayer tablet.

3. A method of treating or preventing a disease, comprising administering to a subject in need thereof a pharmaceutically effective amount of the bilayer tablet of claim 1.

4. The method of claim 3, wherein the subject in need thereof is a human.

5. The method of claim 3, wherein the disease comprises an increased or decreased population of one or more bacteria selected from *Escherichia coli, Klebsiella pneumoniae, Proteus mirabilis, Enterobacter cloacae, Klebsiella oxytoca, Citrobacter freundii* complex, *Clostridium clostridioforme, Eubacterium* lentum, *Peptostreptococcus* species, *Bacteroides fragilis, Bacteroides distasonis, Bacteroides ovatus, Bacteroides thetaiotaomicron, Bacteroides uniformis, Porphyromonas asaccharolytica, Prevotella bivia, Staphylococcus epidermidis, Streptococcus pneumonia, Staphylococcus aureus, Streptococcus agalactiae, Streptococcus pyogenes, Citrobacter freundii, Citrobacter koseri, Enterobacter aerogenes, Enterobacter cloacae, Haemophilus influenza, Haemophilus parainfluenzae, Klebsiella oxytoca, Moraxella catarrhalis, Morganella morganii, Proteus vulgaris, Providencia rettgeri, Providencia stuartii, Serratia marcescens Bacteroides* vulgatus, *Clostridium perfringens,* and *Fusobacterium* spp.

6. The method of claim 3, wherein the disease is an infection selected from an uncomplicated urinary tract infection, a complicated urinary tract infection, a complicated intra-abdominal infection, pneumonia, otitis media, sinusitis, gonococcal urethritis, pelvic inflammatory disease, prostatitis, bone infection, joint infection, diabetic foot infection, and infectious diarrhea.

7. The method of claim 3, wherein the disease is a neurodegenerative disease, amyotrophic lateral sclerosis, Parkinson's disease, Alzheimer's disease, or Huntington's disease, cancer, or an inflammatory bowel disease.

8. The method of claim 3, wherein the bilayer tablet is administered to the subject with food.

9. The method of claim 3, wherein the administration results in a plasma concentration for the β-lactam compound having an area under the curve (AUC) that is higher in the subject in need thereof as compared to a comparable subject being administered with a comparable composition.

10. The method of claim 3, wherein the administration results in a maximum plasma concentration ($C_{max}$) in the subject in need thereof that substantially the same as compared to a comparable subject being administered with a comparable composition.

* * * * *

UNITED STATES PATENT AND TRADEMARK OFFICE
CERTIFICATE OF CORRECTION

PATENT NO. : 11,478,428 B2  
APPLICATION NO. : 16/972300  
DATED : October 25, 2022  
INVENTOR(S) : Michael Dunne et al.

Page 1 of 2

It is certified that error appears in the above-identified patent and that said Letters Patent is hereby corrected as shown below:

In the Claims

At Column 70, Claim number 1, Line numbers 20 – 67:

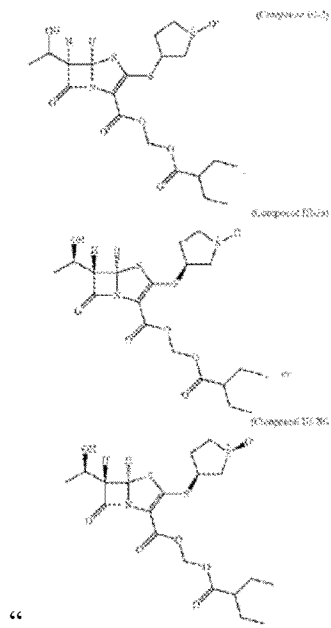

"

Should read:

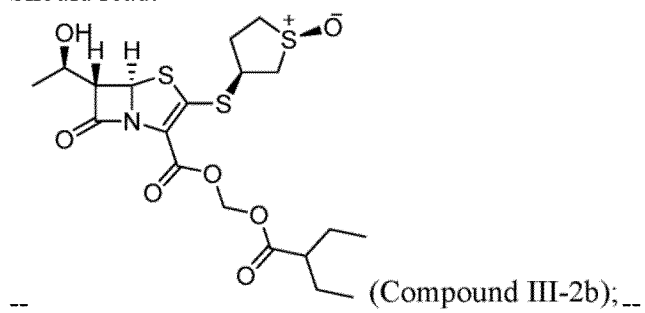

-- (Compound III-2b); --

Signed and Sealed this  
Twenty-eighth Day of March, 2023

*Katherine Kelly Vidal*

Katherine Kelly Vidal  
*Director of the United States Patent and Trademark Office*

CERTIFICATE OF CORRECTION (continued)
U.S. Pat. No. 11,478,428 B2

At Column 71, Claim number 1, Line numbers 4 – 5:
"from about 50 mg to about 60 mg of sodium croscarmellose"
Should read:
--from about 50 mg to about 60 mg of sodium croscamellose--